(12) United States Patent
Yoshikawa et al.

(10) Patent No.: US 9,134,261 B2
(45) Date of Patent: Sep. 15, 2015

(54) INSPECTION APPARATUS

(71) Applicant: EBARA CORPORATION, Tokyo (JP)

(72) Inventors: Shoji Yoshikawa, Tokyo (JP); Kiwamu Tsukamoto, Tokyo (JP); Takeshi Murakami, Tokyo (JP); Masahiro Hatakeyama, Tokyo (JP); Tsutomu Karimata, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 0 days.

(21) Appl. No.: 14/257,071

(22) Filed: Apr. 21, 2014

(65) Prior Publication Data

US 2014/0312227 A1   Oct. 23, 2014

(30) Foreign Application Priority Data

Apr. 22, 2013 (JP) .................................. 2013-089124
Jun. 10, 2013 (JP) .................................. 2013-122042

(51) Int. Cl.
| | |
|---|---|
| *H01J 37/26* | (2006.01) |
| *G01N 23/22* | (2006.01) |
| *H01J 37/09* | (2006.01) |
| *H01J 37/16* | (2006.01) |
| *H01J 37/20* | (2006.01) |
| *H01J 37/285* | (2006.01) |
| *G01N 21/95* | (2006.01) |

(52) U.S. Cl.
CPC ............ *G01N 23/2204* (2013.01); *H01J 37/09* (2013.01); *H01J 37/16* (2013.01); *H01J 37/20* (2013.01); *H01J 37/285* (2013.01); *G01N 21/9501* (2013.01); *H01J 2237/022* (2013.01); *H01J 2237/0264* (2013.01); *H01J 2237/1501* (2013.01); *H01J 2237/166* (2013.01); *H01J 2237/2007* (2013.01); *H01J 2237/20221* (2013.01); *H01J 2237/20278* (2013.01)

(58) Field of Classification Search
USPC .......... 250/305, 306, 307, 308, 309, 310, 311
See application file for complete search history.

(56) References Cited

U.S. PATENT DOCUMENTS

| | | | |
|---|---|---|---|
| 6,265,719 B1 | 7/2001 | Yamazaki et al. | |
| 2002/0028399 A1 | 3/2002 | Nakasuji et al. | |
| 2008/0203300 A1* | 8/2008 | Suzuki ........................ | 250/311 |
| 2013/0126727 A1* | 5/2013 | Jozwiak et al. ............... | 250/305 |
| 2013/0228684 A1 | 9/2013 | Hatakeyama et al. | |

FOREIGN PATENT DOCUMENTS

| | | |
|---|---|---|
| JP | 11-132975 A | 5/1999 |
| JP | 2005-235777 A | 9/2005 |
| JP | 2007-48686 A | 2/2007 |

(Continued)

*Primary Examiner* — Nicole Ippolito
(74) *Attorney, Agent, or Firm* — Pearne & Gordon LLP

(57) ABSTRACT

An inspection apparatus capable of facilitating reduction in cost of the apparatus is provided. The inspection apparatus includes: beam generation means for generating any of charged particles and electromagnetic waves as a beam; a primary optical system that guides the beam into an inspection object held on a movable stage in a working chamber and irradiates the inspection object with the beam; a secondary optical system that detects secondary charged particles occurring from the inspection object; and an image processing system that forms an image on the basis of the detected secondary charged particles. The inspection apparatus further includes: a linear motor that drives the movable stage; and a Helmholtz coil that causes a magnetic field for canceling a magnetic field caused by the linear motor when the movable stage is driven.

2 Claims, 38 Drawing Sheets

(56) References Cited

FOREIGN PATENT DOCUMENTS

| JP | 2009-004161 A | 1/2009 |
| JP | 2009-087893 A | 4/2009 |
| JP | 2010-056270 A | 3/2010 |
| WO | 02/01596 A1 | 1/2002 |

* cited by examiner

INSPECTION APPARATUS

BACKGROUND OF THE INVENTION

1. Field of the Invention

The present invention (first aspect) relates to an inspection apparatus that inspects defects of a pattern formed on a surface of an inspection object, and specifically, to an inspection apparatus that captures secondary charged particles varying properties of a surface of an inspection object, forms image data, and inspects a pattern and the like formed on the surface of the inspection object on the basis of the image data at a high throughput, and an inspection method.

Furthermore, the present invention (second aspect) relates to an inspection apparatus that inspects a sample surface using an electron beam and, particularly, to an inspection apparatus that can inspect sample surfaces (front, rear and outer peripheral surfaces) at high sensitivity using an electron beam while preventing foreign matters from adhering to the sample surfaces.

2. Description of the Related Art (First Aspect)

A conventional semiconductor inspection apparatus supports a 100 nm design rule and technologies. Samples as inspection objects are wafers, exposure masks, EUV masks, NIL (nanoimprint lithography) masks, and substrates; the samples have thus been varying. At present, apparatuses and technologies that support a design rule for samples with 5 to 30 nm are required. That is, it is required to support L/S (line/space) or hp (half pitch) nodes of 5 to 30 nm in a pattern. In the case where an inspection apparatus inspects such samples, it is required to achieve a high resolution.

Here, "samples" are exposure masks, EUV masks, nanoimprint mask (and templates), semiconductor wafers, substrates for optical elements, substrates for optical circuits and the like. The samples include samples with patterns and samples without patterns. The samples with patterns include samples with asperities and samples without asperities. Patterns are formed of different materials on the samples without asperities. The samples without patterns include samples coated with an oxide film and samples with no oxide film.

Problems of the conventional inspection apparatuses are summarized as follows.

A first problem is insufficient resolution and throughput. In a conventional art of a mapping optical system, the pixel size is about 50 nm, and the aberration is about 200 nm. Achievement of further high resolution and improvement of the throughput require reduction in aberration, reduction in energy width of irradiation current, a small pixel size, and increase in current intensity.

A second problem is that, in the case of SEM inspection, the finer the structure to be inspected, the more serious the throughput problem is. This problem occurs because the resolution of an image is insufficient if a smaller pixel size is not used. These points are caused because the SEM forms an image and inspects defects on the basis of edge contrast. For instance, in the case of a pixel size of 5 nm and 200 MPPS, the throughput is approximately 6 hr/cm$^2$. This example takes a time 20 to 50 times as long as the time of mapping projection. The time is unrealistic for inspection.

(Second Aspect)

The electron beam inspection apparatus is used for irradiating a surface of a sample, such as a semiconductor wafer, with a primary electron beam, detecting secondary electrons emitted from the sample surface or mirror electrons to acquire an image of a sample surface, and performing inspections for defects on the sample surface, pattern evaluation or the like on the basis of the image.

A sample, such as a semiconductor wafer, is conveyed in an atmosphere and vacuum for inspection or processing. It has been known that if, during such conveyance, foreign matters, such as particles having a diameter of e.g. 100 nm or less, can be prevented from adhering to a sample surface and adherence of foreign matters that are to be killer defects on a pattern to the sample surface can be reduced, yields are largely improved. If killer defects are left as they are in processes of manufacturing semiconductors or LSIs, wiring widths and insulation resistance values become insufficient and significantly degrade performance. Accordingly, some processes, such as correction or failure determination, are required to address the killer defects.

In particular, an electron beam inspection apparatus can achieve highly accurate measurement and inspection results by reducing adhesion of foreign matters, such as particles generated by the apparatus, to a sample surface. Thus, a process of adhesion of foreign matters to a sample surface can be identified and improvement can be achieved. Accordingly, for instance, defects can be reduced in an exposure process.

Conventionally, in relation to conveyance of a sample, measures have been taken that prevent foreign matters, such as particles, from being generated as much as possible. For instance, for an atmosphere conveyance system for a sample, a high-functioning filter and a mini-environment having a downflow are provided. The atmosphere conveyance system is stored in the mini-environment. Furthermore, a sample is electrically neutralized by a neutralization device, thereby suppressing adhesion of particles to the sample surface. In a vacuum conveyance system for a sample, variation in pressure is controlled by a load lock. However, it is typically difficult to reduce fine-sized foreign matters, such as particles having a diameter of 100 nm or less.

In view of such problems, the applicant has already proposed a method of removing foreign matters on a sample surface; the method detects foreign matters on a sample surface, moves the sample in a horizontal direction, charges an absorption electrode arranged facing and close to the sample surface in the polarity different from the charging polarity of the foreign matters, and electrostatically absorbs approaching foreign matters onto the absorption electrode to thereby detect the foreign matters on the sample surface, and removes the foreign matters on the sample surface when the foreign matters are detected (see Japanese Patent Laid-Open No. 2009-4161 (Patent Document 4)).

Furthermore, a particle monitor has been proposed that causes a dust collecting electrode to actively collect particles suspended in a plasma processing apparatus, accumulates the particles using a quadrupole linear trap or the like to a specific site, and electrically detects the particles, or detects the particles using laser scattered light (see Japanese Patent Laid-Open No. 2010-56270 (Patent Document 5)).

As the design rule for LSIs has significantly become fine, the sizes of foreign matters, which should be prevented from adhering to a sample surface, become finer. Adhesion of foreign matters, such as particles generated by operation of an inspection apparatus and the like, has become a significant problem. Measures against the problem are required to be taken.

However, it is difficult for a conventional foreign matter adhesion preventing mechanism to prevent fine foreign matters, such as particles having a diameter of e.g. 100 nm or less, from adhering to a sample surface. In particular, in the case where a sample is arranged on a stage in a vacuum chamber or the like and the sample surface is inspected by an electron beam inspection apparatus, no consideration has been given to suppression of occurrence of foreign matters, such as particles from the apparatus itself.

The conventional art described in Patent Document 4 detects that foreign matters adhere to a sample surface, and subsequently removes the foreign matters from the sample surface, but cannot prevent the foreign matters from adhering to the sample surface. In the conventional art described in Patent Document 5, the dust collecting electrode is provided on, for instance, a distal end of the particle monitor, for collecting particles suspended in the plasma processing apparatus, but cannot prevent the particles from adhering to the sample surface.

Furthermore, in some cases, static electricity caused by an air flow when the vacuum chamber is evacuated charges foreign matters, such as particles, remaining in the vacuum chamber, the charged foreign matters, such as particles, are electrostatically attracted to the sample surface, which is to be inspected, thereby contaminating the sample surface. As to the conventional vacuum chamber used for inspecting a sample surface, no measures are taken against electrostatically attracting foreign matters, such as particles, remaining in the vacuum chamber to the sample surface, and such residues are removed by cleaning. It is thus strongly demanded that residues incapable of being removed by cleaning in the vacuum chamber be prevented from adhering to the sample surface.

The present invention has been made in view of the problems. A first object thereof is to provide a foreign matter adhesion preventing method that can prevent foreign matters from adhering to a sample surface as much as possible, and an electron beam inspection apparatus that can inspect a sample surface using an electron beam while preventing foreign matters from adhering to the sample surface as much as possible.

Furthermore, Japanese Patent Laid-Open No. 2005-235777 (Patent Document 6) describes a sample surface observation method using an electron beam inspection apparatus. This conventional method uses shades (gradation difference) in an image that occurs at portions of open defects and lacking defects. At the portions with defects including open defects and lacking defects, shades (gradation difference), which do not ordinarily occur in a normal portion, appear in an image. Accordingly, the conventional method adopts procedures that compare a wafer surface image acquired from a surface of a semiconductor wafer with an ordinary surface image (of a sample without defects), and determines that the portion concerned is an open defect or a lacking defect if shades, which do not ordinarily appear, are identified.

However, the observation method disclosed in Patent Document 6 has a problem in that the gradation difference in a portion to be observed in some cases of the structure, material and the like of a sample as an observation object is originally small, and it is sometimes difficult to detect lacking defects and open defects.

Furthermore, particularly on open defects, an image of a portion where open defects exist sometimes becomes thicker (more black) and sometimes becomes thinner (more white) than an image of a normal portion. There is thus a problem in that it is significantly difficult to detect defects and classify the types of defects.

In view of such a problem, the inventors have repeatedly discussed detection of defects on a wiring structure for the sake of providing a sample surface observation method that acquires a sample surface image where the gradation difference between a defect portion and a normal portion is large and the difference shades of gray is clear, and can easily detect defects. As a result, the inventors have come to regard that the problem of the sample surface observation method disclosed in Patent Document 6 resides in detection of lacking defects and open defects in the same condition at the same time, and proposed a novel sample surface observation method (see Japanese Patent Laid-Open No. 2009-87893 (Patent Document 7)).

Patent Document 7 discloses a sample surface observation method that irradiates, with an electron beam, a sample surface where wiring including insulation material and conductive material is formed, and detects electrons including information on the structure of the sample surface, thereby acquiring a sample surface image to observe the sample surface. In a situation where the insulation material and the conductive material have the same luminance in the sample surface image, this method irradiates the sample surface with an electron beam to thereby easily and securely detect portions other than the insulation material and the conductive material, and further detects, as open defects on the sample surface, points in the sample surface image where the insulation material and the conductive material have different luminances to thereby easily and securely detect the open defects.

Furthermore, Patent Document 7 discloses a sample surface observation method that irradiates a sample surface with an electron beam in a condition where the difference in luminance between insulation material and conductive material in a sample surface image is the maximum, and acquires a sample surface image allowing easy discrimination from peripheral portions of lacking defects to achieve easy and secure detection of the lacking defects, and moreover, sets the condition where the difference in luminance is the maximum in a mirror electron region where electrons including information on the sample surface structure become mirror electrons, thereby allowing lacking defects to be effectively detected.

Patent Document 1: International Publication No. WO2002/001596

Patent Document 2: Japanese Patent Laid-Open No. 2007-48686

Patent Document 3: Japanese Patent Laid-Open No. H11-132975

Patent Document 4: Japanese Patent Laid-Open No. 2009-4161

Patent Document 5: Japanese Patent Laid-Open No. 2010-56270

Patent Document 6: Japanese Patent Laid-Open No. 2005-235777

Patent Document 7: Japanese Patent Laid-Open No. 2009-87893

SUMMARY OF THE INVENTION (First Aspect)

The conventional inspection apparatus adopts a drive motor made of nonmagnetic material as a drive source for moving, in XY directions, a stage on which an inspection object (sample) is mounted in order to prevent an electron beam from being affected by a magnetic field. However, the drive motor made of nonmagnetic material is expensive (e.g., more expensive than a linear motor), which causes a problem in that it is difficult to reduce the cost of the apparatus.

The present invention has been made in view of the problems. It is an object of the present invention to provide an inspection apparatus that can reduce the cost of the apparatus.

(Second Aspect)

Also in the conventional inspection apparatus, it is difficult to completely prevent foreign matters (particles) from adhering to a sample surface. Thus, further improvement of a technique for preventing foreign matters from adhering has been demanded.

The present invention has been made in view of the problems, and has an object to provide an inspection apparatus that can further reduce adhesion of foreign matters to a sample surface in comparison with the conventional art.

(First Aspect)

An inspection apparatus of the present invention includes: beam generation means for generating any of charged particles and electromagnetic waves as a beam; a primary optical system that guides the beam into an inspection object held on a movable stage in a working chamber and irradiates the inspection object with the beam; a secondary optical system that detects secondary charged particles occurring from the inspection object; an image processing system that forms an image on the basis of the detected secondary charged particles; a linear motor that drives the movable stage; and a Helmholtz coil that causes a magnetic field for canceling a magnetic field caused by the linear motor when the movable stage is driven.

The linear motor is thus adopted as a drive source for driving the movable stage. This adoption can facilitate reduction in cost of the apparatus. In this case, the magnetic field caused by the linear motor when the movable stage is driven is canceled by the magnetic field caused by the Helmholtz coil. Accordingly, adverse effects of the magnetic field caused by the linear motor to the beam including the charged particles or the electromagnetic waves can be suppressed.

The inspection apparatus of the present invention may further includes: current detection means for detecting drive current for driving the linear motor; and magnetic field control means for controlling an intensity of a magnetic field caused by the Helmholtz coil according to the drive current detected by the current detection means.

Thus, the intensity of the magnetic field caused by the Helmholtz coil is controlled according to the drive current for driving the linear motor. Accordingly, the intensity of the magnetic field caused by the Helmholtz coil can be appropriately controlled so as to cancel the magnetic field caused by the linear motor.

The inspection apparatus of the present invention may further include position detection means for detecting a position of the movable stage, wherein the magnetic field control means controls the intensity of the magnetic field caused by the Helmholtz coil, according to the drive current detected by the current detection means and the position detected by the position detection means.

Thus, the intensity of the magnetic field caused by the Helmholtz coil is controlled according to the drive current for driving the linear motor and the position of the movable stage. Accordingly, the intensity of the magnetic field caused by the Helmholtz coil can be appropriately controlled so as to cancel the magnetic field caused by the linear motor.

(Second Aspect)

An inspection apparatus of the present invention is an inspection apparatus for inspecting a sample surface using an electron beam, including: an electron beam source; a primary electron optical system that includes a primary system lens and guides the electron beam emitted from the electron beam source; a stage on which a sample to be irradiated with primary electrons guided by the primary electron optical system is arranged; a secondary electron optical system that includes a secondary system lens and guides secondary charged particles emitted from the surface of the sample due to irradiation with the electron beam; a detector that detects the secondary charged particles guided by the secondary electron optical system; a gap control plate that is arranged above the stage so as to cover the surface of the sample arranged on the stage, and internally includes a through hole allowing the electron beam to pass therethrough; and a cover member that is attached to a condenser lens arranged in the through hole in the secondary system lens, and blocks a gap between the through hole and the condenser lens in view of a direction perpendicular to the gap control plate.

Accordingly, the gap (the gap viewed in a direction perpendicular to the gap control plate) between the through hole of the gap control plate and the condenser lens can be blocked by the cover member. For instance, the outer diameter of the cover member is configured to be larger than the through hole of the gap control plate by 6 to 20 mm. Such a cover member is thus provided, which can reduce adhesion of foreign matters (particles) to the sample surface through the gap between the through hole of the gap control plate and the condenser lens.

In the inspection apparatus of the present invention, in view of a direction parallel to the gap control plate, a gap may be provided between the gap control plate and the cover member.

Thus, the gap (the gap viewed in the direction parallel to the gap control plate) is provided between the gap control plate and the cover member. That is, the gap control plate and the cover member do not in contact with each other (noncontact). This configuration can prevent vibrations of the gap control plate from being transmitted to the condenser lens. Accordingly, an image is prevented from being distorted by adverse effects of the vibrations of the gap control plate.

In the inspection apparatus of the present invention, the gap between the surface of the sample and the gap control plate in view of a direction parallel to the gap control plate has a width ranging from 5 to 30 mm. Accordingly, the electric field distribution is stable, which can prevent charged foreign matters (particles) from being attracted to the sample surface.

In the inspection apparatus of the present invention, a support pillar may be attached to a ceiling surface of a vacuum chamber, and the gap control plate may be attached in the vacuum chamber via the support pillar.

Thus, the support pillar is attached to the ceiling surface of the vacuum chamber, and the gap control plate is attached in the vacuum chamber via the support pillar. Accordingly, the potential can be changed only by means of the gap control plate to control the electric field. A space through which a hand can be put into the vacuum chamber can be secured by detaching the gap control plate. Accordingly, maintenance is improved. For instance, an objective lens can be detachable. Furthermore, maintenance and cleaning of devices on the mirror plate can be allowed.

According to the present invention (first aspect), the linear motor can be adopted as the drive source for driving the movable stage, thereby allowing the cost of the apparatus to be reduced.

According to the present invention (second aspect), the cover member is provided, which can reduce adhesion of foreign matters (particles) to the sample surface.

BRIEF DESCRIPTION OF THE DRAWINGS

FIG. 5A is a side view. FIG. 5B is a sectional view taken along line E-E of FIG. 5A;

Figure 1:
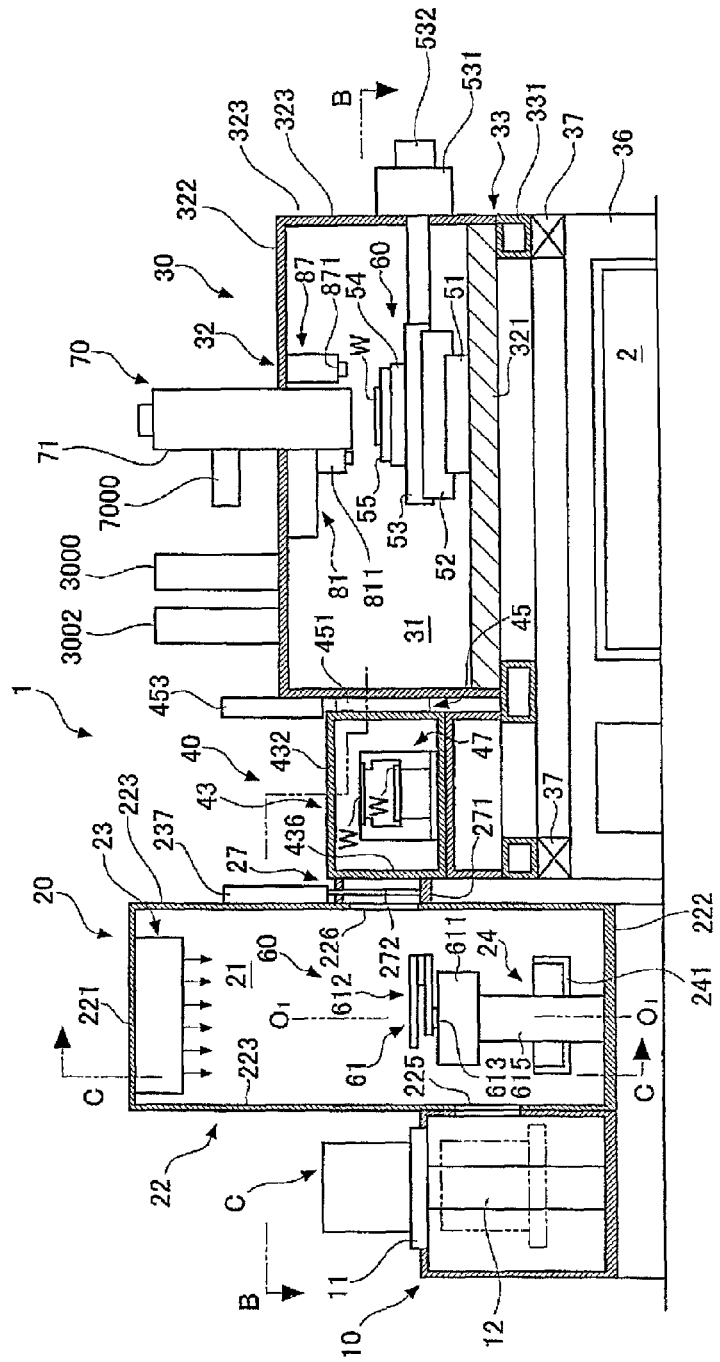
FIG. 1 is an elevational view showing main configuration components in an inspection apparatus according to an embodiment of the present invention taken along line A-A of FIG. 2.

DETAILED DESCRIPTION OF THE PREFERRED EMBODIMENTS (First Aspect)

Referring to the drawings, embodiments of the present invention (first aspect) will hereinafter be described on a semiconductor inspection apparatus that inspects a substrate, or a wafer, on which a pattern is formed, as an inspection object. Note that the following embodiments are examples of an inspection apparatus and an inspection method of the present invention. This invention is not limited to the examples.

Figure 2A:
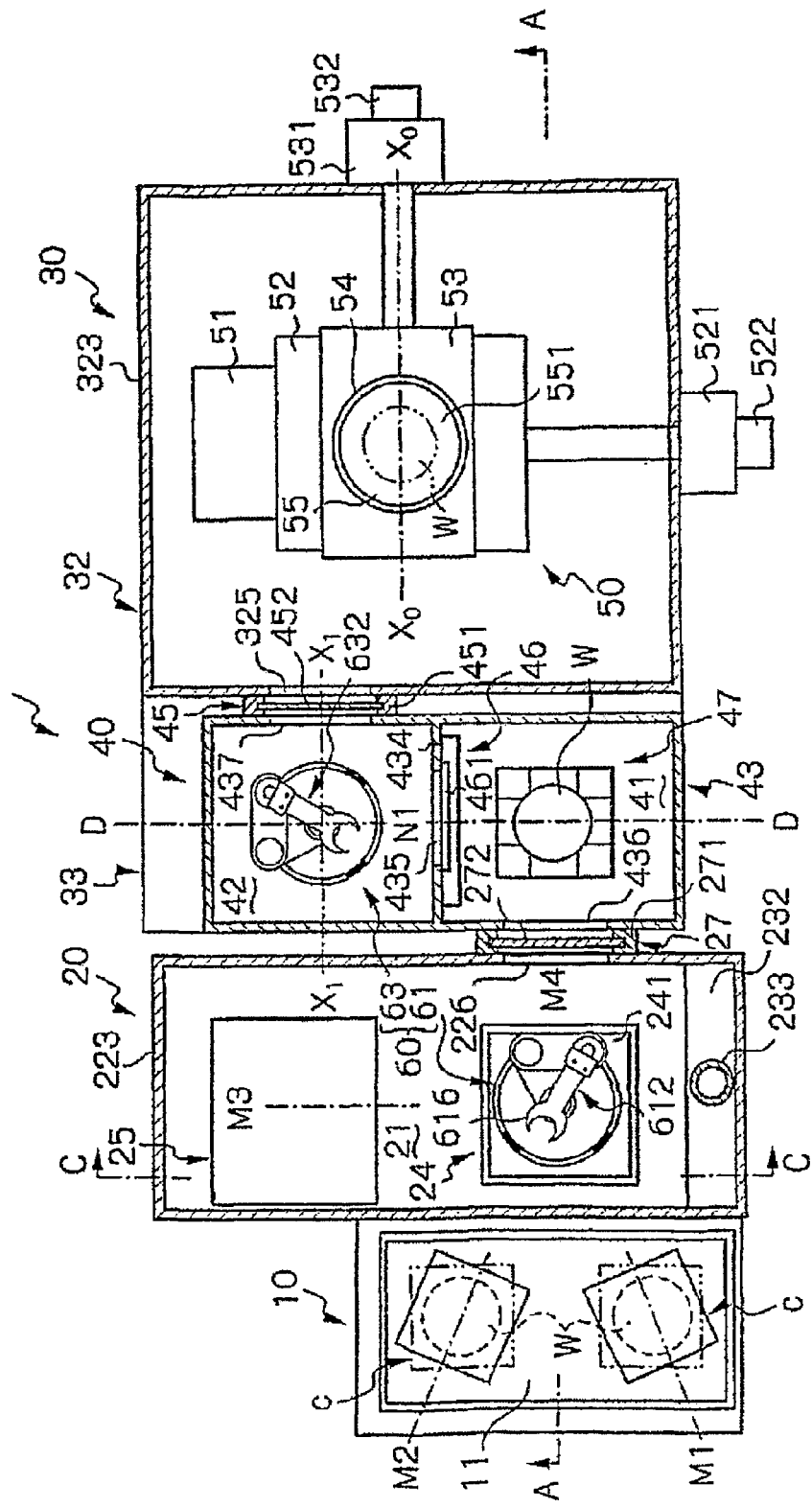
FIG. 2A is a plan view of the main configuration components of the inspection apparatus shown in FIG. 1 taken along line B-B of FIG. 1.

FIGS. 1 and 2A respectively show an elevational view and a plan view of main configuration components of a semiconductor inspection apparatus 1 of this embodiment.

The semiconductor inspection apparatus 1 of this embodiment includes: a cassette holder 10 that holds a cassette storing multiple wafers; a mini-environment device 20; a main housing 30 that defines a working chamber; a loader housing 40 that is disposed between the mini-environment device 20 and the main housing 30 to define two loading chambers; a loader 60 that loads a wafer from the cassette holder 10 onto a stage device 50 disposed in the main housing 30; an electronic optical device 70 attached to a vacuum housing; an optical microscope 3000; and a scanning electron microscope (SEM) 3002. These components are disposed in a positional relationship as shown in FIGS. 1 and 2A. The semiconductor inspection apparatus 1 further includes: a precharge unit 81 disposed in the vacuum main housing 30; a potential application mechanism 83 (shown in FIG. 14) that applies a potential to a wafer; an electron beam calibration mechanism 85; and an optical microscope 871 that configures an alignment controller 87 for positioning the wafer on the stage device. The electronic optical device 70 includes a lens tube 71 and a light source tube 7000. The internal configuration of the electronic optical device 70 will be described later.

Cassette Holder

The cassette holder 10 holds a plurality of (two in this embodiment) cassettes c (e.g., closed cassettes, such as SMIF and FOUP, made by Asyst technologies Inc.) each of which stores a plurality of (e.g., 25) wafers in a state of being arranged in the vertical direction in horizontal orientation. In the case of conveying the cassette by a robot or the like and automatically loading the cassette to the cassette holder 10, a cassette holder suitable to this loading manner is adopted. In the case of manual loading, a cassette holder that has an open cassette structure suitable to this loading manner is adopted. Any of the holders can be selected and installed. In this embodiment, the cassette holder 10 is in conformity with a system of automatically loading the cassette c, and includes, for instance, a lifting table 11, and a lifting mechanism 12 that vertically lifts and lowers the lifting table 11. The cassette c can be automatically set onto the lifting table in a state indicated by a chain line in FIG. 2A. After the setting, the cassette is automatically turned to a state indicated by a solid line in FIG. 2A to be aligned with the turning axis of a first conveyance unit in the mini-environment device. The lifting table 11 is lowered to a state indicated by a chain line in FIG. 1. Thus, the cassette holder used in the case of automatic loading or the cassette holder used in the case of manual loading may be appropriately selected among cassettes having publicly known structures. Accordingly, detailed description on the structure and functions of the cassette holder is omitted.

Figure 2B:
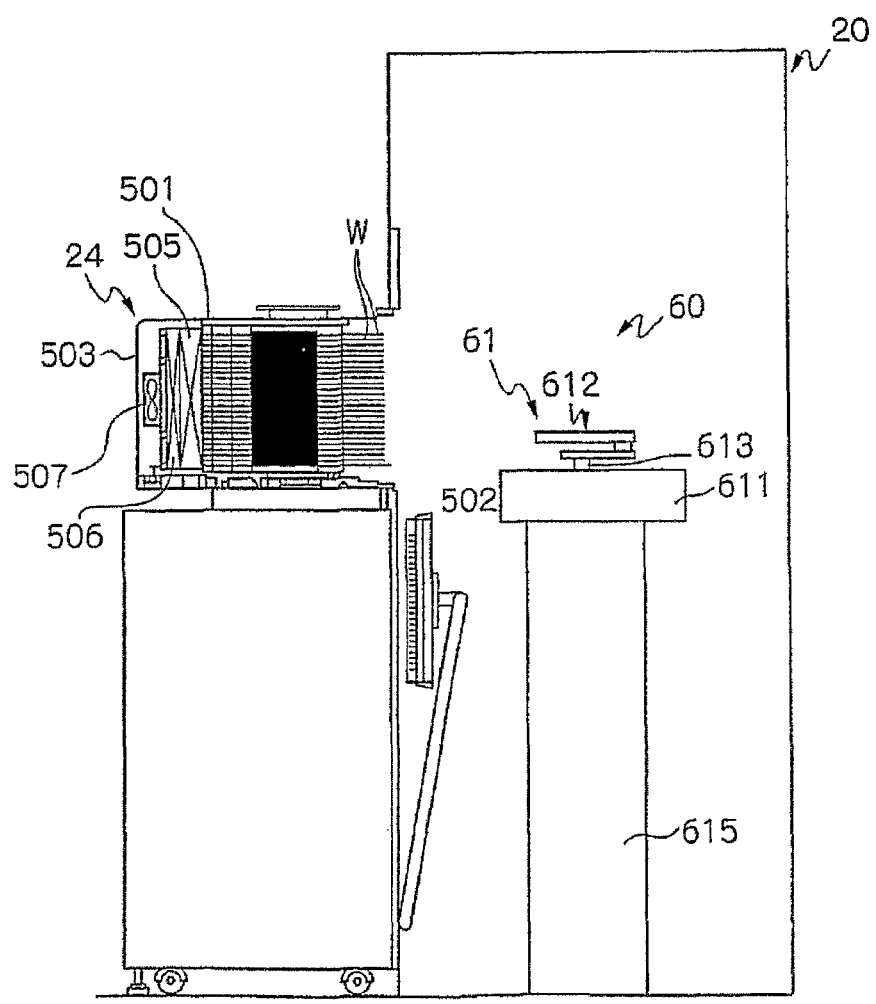
FIG. 2B is a schematic sectional view showing another embodiment of a substrate installation device of the inspection apparatus of the embodiment of the present invention.

In another embodiment, as shown in FIG. 2B, a plurality of 300 mm substrates are stored in groove pockets (not shown) fixed in a box main body 501 in a state of being accommodated, and then conveyed or stored. The substrate conveyance box 24 includes: a box main body 501 having a shape of a rectangular cylinder; a substrate conveyance door 502 that is connected to the box main body 501 and a device of automatically opening and closing the substrate conveyance door and can mechanically open and close an opening on a side of the box main body 501; a cover 503 that is disposed opposite to the opening and covers the opening through which filters and a fan motor is attached and detached; groove pockets (not shown) for storing substrates W; an ULPA filter 505; a chemical filter 506; and a fan motor 507. In this embodiment, the substrate is carried in and out by a robotic first conveyance unit 612 of the loader 60.

The substrates, or wafers, stored in the cassette c are to be inspected. The inspection is performed after or in a process on a wafer, in semiconductor manufacturing processes. More specifically, substrates, which are wafers, subjected to a film forming process, CMP, ion injection, etc., wafers on which wiring patterns are formed, or wafers on which wiring patterns have not been formed yet, are stored in the cassette. The wafers stored in the cassette c are arranged vertically separated and in parallel with each other. Accordingly, an arm of the after-mentioned first conveyance unit is configured to be vertically moved so as to hold the wafer at any position by the first conveyance unit.

Mini-Environment Apparatus

Figure 3:
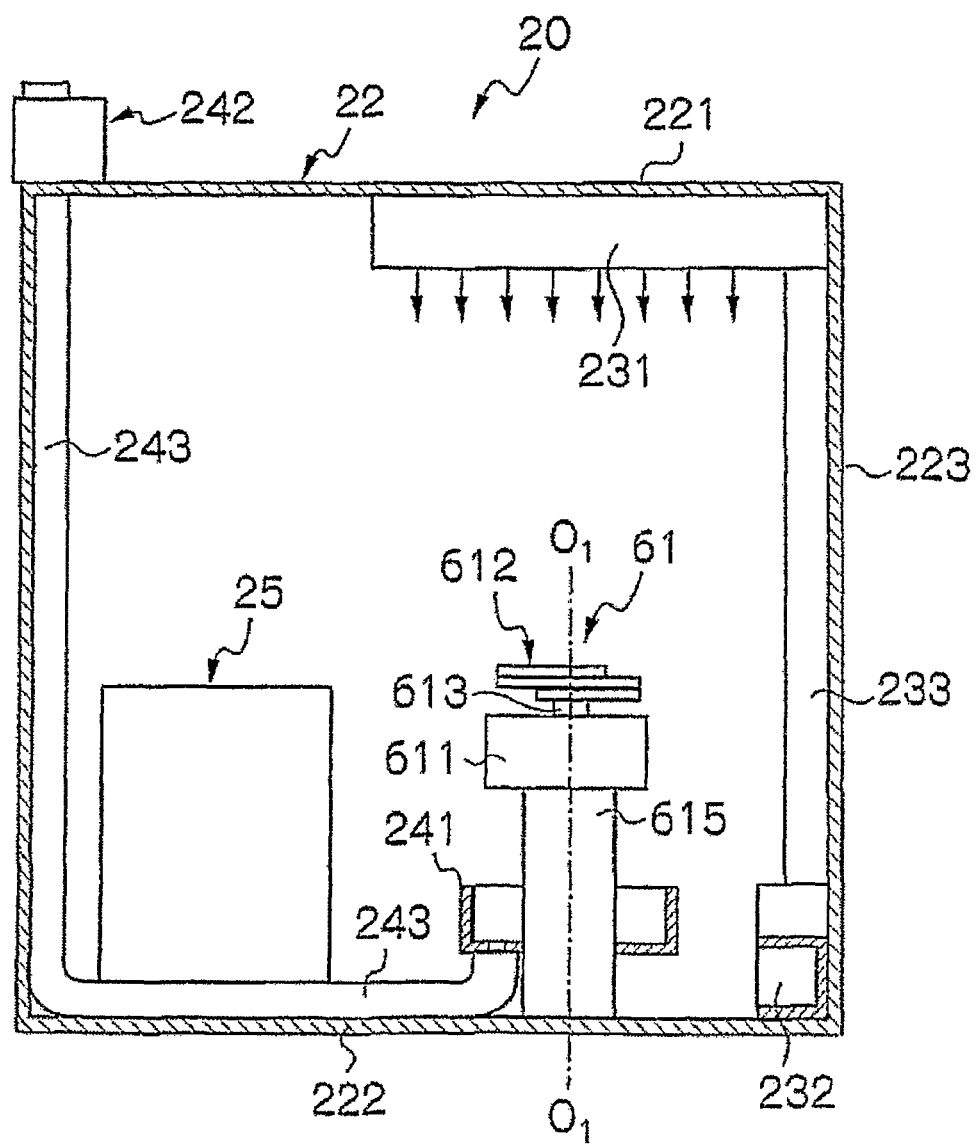
FIG. 3 is a sectional view showing a mini-environment device of FIG. 1 taken along line C-C.

In FIGS. 1 to 3, the mini-environment device 20 includes: a housing 22 that defines an atmosphere-controlled mini-environment space 21; a gas circulator 23 that circulates gas, such as cleaned air, to control an atmosphere in the mini-environment space 21; an evacuator 24 that collects and evacuates a part of air supplied in the mini-environment space 21; and a prealigner 25 that is disposed in the mini-environment space 21 and roughly positions a substrate as an inspection object, i.e., a wafer.

The housing 22 includes a top wall 221, a bottom wall 222, and surrounding walls 223 that surround the periphery, and thus has a structure that isolates the mini-environment space 21 from the outside. As shown in FIG. 3, in order to control the atmosphere in the mini-environment space, the gas circulator 23 includes: a gas supply unit 231 that is attached to the top wall 221 in the mini-environment space 21, cleans the gas (air in this embodiment), and flows the cleaned air as a laminar flow directly downward through one or more gas outlet (not shown); a collection duct 232 that is disposed on the bottom wall 222 in the mini-environment space, and collects the air having flown down toward the bottom; and a pipe 233 that communicates with the collection duct 232 and the gas supply unit 231, and returns the collected air to the gas supply unit 231. In this embodiment, the gas supply unit 231 captures about 20% of the air to be supplied, from the outside of the housing 22 and cleans the captured air. However, the ratio of the air captured from the outside is arbitrarily selected. The gas supply unit 231 includes a HEPA or ULPA filter that has a publicly known structure for creating cleaned air. The downward laminar flow of the cleaned air, i.e., the downflow, is supplied mainly so as to flow over a conveyance surface of the after-mentioned first conveyance unit disposed in the mini-environment space 21. The flow prevents dust that may possibly be caused by the conveyance unit from adhering to the wafer. Accordingly, the downflow nozzle is not necessarily disposed at a position near the top wall as shown in the figure. The nozzle may be disposed at any position above the conveyance surface of the conveyance unit. The air is not necessarily flown over the entire surface of the mini-environment space. In some cases, an ion wind is used as the cleaned air to secure cleanness. A sensor for observing the cleanness may be provided in the mini-environment space, and the apparatus can be shut down when the cleanness is degraded. A gateway 225 is formed at a portion of the surrounding wall 223 of the housing 22 that is adjacent to the cassette holder 10. A shutter device having a publicly known structure may be provided adjacent to the gateway 225 to shut the gateway 225 from a side of the mini-environment device. The downflow of the laminar flow formed adjacent to the wafer may have, for instance, a flow rate of 0.3 to 0.4 m/sec. The gas supply unit may be provided outside of the mini-environment space, instead of the inside of this space.

The evacuator 24 includes: an intake duct 241 disposed at a position below a wafer conveyance surface of the conveyance unit, at a lower part of the conveyance unit; a blower 242 disposed outside of the housing 22; and a pipe 243 that communicates with the intake duct 241 and the blower 242. The evacuator 24 sucks, into intake duct 241, the gas that flows around the conveyance unit and may contain dust that may possibly be caused by the conveyance unit, and evacuates the gas out of the housing 22 through the pipes 243 and 244 and the blower 242. In this case, the gas may be evacuated into an exhaust pipe (not shown) drawn adjacent to the housing 22.

The aligner 25 disposed in the mini-environment space 21 optically or mechanically detects an orientation flat (a flat part formed at the circumference of the circular wafer) formed at the wafer or one or more V-shaped notches formed at the circumference of the wafer, and preliminarily positions the wafer in the turning direction about the axis O-O of the wafer at an accuracy of about ±1 degree. The prealigner configures a part of a mechanism of determining the coordinates of an inspection object according to the invention described in claims, and functions to roughly position the inspection object. The prealigner itself may be a prealigner having a publicly known structure. Accordingly, description on the structure and operations is omitted.

Although not shown, a collection duct for the evacuator may be provided also at the lower part of the prealigner to evacuate air including dust ejected from the prealigner to the outside.

Main Housing

In FIGS. 1 and 2A, the main housing 30, which defines a working chamber 31, includes a housing main body 32. The housing main body 32 is supported by a housing supporter 33 mounted on a vibration isolating device, or a vibration isolator 37, disposed on a base frame 36. The housing supporter 33 includes a frame structure 331 configured into a rectangular shape. The housing main body 32, which is disposed and fixed onto the frame structure 331, includes a bottom wall 321 mounted on the frame structure, a top wall 322, surrounding walls 323 that are connected to the bottom wall 321 and the top wall 322 and surround the periphery, and isolates the working chamber 31 from the outside. In this embodiment, the bottom wall 321 is made of steel plates having a relatively large thickness not to cause distortion due to the weight of a device, such as a stage device, mounted on this wall. However, the bottom wall may have another structure. In this embodiment, the housing main body and the housing supporter 33 are configured to have rigid structures. The configuration allows the vibration isolator 37 to prevent vibrations of a floor on which the base frame 36 is installed from being transferred to the rigid structures. A gateway 325 through which a wafer is carried in and out is formed at a surrounding wall adjacent to the after-mentioned loader housing among the surrounding walls 323 of the housing main body 32.

The vibration isolator may be an active isolator having an air spring, a magnetic bearing or the like, or a passive isolator including these components. Each of the isolators may be an isolator having a publicly known structure. Accordingly, description on the structure and operations is omitted. The atmosphere in the working chamber 31 is kept in a vacuum atmosphere by a vacuum device (not shown) having a publicly known structure. A controller 2 that controls the operations of the entire apparatus is disposed at the bottom of the base frame 36.

Loader Housing

Figure 4:
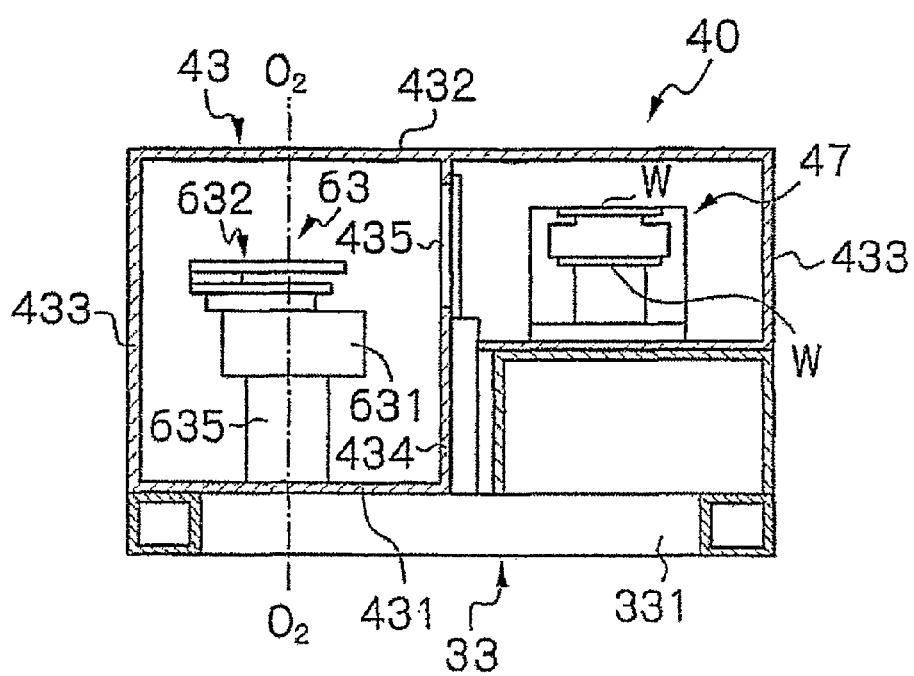
FIG. 4 is a diagram showing a loader housing of FIG. 1 taken along line D-D of FIG. 2.

In FIGS. 1, 2A and 4, the loader housing 40 includes a housing main body 43 that defines a first loading chamber 41 and a second loading chamber 42. The housing main body 43 includes a bottom wall 431, a top wall 432, surrounding walls 433 that surround the periphery, and a partition wall 434 that separates the first loading chamber 41 and the second loading chamber 42 from each other. The structure can separate both the loading chambers from the outside. An opening, or a gateway 435, through which a wafer is exchanged between both the loading chambers is formed at the partition wall 434. Gateways 436 and 437 are formed at portions of the surrounding walls 433 adjacent to the mini-environment device and the main housing. The housing main body 43 of the loader housing 40 is mounted on the frame structure 331 of the housing supporter 33, and supported by this structure. Accordingly, vibrations of the floor are not transmitted to loader housing 40 either. The gateway 436 of the loader housing 40 and the gateway 226 of the housing 22 of the mini-environment device match with each other. A shutter device 27 that selectively blocks communication between the mini-environment space 21 and the first loading chamber 41 is provided at the matching portion. The shutter device 27 includes: a seal member 271 that surrounds the gateways 226 and 436 and is in close contact with and fixed to the side wall 433; a door 272 cooperates with the seal member 271 to prevent the air from flowing through the gateways; and a drive device 273 that moves the door. The gateway 437 of the loader housing 40 and the gateway 325 of the housing main body 32 match with each other. A shutter device 45 is provided that selectively blocks communication between the second loading chamber 42 and the working chamber 31. The shutter device 45 includes: a seal member 451 that surrounds the gateways 437 and 325 and is in close contact with and fixed to the respective side walls 433 and 323; a door 452 that cooperates with seal member 451 to block communication of air through the gateways; and a drive device 453 that moves the door. Furthermore, a shutter device 46 that closes the door 461 to selectively seal and block communication between the first and second loading chambers is provided at an opening formed at the partition wall 434. In closed states, the shutter devices 27, 45 and 46 can hermetically seal the corresponding chambers. These shutter devices may be devices having a publicly known structure. Accordingly, detailed description on the structure and operations is omitted. The method of supporting the housing 22 of the mini-environment device 20 is different from the method of supporting the loader housing. In order to prevent vibrations of the floor from being transmitted to the loader housing 40 and the main housing 30 through the mini-environment device, a vibration isolating cushion member is preferably disposed between the housing 22 and the loader housing 40 so as to hermetically surround the gateway.

Figure 5A:
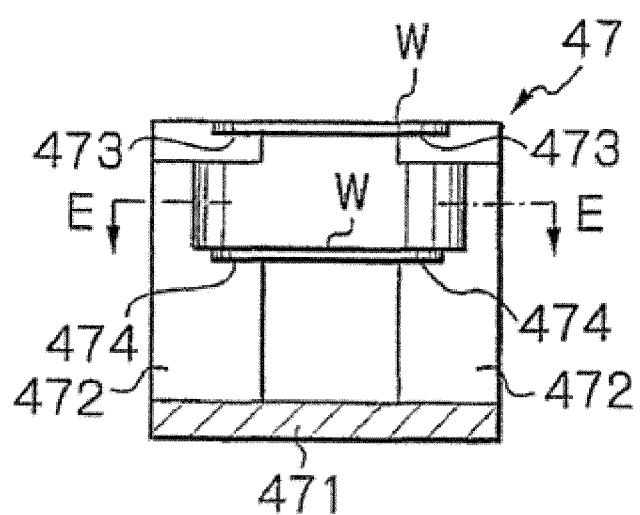
FIGS. 5A and 5B are enlarged views of a wafer rack.
Figure 5B:
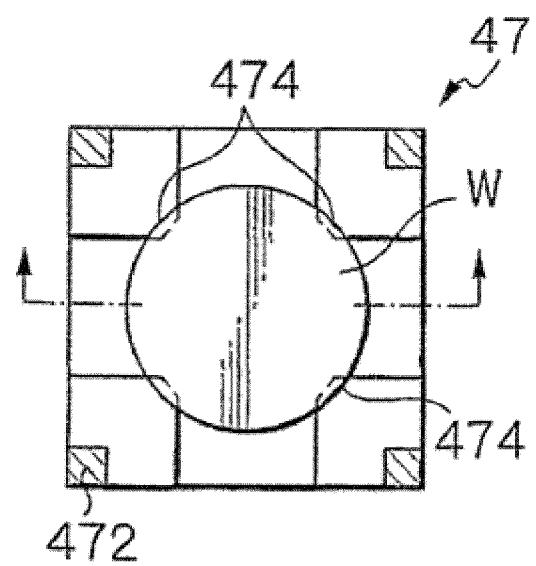

A wafer rack 47 that vertically separates a plurality of (two in this embodiment) wafers and horizontally supports the wafers is arranged in the first loading chamber 41. As shown in FIGS. 5A and 5B, the wafer rack 47 includes pillars 472 fixed in a manner of being separated at the four corners of a rectangular substrate 471 in a state of standing upright. Two stages of supporters 473 and 474 are formed at each pillar 472. The periphery of the wafer W is mounted on the supporters, and thus the wafer is held. The distal ends of the arms of the after-mentioned first and second conveyance units are moved to approach the wafers between the adjacent pillars, and the arms hold the wafers.

The atmospheres of the loading chambers 41 and 42 can be controlled to a high vacuum (a degree of vacuum of $10^{-5}$ to $10^{-6}$ Pa) by a vacuum evacuator (not shown) that has a publicly known structure including a vacuum pump (not shown). In this case, the first loading chamber 41 may be kept in a low vacuum atmosphere and serve as a low vacuum chamber, and the second loading chamber 42 may be kept in a high vacuum atmosphere and serve as a high vacuum chamber. This structure can efficiently prevent wafer from being contaminated. Adoption of the structure can convey a wafer that is stored in the loading chamber and to be subjected to defect inspection at the next time, into the working chamber without delay. Adoption of such a loading chamber can improve the throughput of defect inspection, and achieve a degree of vacuum as high as possible around an electron source, which is required to be stored in a high vacuum state.

A vacuum exhaust pipe and a vent pipe for inert gas (e.g., dry pure nitrogen) (both the pipes are not shown) communicate to first and second loading chambers 41 and 42, respectively. According to this configuration, an atmospheric pressure state in each loading chamber can be achieved by the inert gas vent (inert gas is injected to prevent oxygen gas etc. other than inert gas from adhering to the surface). The device for such inert gas venting may be a device having a publicly known structure. Accordingly, the detailed description is omitted.

Stage Device

The stage device 50 includes: a fixed table 51 disposed on the bottom wall 321 of the main housing 30; a Y table 52 that moves in the Y direction (the direction perpendicular to the sheet of FIG. 1) on the fixed table; an X table 53 that moves in the X direction (the lateral direction in FIG. 1) on the Y table; a turn table 54 that can turn on the X table; and a holder 55 disposed on the turn table 54. A wafer is releasably held on a wafer-mounting surface 551 of the holder 55. The holder may be a holder that has a publicly known structure and can releasably grip a wafer mechanically or according to an electrostatic chuck system. The stage device 50 can highly accurately position a wafer held by the holder on the mounting surface 551, in the X direction, Y direction and the Z direction (the vertical direction in FIG. 1), and further in a direction (θ direction) about an axis perpendicular to the wafer holding surface, with respect to an electron beam emitted from the electronic optical device, by moving the tables using servomotors, encoders and various sensors (not shown). As to the positioning in the Z direction, for instance, the position of the mounting surface on the holder may preferably be slightly adjusted in the Z direction. In this case, the reference position of the mounting surface is detected by a position measuring instrument using fine diameter laser (a laser interferometric distance meter adopting the principle of an interferometer), and the position is controlled by a feedback circuit, not shown. Together with or instead of this control, the position of the notch or the orientation flat of the wafer is measured to detect the planar position and the turning position of the wafer with respect to the electron beam, and the positions are controlled by turning the turn table by a stepping motor or the like capable of fine angle control. In order to prevent dust from occurring in the working chamber as much as possible, servomotors 521 and 531 and encoders 522 and 532 for the stage device are disposed out of the main housing 30. The stage device 50 may be, for instance, a device used in a stepper or the like having a publicly known structure. Accordingly, detailed description on the structure and operations is omitted. The laser interferometric distance meter may be a meter having a publicly known structure. Accordingly, detailed description on the structure and operations is omitted.

The wafer turning position and the X and Y positions with respect to the electron beam are preliminarily input into an after-mentioned signal detection system or an image processing system to allow the signal to be standardized. Furthermore, a wafer chuck mechanism provided in the holder can apply a voltage for chucking a wafer to an electrode of an electrostatic chuck, and press three points on the circumference of the wafer (the points preferably separated by regular intervals in the circumferential direction) for positioning. The wafer chuck mechanism includes two fixed positioning pins, and one pressing crank pin. The clamp pin can achieve automatic chucking and automatic releasing, and configures a conduct part for voltage application.

In this embodiment, the table moving in the lateral direction in FIG. 2A is the X table, and the table moving in the vertical direction is the Y table. Instead, the table moving in the lateral direction may be the Y table, and the table moving in the vertical direction may be the X table in this diagram.

Loader

The loader 60 includes: a robotic first conveyance unit 61 disposed in the housing 22 of the mini-environment device 20; and a robotic second conveyance unit 63 disposed in the second loading chamber 42.

The first conveyance unit 61 includes a multi-axial arm 612 capable of turning about an axis $O_1$-$O_1$ with respect to a driver 611. The multi-axial arm may be an arm having any configuration. In this embodiment, the arm includes three parts attached in a manner capable of turning with respect to each other. A part of the arm 612 of the first conveyance unit 61, i.e., a first part nearest the driver 611, is attached to a shaft 613 that can be turned by a drive mechanism (not shown) that has a publicly known structure and provided in the driver 611. The arm 612 can be turned about the axis $O_1$-$O_1$ by the shaft 613, and extend and contract in the radial direction with respect to the axis $O_1$-$O_1$ as a whole by relative turning between the components. A distal end of a third part of the arm 612 that is most opposite to the shaft 613 is provided with a grip device 616 that has a publicly known structure, such as a mechanical chuck or electrostatic chuck, and grips a wafer. The driver 611 can be vertically moved by a lifting mechanism 615 having a publicly known structure.

The first conveyance unit 61 extends the arm 612 toward any one of directions M1 and M2 of the two cassettes c held by the cassette holder, mounts one wafer stored in the cassette c on the arm or grips the wafer using a chuck (not shown) attached to the distal end of the arm, and picks up the wafer. Subsequently, the arm is contracted (a state shown in FIG. 2A), turns to a position allowing the arm to extend in a direction M3 of the prealigner 25, and stops at this position. The arm then extends again, and mounts the wafer held by the arm on the prealigner 25. After the wafer is received from the prealigner in a manner inverted from the above description, the arm further turns and stops at a position allowing the arm to extend toward the second loading chamber 41 (direction M4), and exchanges the wafer with the wafer rack 47 in the second loading chamber 41. In the case of mechanically gripping the wafer, the peripheral portion of the wafer (a range within about 5 mm from the periphery) is grasped. This gripping manner is adopted because a device (circuit wiring) is formed on the entire surface except for the peripheral part of the wafer and gripping of this portion breaks the device and causes a defect.

The second conveyance unit 63 has a structure basically identical to the structure of the first conveyance unit. The structure is different only in that the wafer is conveyed between the wafer rack 47 and the mounting surface of the stage device. Accordingly, the detailed description is omitted.

In the loader 60, the first and second conveyance units 61 and 63 convey a wafer from the cassette held in the cassette holder onto the stage device 50 disposed in the working chamber 31 and convey a wafer in the inverse direction, in a state where the wafer is maintained in a horizontal orientation. The arm of the conveyance unit vertically moves only in the cases where the wafer is picked up from and inserted into the cassette, the wafer is mounted on and picked up from the wafer rack, and the wafer is mounted on and picked up from the storage device. Accordingly, even a large wafer, e.g., a wafer having a diameter of 30 cm, can be smoothly moved.

Wafer Conveyance

Next, conveyance of a wafer from the cassette c supported by the cassette holder to the stage device 50 disposed in the working chamber 31 will be sequentially described.

In the case of manually setting the cassette, the cassette holder 10 may be a holder having a structure suitable to the setting manner. In the case of automatically setting the cassette, the cassette holder 10 may be a holder having a structure suitable to the setting manner. In this embodiment, after the cassette c is set on the lifting table 11 of the cassette holder 10, the lifting table 11 is lowered by the lifting mechanism 12 to match the cassette c with the gateway 225.

After the cassette matches with the gateway 225, a cover (not shown) provided on the cassette opens. Furthermore, a cylindrical cover is disposed between the cassette c and the gateway 225 of the mini-environment. The configuration isolates the insides of the cassette and the mini-environment space from the outside. These structures are publicly known. Accordingly, detailed description on the structures and operations is omitted. In the case where a shutter device that opens and closes the gateway 225 is provided on the mini-environment device 20, the shutter device operates to open the gateway 225.

Meanwhile, the arm 612 of the first conveyance unit 61 stops in any of states of orientations in the directions M1 and M2 (the direction M1 in this direction). After the gateway 225 opens, the arm extends and receives one of the wafers stored in the cassette at the distal end of the arm. The vertical positions of the arm and the wafer to be picked up from the cassette are adjusted by vertically moving the driver 611 and the arm 612 of the first conveyance unit 61 in this embodiment. Instead, the movement may be achieved by vertically moving the lifting table of the cassette holder. Both movements may be adopted.

After the arm 612 has received the wafer, the arm is contracted. The gateway is closed by operating the shutter device (in the case with the shutter device). Next, the arm 612 comes into a state capable of extending in the direction M3 by turning about the axis $O_1$-$O_1$. The arm then extends and mounts, on the prealigner 25, the wafer mounted on the distal end of the arm or gripped by the chuck. The prealigner positions the orientation of the wafer in the turning direction (the direction about a central axis perpendicular to the wafer surface) within a prescribed range. After the positioning has been completed, the conveyance unit 61 receives the wafer from the prealigner 25 at the distal end of the arm and subsequently the arm is contracted to have an orientation allowing the arm to extend toward in the direction M4. The door 272 of the shutter device 27 then operates to open the gateways 226 and 436, the arm 612 extends to mount the wafer on the upper stage or the lower stage of the wafer rack 47 in the first loading chamber 41. As described above, before the shutter device 27 opens and the wafer is carried into the wafer rack 47, the opening 435 formed at the partition wall 434 is hermetically closed by the door 461 of the shutter device 46.

In the process of conveying the wafer by the first conveyance unit, cleaned air flows as a laminar flow (as a downflow) from the gas supply unit 231 provided on the housing of the mini-environment device. The flow prevents dust from adhering to the upper surface of the wafer during conveyance. A part of air around the conveyance unit (about 20% of air that is supplied from a supply unit and mainly dirty in this embodiment) is sucked from the intake duct 241 of the evacuator 24 and evacuated out of the housing. The remaining air is collected through the collection duct 232 provided at the bottom of the housing, and returned to the gas supply unit 231 again.

After the wafer is mounted in the wafer rack 47 in the first loading chamber 41 of the loader housing 40 by the first conveyance unit 61, the shutter device 27 is closed to seal the inside of the loading chamber 41. The inert gas is then charged in the first loading chamber 41 to evacuate the air, and subsequently the inert gas is also evacuated. The inside of the loading chamber 41 is thus in a vacuum atmosphere. The vacuum atmosphere of the first loading chamber may be a low degree of vacuum. After a certain degree of vacuum is achieved in the loading chamber 41, the shutter device 46 operates to open the gateway 434 having being hermetically closed with the door 461, the arm 632 of the second conveyance unit 63 extends, and receives one wafer from the wafer rack 47 by the grip device at the distal end (mounted on the distal end or gripped by the chuck attached to the distal end). After the wafer has been received, the arm is contracted, the shutter device 46 operates again, and the gateway 435 is closed with the door 461. Before the shutter device 46 opens, the arm 632 preliminarily becomes in an orientation capable of extending in the direction N1 toward the wafer rack 47. As described above, before the shutter device 46 opens, the gateways 437 and 325 are closed with the door 452 of the shutter device 45, communication between the insides of the second loading chamber 42 and the working chamber 31 is blocked in a hermetical state, and the inside of the second loading chamber 42 is vacuum-evacuated.

After the shutter device 46 closes the gateway 435, the inside of the second loading chamber is vacuum-evacuated again to be in a degree of vacuum higher than the degree in the first loading chamber. Meanwhile, the arm of the second conveyance unit 61 turns to a position capable of extending in the direction toward the stage device 50 in the working chamber 31. On the other hand, in the stage device in the working chamber 31, the Y table 52 moves upward in FIG. 2A to a position where the center line $X_0$-$X_0$ of the X table 53 substantially matches with the X axis $X_1$-$X_1$ crossing the turning axis $O_2$-$O_2$ of the second conveyance unit 63. The X table 53 moves to a position approaching the left-most position in FIG. 2A. The tables are thus in a waiting state. When the second loading chamber becomes a state substantially identical to a vacuum state in the working chamber, the door 452 of the shutter device 45 operates to open the gateways 437 and 325, the arm extends, and thus the distal end of the arm holding the wafer approaches the stage device in the working chamber 31. The wafer is mounted on the mounting surface 551 of the stage device 50. After the wafer has been mounted, the arm is contracted, and the shutter device 45 closes the gateways 437 and 325.

The operations of conveying the wafer in the cassette c onto the stage device has been described above. However, the wafer mounted on the stage device and in a state where the processes have been completed is returned from the stage device to the cassette c according to inverted operations with respect to the aforementioned operations. Since the multiple wafers are mounted on the wafer rack 47, a wafer can be conveyed between the cassette and the wafer rack by the first conveyance unit during conveyance of a wafer between the wafer rack and the stage device by the second conveyance unit. Accordingly, the inspection process can be efficiently performed.

More specifically, in the case where a processed wafer A and an unprocessed wafer B are on the wafer rack 47 of the second conveyance unit, (1) first, the unprocessed wafer B is moved to the stage device 50, and the process is started, and (2) during the process, the processed wafer A is moved by the arm from the stage device 50 to the wafer rack 47, and the unprocessed wafer C is picked up from the wafer rack also by the arm, positioned by the prealigner, and subsequently moved to the wafer rack 47 of the loading chamber 41.

Thus, in the wafer rack 47, during the process on the wafer B, the processed wafer A can be replaced with the unprocessed wafer C.

According to certain usage of such an apparatus performing inspection or evaluation, multiple stage devices 50 may be arranged in parallel, and the wafer may be moved from one wafer rack 47 to each apparatus, thereby allowing multiple wafers to be subjected to the same process.

Figure 6:
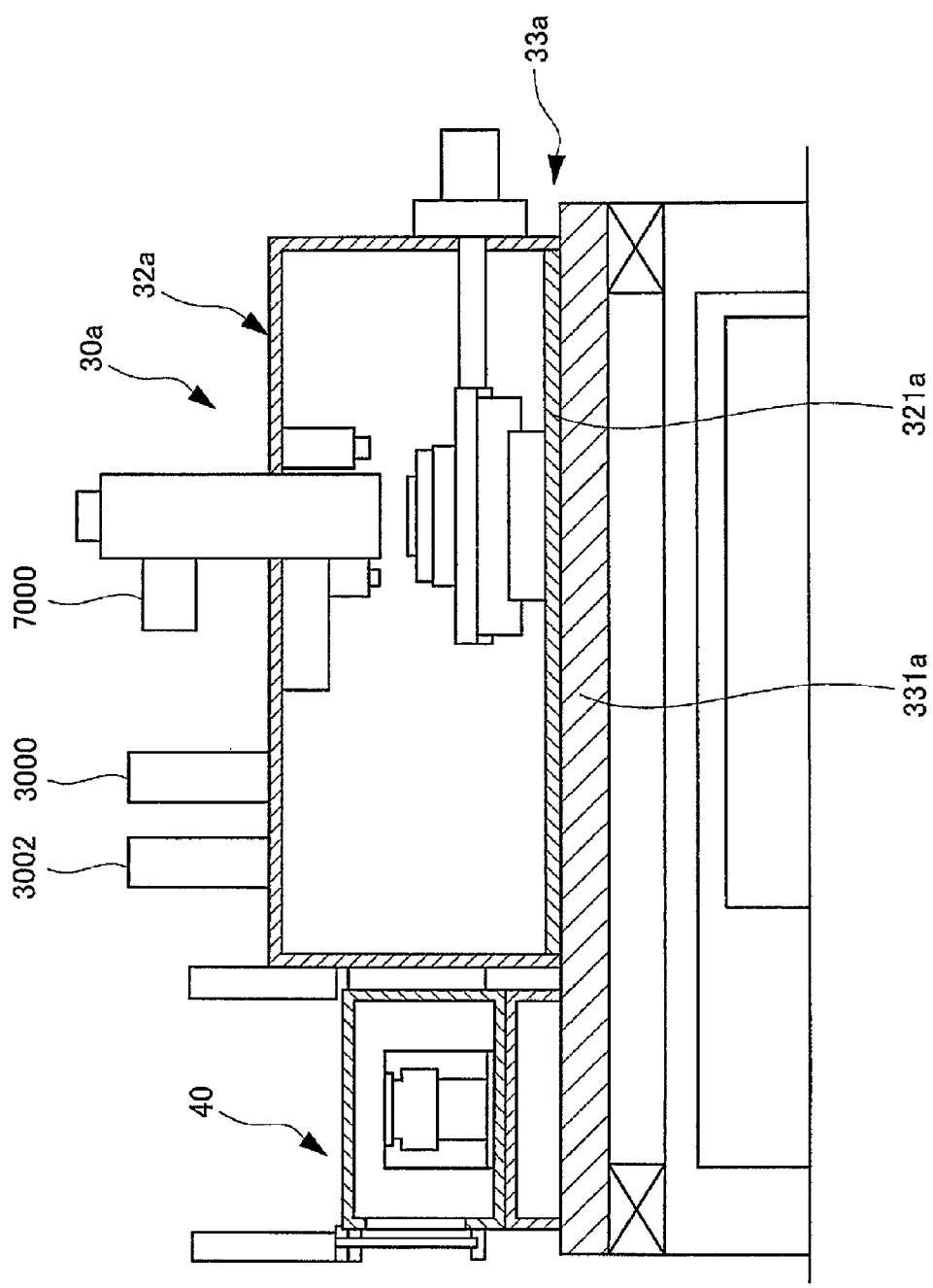
FIG. 6 is a diagram showing a variation of a method of supporting a main housing.
Figure 7:
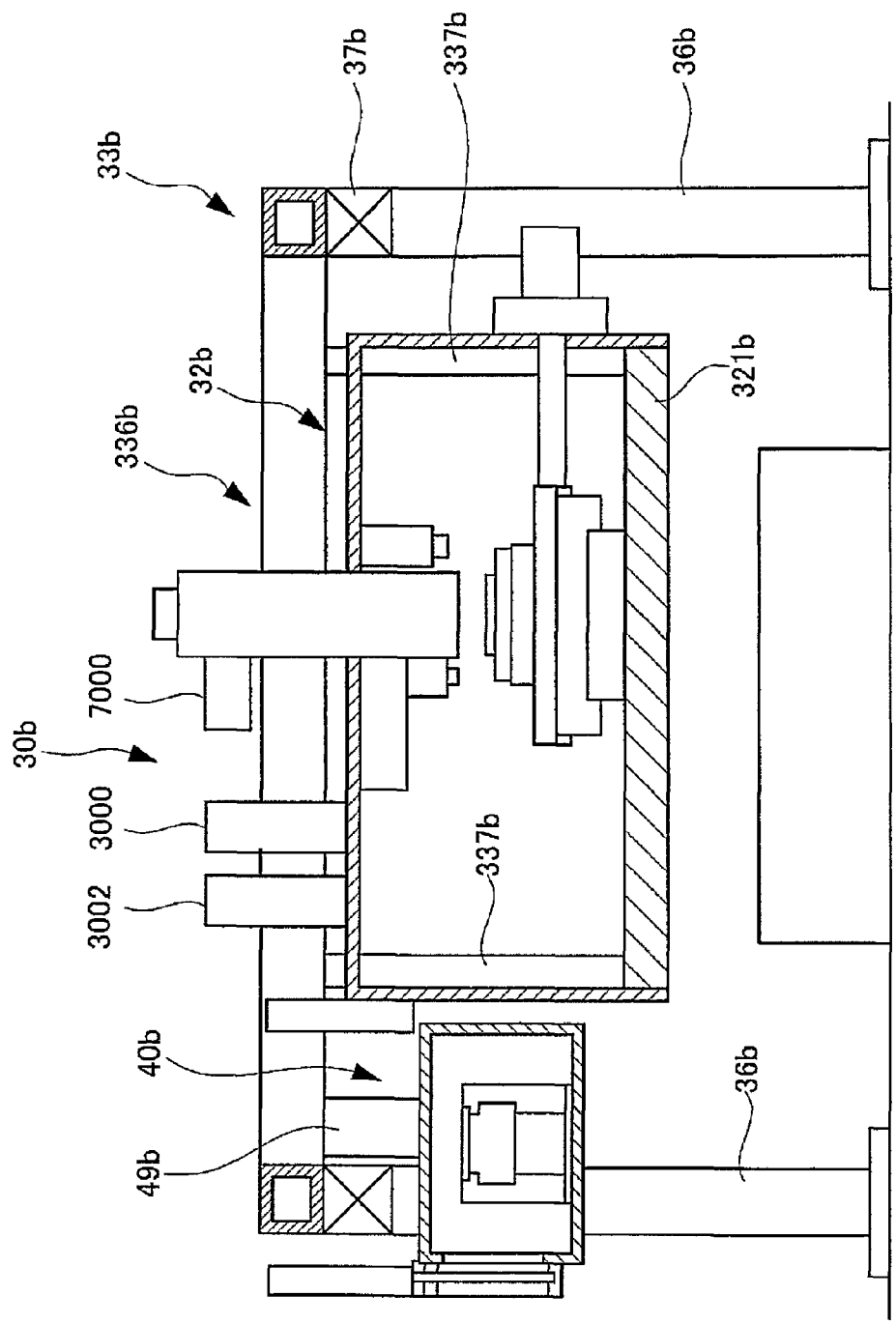
FIG. 7 is a variation of the method of supporting a main housing.

FIG. 6 shows a variation of a method of supporting a main housing. In the variation shown in FIG. 6, the housing supporter 33*a* includes a steel plate 331*a* that is thick and rectangular. A housing main body 32*a* is mounted on the steel plate. Accordingly, a bottom wall 321*a* of the housing main body 32*a* has a thinner structure than the bottom wall of the aforementioned embodiment. In a variation shown in FIG. 7, a housing main body 32*b* and a loader housing 40*b* are suspended and supported by a frame structure 336*b* of a housing supporter 33*b*. The bottom ends of multiple vertical frames 337*b* fixed to the frame structure 336*b* are fixed to the four corners of the bottom wall 321*b* of the housing main body 32*b*. The bottom wall supports surrounding walls and a top wall. Vibration isolators 37*b* are disposed between the frame structure 336*b* and the base frame 36*b*. The loader housing 40 is also suspended by a supporting member 49*b* fixed to the frame structure 336. In the variation of the housing main body 32*b* shown in FIG. 7, the support is achieved by suspension. Accordingly, in this variation, the centers of gravity of the main housing and all the devices provided in this housing can be lowered. The method of supporting the main housing and the loader housing, which includes the variations, prevents vibrations of the floor from being transmitted to the main housing and the loader housing.

In another variation, not shown, only the housing main body of the main housing may be supported by a housing supporting device from the lower side, and the loader housing may be disposed on the floor according to the same method as of the adjacent mini-environment device. In a still another variation, not shown, only the housing main body of the main housing may be supported by the frame structure in a suspending manner, and the loader housing may be disposed on the floor according to the same method as of the adjacent mini-environment device.

The embodiments can exert the following advantageous effects.

(A) The entire configuration of the mapping projection inspection apparatus that uses an electron beam can be acquired, and inspection objects can be processed at high throughput.

(B) In the mini-environment space, cleaned gas flows around the inspection object to prevent dust from adhering, and the sensors observing cleanness are provided. Thus, the inspection object can be inspected while dust in the space is monitored.

(C) The loading chamber and the working chamber are integrally supported via the vibration isolation device. Accordingly, the inspection object can be supplied to the stage device and inspected without being affected by the external environment.

Electronic Optical Device

Figure 8:
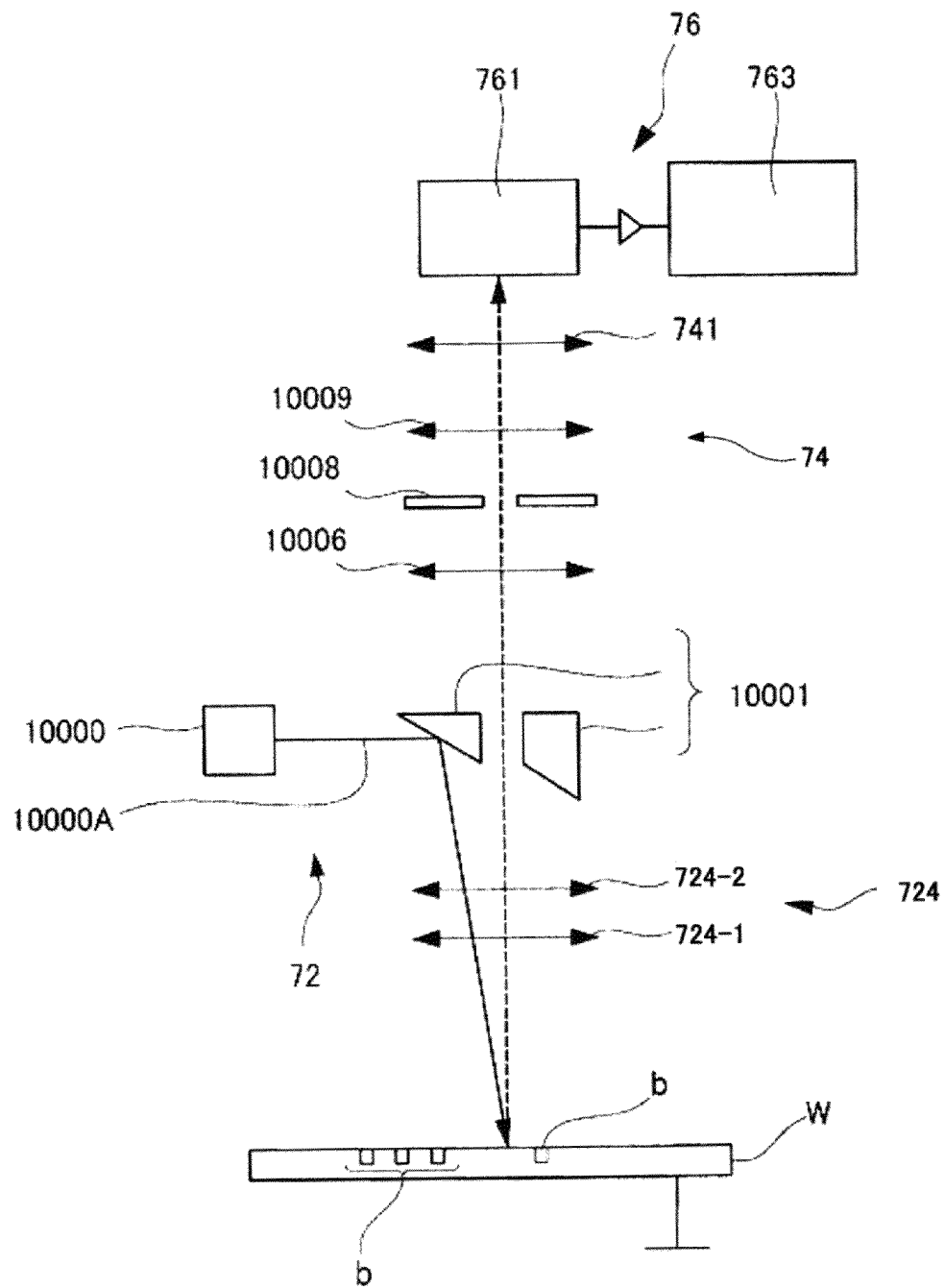
FIG. 8 is a schematic diagram showing an overview of a configuration of a light irradiation electronic optical device.

The electronic optical device 70 includes the lens tube 71 fixed to the housing main body 32. This tube internally includes: an optical system including a primary light source optical system (hereinafter, simply referred to as "primary optical system") 72 and a secondary electronic optical system (hereinafter, simply referred to as "secondary optical system") 74; and a detection system 76. FIG. 8 is a schematic diagram showing an overview of a configuration of a "light irradiation type" electronic optical device. In the electronic optical device (light irradiation electronic optical device) in FIG. 8, a primary optical system 72, which is an optical system irradiating a surface of a wafer W as an inspection object with a light beam, includes a light source 10000 that emits the light beam, and a mirror 10001 that changes the direction of the light beam. In the light irradiation electronic optical device, the optical axis of the light beam 10000A emitted from the light source is inclined from the optical axis (perpendicular to the surface of the wafer W) of photoelectrons emitted from the wafer W, which is the inspection object.

The detection system 76 includes a detector 761 disposed on an imaging surface of a lens system 741, and an image processor 763.

Light Source (Light Beam Source)

In the electronic optical device in FIG. 8, a DUV laser light source is adopted as a light source 10000. The DUV laser light source 10000 emits DUV laser light. Another light source may be adopted that allows photoelectrons to emit from a substrate irradiated with light from the light source 10000, such as UV, DUV, and EUV light and laser, X-rays and X-ray laser.

Primary Optical System

An optical system where a light beam emitted from the light source 10000 forms a primary light beam, with which a surface of the wafer W is irradiated, forming a rectangular or circular (or elliptical) beam spot, is referred to as a primary optical system. The light beam emitted from the light source 10000 passes through an objective lens optical system 724, and the light beam serves as the primary light beam with which the wafer WF on the stage device 50 is irradiated.

Secondary Optical System

A two-dimensional image of photoelectrons caused by the light beam with which the wafer W is irradiated passes through a hole formed at the mirror 10001, is formed at a field stop position by electrostatic lenses (transfer lenses) 10006 and 10009 through a numerical aperture 10008, enlarged and projected by a lens 741 thereafter, and detected by the detection system 76. The image-forming projection optical system is referred to as a secondary optical system 74.

Here, a minus bias voltage is applied to the wafer. The difference of potentials between the electrostatic lens 724 (lenses 724A and 724B) and the wafer accelerates the photoelectrons caused on the surface of the sample to exert an advantageous effect of reducing chromatic aberration. An extracted electric field in the objective lens optical system 724 is 3 to 10 kV/mm, which is a high electric field. There is a relationship where increase in extracted electric field exerts advantageous effects of reducing aberrations and improving resolution. Meanwhile, increase in extracted electric field increases voltage gradient, which facilitates occurrence of evacuated. Accordingly, it is important to select and use an appropriate value of the extracted electric field. Electrons enlarged to a prescribed magnification by the lens 724 (CL) is converged by the lens (TL1) 10006, and forms a crossover (CO) on the numerical aperture 10008 (NA). The combination of the lens (TL1) 10006 and the lens (TL2) 10009 can zoom the magnification. Subsequently, the enlarged projection is performed by the lens (PL) 741, and an image is formed on an MCP (micro channel plate) on the detector 761. In this optical system, NA is disposed between TL1-TL2. The system is optimized to configure an optical system capable of reducing off-axis aberrations.

Detector

A photoelectronic image from the wafer to be formed by the secondary optical system is amplified by the micro channel plate (MCP), subsequently collides with a fluorescent screen and converted into an optical image. According to the principle of the MCP, a prescribed voltage is applied using a hundred of significantly fine, conductive glass capillaries that are bundled to have a diameter 6 to 25 μm and a length of 0.24 to 1.0 mm and formed into a shape of a thin plate, thereby allowing each of the capillaries to function as independent electronic amplifier; the entire capillaries thus form an integrated electronic amplifier.

The image converted into light by the detector is projected on a TDI (time delay integration)-CCD (charge coupled device) by an FOP (fiber optical plate) system disposed in the atmosphere through a vacuum transmissive window in one-to-one mapping. According to another projection method, the FOP coated with fluorescent material is connected to the surface of a TDI sensor, and a signal electronically/optically converted in a vacuum may be introduced into the TDI sensor. This case has a more efficient transmittance and efficiency of an MTF (modulation transfer function) than the case of being arranged in the atmosphere has. For instance, the transmittance and MTF can be high values of ×5 to ×10. Here, the combination of the MCP and TDI may be adopted as the detector as described above. Instead, an EB (electron bombardment)-TDI or an EB-CCD may be adopted. In the case of adopting the EB-TDI, photoelectrons caused on the surface of the sample and forming a two-dimensional image is directly incident onto the surface of the EB-TDI sensor. Accordingly, an image signal can be formed without degradation in resolution. For instance, in the case of the combination of the MCP and TDI, electronic amplification is performed by the MCP, and electronic/optical conversion is performed by fluorescent material or a scintillator, and information on the optical image is delivered to the TDI sensor. In contrast, the EB-TDI and the EB-CCD have no component for electronic/optical conversion and no transmission component for optical amplification information and thus have no loss due to the component. Accordingly, a signal can be transmitted to the sensor without image degradation. For instance, in the case of adopting the combination of the MCP and TDI, the MTF and contrast are ½ to ⅓ of the MTF and contrast in the cases of adopting the EB-TDI and the EB-CCD.

In this embodiment, it is provided that a high voltage of 10 to 50 kV is applied to the objective lens system 724, and the wafer W is arranged.

Figure 9:
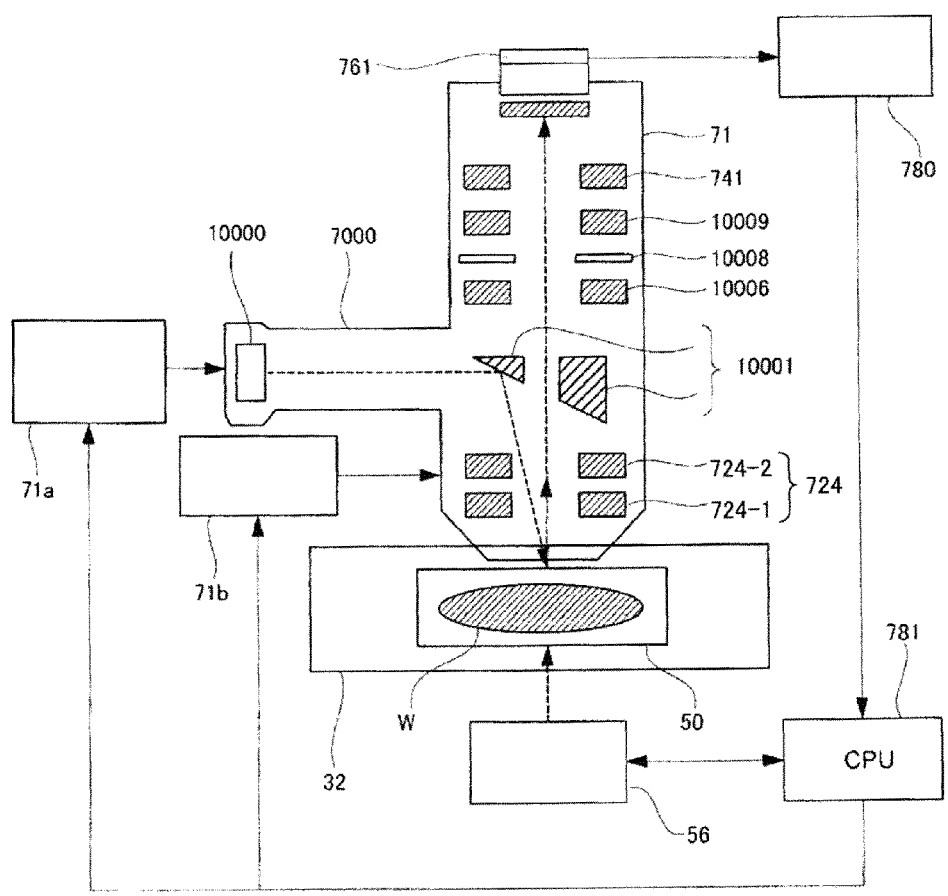
FIG. 9 is a diagram showing the entire configuration of the inspection apparatus according to an embodiment of the present invention.

Description on Relationship of Main Functions of Mapping Projection System and Overview FIG. 9 is a diagram showing the entire configuration of this embodiment. However, certain parts of components are abbreviated in the diagram.

In FIG. 9, the inspection apparatus includes the lens tube 71, a light source tube 7000, and a chamber 32. The light source 10000 is provided in the light source tube 7000. The primary optical system 72 is disposed on the optical axis of a light beam (primary light beam) emitted from the light source 10000. The stage device 50 is installed in the chamber 32. The wafer W is mounted on the stage device 50.

Meanwhile, the cathode lens 724 (724A and 724B), the transfer lenses 10006 and 10009, the numerical aperture (NA) 10008, the lens 741 and the detector 761 are disposed on the optical axis of a secondary beam emitted from the wafer W, in the lens tube 71. The numerical aperture (NA) 10008 corresponds to an aperture stop, and is a thin plate that is made of metal (Mo. etc.) and has a circular hole.

The output of the detector 761 is input into a control unit 780. The output of the control unit 780 is input into a CPU 781. Control signals of the CPU 781 are input into a light source control unit 71a, a lens tube control unit 71b and a stage driving mechanism 56. The light source control unit 71a controls power supply to the light source 10000. The lens tube control unit 71b controls the lens voltages of the cathode lens 724, the lenses 10006 and 10009, and the lens 741, and the voltage of an aligner (not shown) (control of deflection).

The stage driving mechanism 56 transmits position information of the stage to the CPU 781. The light source tube 7000, the lens tube 71, and the chamber 32 communicate with a vacuum evacuation system (not shown). Air in the vacuum evacuation system is evacuated by a turbo pump of the vacuum evacuation system, and the inside of the chamber is kept in a vacuum. A rough evacuation system that typically adopts a dry pump or a rotary pump is disposed on a downstream side of the turbo pump.

When the sample is irradiated with the primary light beam, photoelectrons occur as the secondary beam from the surface of the wafer W irradiated with the light beam.

The secondary beam passes through the cathode lens 724, the group of TL lenses 10006 and 10009 and the lens (PL) 741, and is guided to the detector and formed as an image.

The cathode lens 724 includes three electrodes. It is designed such that the lowermost electrode forms a positive electric field with respect to the potential on the side of the sample W, and electrons (more specifically, secondary electrons having a small directivity) are extracted and efficiently guided into the lens. Thus, it is effective that the cathode lens is bi-telecentric. The secondary beam image-formed by the cathode lens passes through the hole of the mirror 10001.

If the secondary beam is image-formed by only one stage of the cathode lens 724, the effect of the lens is too strong. Accordingly, aberration easily occurs. Thus, the two stages of the doublet lens system are adopted for a formation of an image. In this case, the intermediate image formation position is between the lens (TL1) 10006 and the cathode lens 724. Here, as described above, the bi-telecentric configuration significantly exerts an advantageous effect of reducing the aberration. The secondary beam is converged on the numerical aperture (NA) 10008 by the cathode lens 724 and the lens (TL1) 10006, thereby forming a crossover. The image is formed between the lens 724 and lens (TL1) 10006. Subsequently, an intermediate magnification is defined by the lens (TL1) 10006 and the lens (TL2) 10009. The image is enlarged by the lens (PL) 741 and formed on the detector 761. That is, in this example, the image is formed three times as a total.

All the lenses 10006, 10009 and 741 are rotationally symmetrical lenses referred to as unipotential lenses or einzel lenses. The lenses have a configuration including three electrodes. Typically, the external two electrodes are zero potential, and control is performed by applying a voltage to the central electrode to exert a lens effect. The configuration is not limited to this lens configuration. Instead, the case of a configuration including a focus adjustment electrode on the first or second stage or both the stages of the lens 724, the case of including dynamic focus adjustment electrode and has a quadrupole or quintuple-pole configuration can be adopted. The field lens function may be added to the PL lens 741 to reduce off-axis aberrations, and a quadrupole or quintuple-pole configuration may effectively be adopted to increase the magnification.

The secondary beam is enlarged and projected by the secondary optical system, and image-formed on the detection surface of the detector 761. The detector 761 includes: the MCP that amplitudes electrons; a fluorescent plate that converts the electrons into light; a lens or another optical element for relaying an optical image between the vacuum system and the outside; and an image pickup element (CCD etc.). The secondary beam is image-formed on the MCP detection surface, and amplified. The electrons are converted into an optical signal by the fluorescent plate, and further converted into a photoelectric signal by an image pickup element.

The control unit 780 reads the image signal of the wafer W from the detector 761 and transmits the read signal to the CPU 781. The CPU 781 inspects defect on a pattern based on the image signal according to template matching or the like. The stage device 50 is movable in the XY direction by the stage driving mechanism 56. The CPU 781 reads the position of the stage device 50, outputs a drive control signal to the stage driving mechanism 56 to drive the stage device 50, thereby sequentially detecting and inspecting images.

As to change in magnification, even if a set magnification, which is lens conditions of the lenses 10006 and 10009, is changed, a uniform image can be acquired on the entire field of view on the detection side. In this embodiment, a uniform image without irregularity can be acquired. However, increase in magnification causes a problem of decreasing the brightness of the image. In order to solve the problem, the lens condition of the primary optical system is set such that the amount of emitted electrons per unit pixel is constant when the lens condition of the secondary optical system is changed to change the magnification.

Precharge Unit

As shown in FIG. 1, the precharge unit 81 is arranged adjacent to the lens tube 71 of the electronic optical device 70 in the working chamber 31. This inspection apparatus is an apparatus that inspects a device pattern and the like formed on the surface of the wafer by irradiating the substrate as the inspection object, i.e., wafer, with the electron beam. The information on the photoelectrons caused by irradiation with the light beam is information on the surface of the wafer. However, the surface of the wafer may be charged (charged up) according to conditions, such as a wafer material, the wavelength and energy of irradiation light or laser. Furthermore, a strongly charged spot and a weakly charged spot may occur on the surface of the wafer. If there is irregularity of the amount of charge on the surface of the wafer, the photoelectronic information also includes irregularity. Accordingly, correct information cannot be acquired. Thus, in this embodiment, to prevent the irregularity, the precharge unit 81 including a charged particles irradiation unit 811 is provided. Before a prescribed spot on the wafer to be inspected is irradiated with light or laser, charged particles are emitted from the charged particles irradiation unit 811 of the precharge unit to eliminate charging irregularity. The charging-up on the surface of the wafer preliminarily forms an image of the surface of the wafer, which is a detection object. Detection is performed by evaluating the image to operate the precharge unit 81 on the basis of the detection.

Embodiment 1

Semiconductor Inspection Apparatus Including Double Pipe Structure Lens Tube

As described above, the electronic optical device 70 including the primary optical system 2100, which is described as the second embodiment of the primary optical system according to the invention of this application, is different in setting of voltages applied to the respective configurational components from a typical electron gun. That is, reference potential V2 is used as the high voltage (e.g., +40000 V). First, the semiconductor inspection apparatus 1 including the electronic optical device 70 according to the invention of this application has a double pipe structure.

Figure 10:
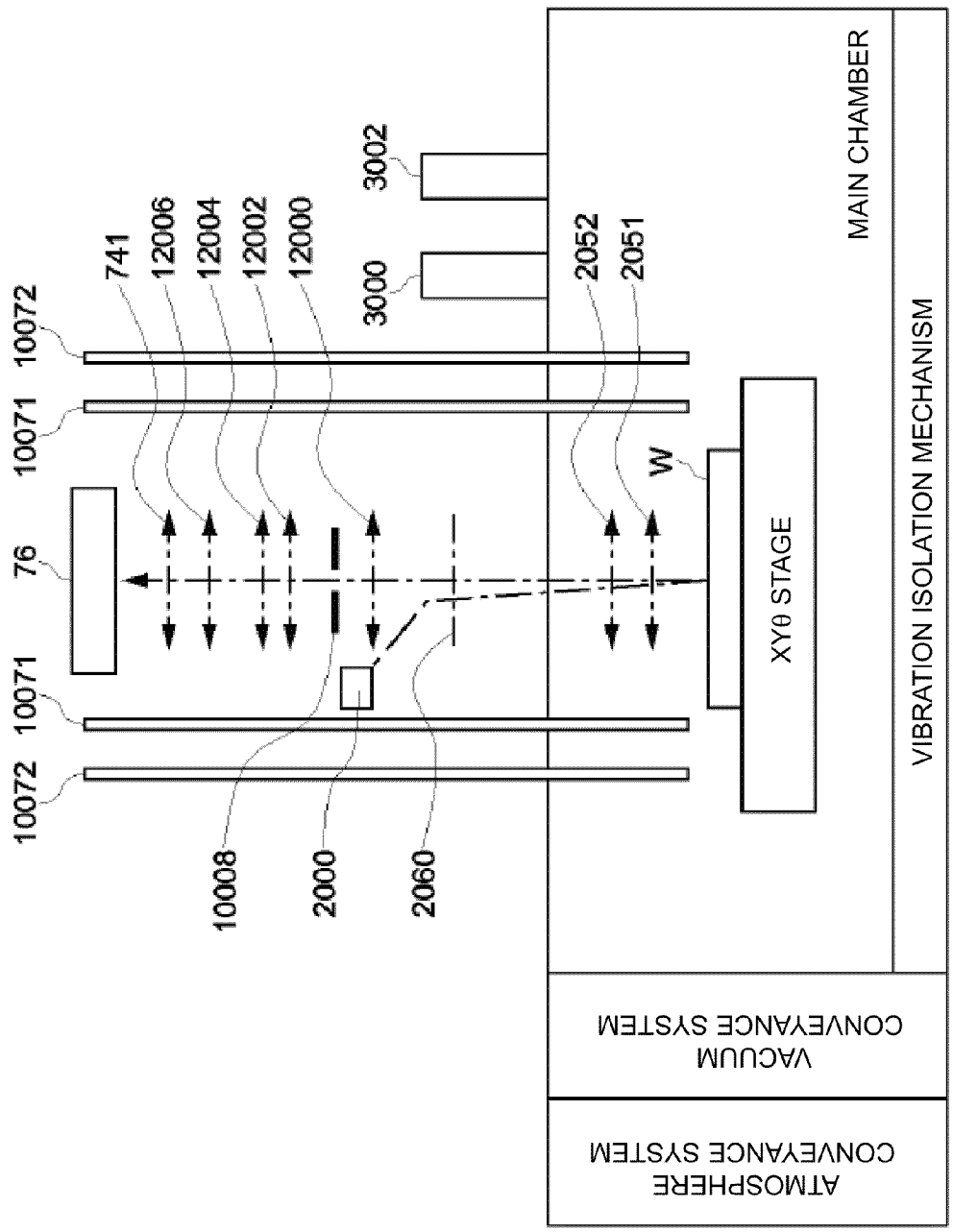
FIG. 10 is a diagram schematically showing a double pipe structure of a semiconductor inspection apparatus according to an embodiment of the present invention.

Description will be made with reference to FIG. 10. FIG. 10 is a diagram schematically showing the double pipe structure of the semiconductor inspection apparatus according to one embodiment of the present invention. In FIG. 10, the first pipe and the second pipe are emphasized. The sections of the actual first pipe and second pipe are different from the illustration. As shown in FIG. 10, the electronic optical device 70 including the primary optical system 2000 according to the invention of this application includes two pipes, which are the first pipe 10071, and a second pipe 10072 provided outside of the first pipe 10071. In other words, the device has a double pipe structure. The double pipe structure internally stores a light source, a primary optical system, a secondary optical system and a detector. A high voltage (e.g., +40000 V) is applied to the first pipe 10071. The second pipe 10072 is set to GND. The first pipe 10071 secures a spatial reference potential V0 with reference to the high voltage. The first pipe is surrounded by the second pipe and is thus set to GND. This configuration achieves GND connection in the apparatus installation and prevents electric shock. The pipe 10071 is fixed to the pipe 10072 by insulative components. The pipe 10072 is set to GND, and attached to the main housing 30. The primary optical system 2000, the secondary optical system, the detection system 76 and the like are arranged in the first pipe 10071.

An internal partition wall between the first pipe 10071 and the second pipe 10072, even including components screws and the like, are made of nonmagnetic material not to affect the magnetic field, thereby preventing the magnetic field from affecting the electron beam. Although not shown in FIG. 10, a space is provided at the side of the second pipe 10072. In the space, a protrusion is connected in which parts of the primary optical system 2000, such as the light source and the photoelectron generator, are arranged. A space similar to the space provided for the second pipe 10072 is also provided for the first pipe 10071. Photoelectrons occurring from the photoelectron generation portion pass through the spaces, and the sample is irradiated with the photoelectrons. The light source is not necessarily provided in the second pipe 10072. Instead, the light source may be provided on the atmosphere side, and light may be introduced into the photoelectron generation portion stored in the second pipe 10072 on the vacuum side. However, the primary optical system and the secondary optical system are necessarily stored in the double pipe structure. The detector may be disposed in the first pipe 10071, or at the position with a potential independent from the first and second pipes. Here, the potential of the detection surface of the detector is set to any value to control the energy of electrons incident on the detector to have an appropriate value. In a state of potential separation by the insulative component from the pipe 1 and the pipe 2, any voltage is applied to the detector to achieve a detection sensor surface potential, thereby allowing operation. Here, provided that the sensor surface potential is VD, the energy incident on the sensor surface is defined by VD-RTD. In the case where EB-CCD or EB-TDI is adopted as the detector, it is effective to set the incident energy to 1 to 7 keV for the sake of reducing damage to the sensor and use for a long period of time.

Electronic Inspection Apparatus

Figure 11:
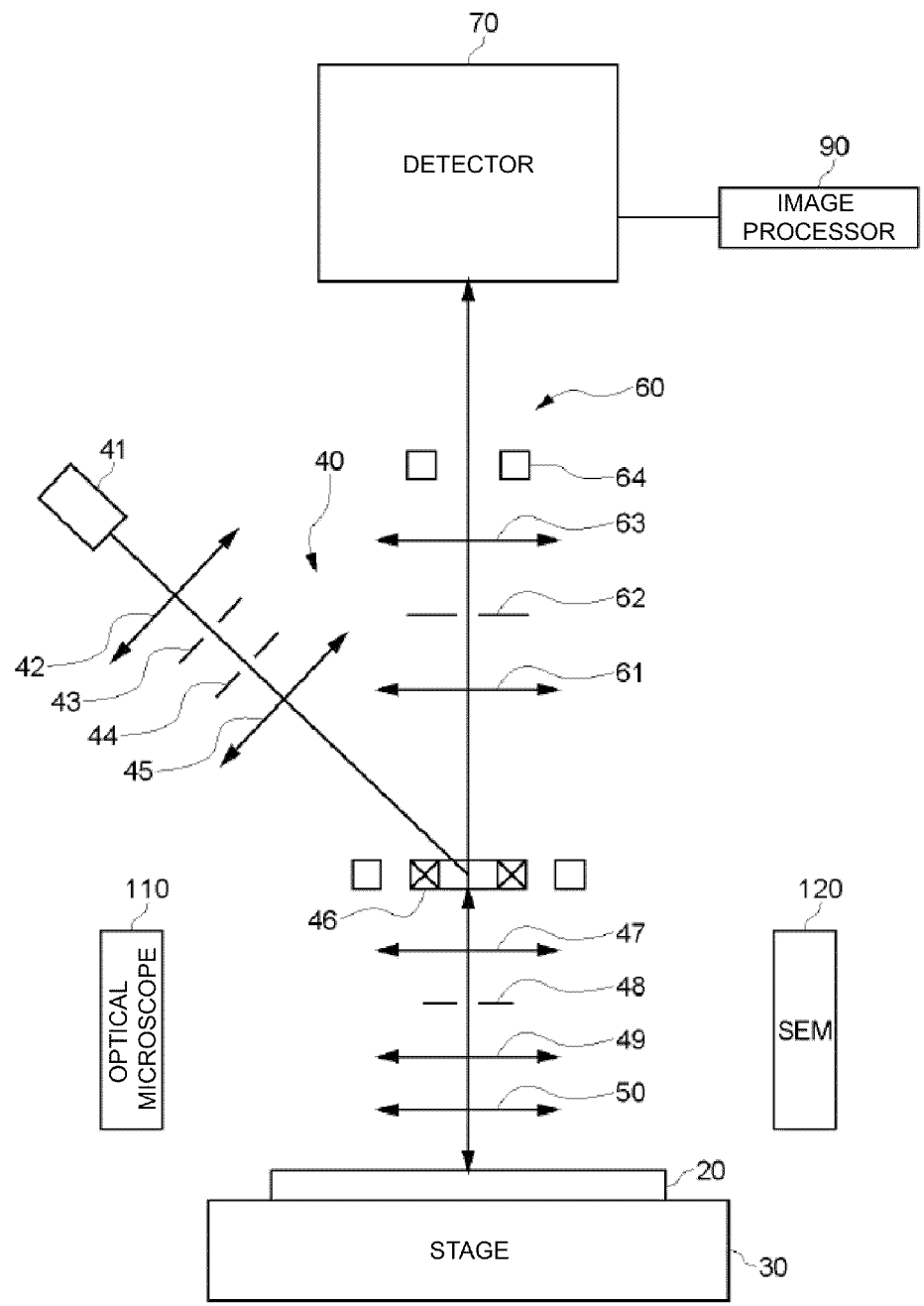
FIG. 11 is a diagram showing a configuration of an electron beam inspection apparatus according to an embodiment of the present invention.

FIG. 11 is a diagram showing a configuration of an electron beam inspection apparatus to which the present invention is applied. The above description has been made mainly on the principle of the foreign matter inspection method. The foreign matter inspection apparatus applied to performing the foreign matter inspection method will herein be described. Accordingly all of the aforementioned foreign matter inspection methods are applicable to the following foreign matter inspection apparatus.

An inspection object of the electron beam inspection apparatus is a sample 20. The sample 20 is any of a silicon wafer, a glass mask, a semiconductor substrate, a semiconductor pattern substrate, and a substrate having a metal film. The electron beam inspection apparatus according to this embodiment detects presence of a foreign matter 10 on the surface of the sample 20 that is any one of these substrates. The foreign matter 10 is insulative material, conductive material, semiconductor material, or a composite thereof. The types of the foreign matter 10 include particles, cleaning residues (organic matters), reaction products on the surface and the like. The electron beam inspection apparatus may be an SEM type apparatus or a mapping projection apparatus. In this example, the present invention is applied to the mapping projection inspection apparatus.

The mapping projection type electron beam inspection apparatus includes: a primary optical system 40 that generates an electron beam; a sample 20; a stage 30 on which the sample is mounted; a secondary optical system 60 that forms an enlarged image of secondarily released electrons or mirror electrons from the sample; a detector 70 that detects the electrons; an image processor 90 (image processing system) that processes a signal from the detector 70; an optical microscope 110 for alignment; and an SEM 120 for review. In the present invention, the detector 70 may be included in the secondary optical system 60. The image processor 90 may be included in the image processor of the present invention.

The primary optical system 40 generates an electron beam, and irradiates the sample 20. The primary optical system 40 includes an electron gun 41; lenses 42 and 45; apertures 43 and 44; an ExB filter 46; lenses 47, 49 and 50; and an aperture 48. The electron gun 41 generates an electron beam. The lenses 42 and 45 and apertures 43 and 44 shape the electron beam and control the direction of the electron beam. In the ExB filter 46, the electron beam is subjected to a Lorentz force due to a magnetic field an electric field. The electron beam enters the ExB filter 46 in an inclined direction, is deflected into a vertically downward direction, and travels toward the sample 20. The lenses 47, 49 and 50 control the direction of the electron beam and appropriately decelerate, thereby controlling the landing energy LE.

The primary optical system 40 irradiates the sample 20 with the electron beam. As described above, the primary optical system 40 performs irradiation with both an electron beam for precharging and an imaging electron beam. In experiment results, the difference between a precharging landing energy LE1 and a landing energy LE2 for an imaging electron beam is preferably 5 to 20 [eV].

In terms of this point, it is provided that in the case with a potential difference between the potential of the foreign matter 10 and the potential therearound, the precharging landing energy LE1 is emitted in a negative charging region. In conformity with the value of LE1, the charging up voltage varies. This variation is because of variation in a relative ratio of the LE1 and the LE2 (LE2 is a landing energy of the imaging electron beam as described above). If the LE1 is high, the charging up voltage is high. Accordingly, a reflection point is formed at an upper position of the foreign matter 10 (position close to the detector 70). The trajectory and transmittance of the mirror electrons vary according to the reflection point. Thus, the optimal charging-up voltage conditions are determined according to the reflection point. If the LE1 is too low, an efficiency of forming the mirror electrons reduces. The present invention has found that the difference between the LE1 and the LE2 is preferably 5 to 20 [eV]. The value of the LE1 is preferably 0 to 40 [eV], and further preferably 5 to 20 [eV].

In the primary optical system 40 of the mapping projection optical system, the ExB filter 46 is particularly important. The primary electron beam angle can be defined by adjusting the conditions of the electric field and the magnetic field of the ExB filter 46. For instance, the irradiation electron beam of the primary system and the electron beam of the secondary system can set the conditions of ExB filter 46 so as to make the incidence substantially rectangular to the sample 20. In order to further increase the sensitivity, for instance, it is effective to incline the incident angle of the electron beam of the primary system with respect to the sample 20. An appropriate inclined angle is 0.05 to 10 degrees, preferably is about 0.1 to 3 degrees.

Thus, the signal from the foreign matter 10 is strengthened by emitting the electron beam at an inclination of a prescribed angle θ with respect to the foreign matter 10. Accordingly, conditions where the trajectory of the mirror electron does not deviate from the center of the secondary optical axis can be formed. Thus, the transmittance of the mirror electron can be increased. Accordingly, in the case where the foreign matter 10 is charged up and the mirror electrons are guided, the inclined electron beam is significantly efficiently used.

Referring again to FIG. 25, the stage 30 is means for mounting the sample 20, and movable in the horizontal x-y directions and the θ direction. The stage 30 may be also movable in the z direction as necessary. Means for fixing a sample, such as an electrostatic chuck, may be provided on the surface of the stage 30.

The sample 20 is on the stage 30. The foreign matter 10 is on the sample 20. The primary optical system 40 irradiates the surface 21 of the sample with the electron beam at a landing energy LE of 5 to −10 [eV]. The foreign matter 10 is charged up, incident electrons in the primary optical system 40 recoil without coming into contact with the foreign matter 10. Accordingly, the mirror electrons are guided by the secondary optical system 60 to the detector 70. Here, the secondarily released electrons are released from the surface 21 of the sample in spread directions. Accordingly, the transmittance of the secondarily released electrons is a low value, for instance, about 0.5 to 4.0%. In contrast, the direction of the mirror electron is not scattered. Accordingly, a transmittance of the mirror electrons of about 100% can be achieved. The mirror electrons are formed on the foreign matter 10. Thus, only the signal of the foreign matter 10 can achieve a high luminance (the state with the large amount of electrons). The difference of the luminance from the ambient secondarily released electrons and the ratio of the luminance increase, thereby allowing high contrast to be achieved.

As described above, the image of the mirror electron is enlarged at a magnification higher than the optical magnification. The magnification ratio reaches 5 to 50. In typical conditions, the magnification ratio is often 20 to 30. Here, even if the pixel size is three times as large as the size of the foreign matter, the foreign matter can be found. Accordingly, high speed and high throughput can be achieved.

For instance, in the case where the size of the foreign matter 10 has a diameter of 20 [nm], it is sufficient that the pixel size is 60 [nm], 100 [nm], 500 [nm] or the like. As with this example, the foreign matter can be imaged and inspected using the pixel size three times as large as the size of the foreign matter. This feature is significantly excellent for high throughput in comparison with the SEM system and the like.

The secondary optical system 60 is means for guiding electrons reflected by the sample 20 to the detector 70. The secondary optical system 60 includes lenses 61 and 63, a NA aperture 62, an aligner 64, and a detector 70. The electrons are reflected by the sample 20, and pass again through the objective lens 50, the lens 49, the aperture 48, the lens 47 and the ExB filter 46. The electrons are then guided to the secondary optical system 60. In the secondary optical system 60, electrons pass through the lens 61, the NA aperture 62 and the lens 63 and are accumulated. The electrons are adjusted by the aligner 64, and detected by the detector 70.

The NA aperture 62 has a function of defining the secondary transmittance and aberrations. The size and the position of the NA aperture 62 are selected such that the difference between the signal from the foreign matter (mirror electron etc.) and the signal from the ambient portions (normal portions) is large. Instead, the size and the position of the NA aperture 62 are selected such that the ratio of the signal from the foreign matter 10 with respect to the ambient signal is large. Thus, the S/N ratio can be high.

For instance, it is provided that the NA aperture 62 can be selected in a range of $\phi 50$ to $\phi 3000$ [µm]. Detected electrons are mixture of mirror electrons and secondarily released electrons. In such situations, the aperture size is effectively selected in order to improve the S/N ratio of the mirror electron image. In this case, it is preferred to select the size of the NA aperture 62 such that the transmittance of the mirror electrons is maintained by reducing the transmittance of the secondarily released electrons.

For instance, in the case where the incident angle of the primary electron beam is 3°, the reflection angle of the mirror electrons is about 3°. In this case, it is preferred to select the size of the NA aperture 62 that allows the trajectory of the mirror electrons to pass. For instance, the appropriate size is $\phi 250$ [µm]. Because of the limitation to the NA aperture (diameter $\phi 250$ [µm]), the transmittance of the secondarily released electrons is reduced. Accordingly, the S/N ratio of the mirror electron image can be improved. For instance, in the case where the aperture diameter is from $\phi 2000$ to $\phi 250$ [µm], the background gradation (noise level) can be reduced to ½ or less.

Referring again to FIG. 25, the detector 70 is means for detecting electrons guided by the secondary optical system 60. The detector 70 has a plurality of pixels on the surface. Various two-dimensional sensors may be adopted as the detector 70. For instance, the detector 70 may be any of a CCD (charge coupled device) and a TDI (time delay integration)-CCD. These are sensors that convert electrons into light and then detect signals. Accordingly, photoelectronic conversion means is required. Thus, electrons are converted into light using photoelectronic conversion or a scintillator. Optical image information is transmitted to the TDI that detects light. The electrons are thus detected.

Here, an example where the EB-TDI is applied to the detector 70 will be described. The EB-TDI does not require a photoelectronic conversion mechanism and an optical transmission mechanism. The electrons are directly incident on the EB-TDI sensor surface. Accordingly, the high MTF (modulation transfer function) and contrast can be acquired without degradation in resolution. Conventionally, detection of small foreign matters 10 has been unstable. In contrast, use of the EB-TDI can improve the S/N ratio of a weak signal of the small foreign matters 10. Accordingly, a higher sensitivity can be achieved. The S/N ratio improves by a factor of 1.2 to 2.

Figure 12:
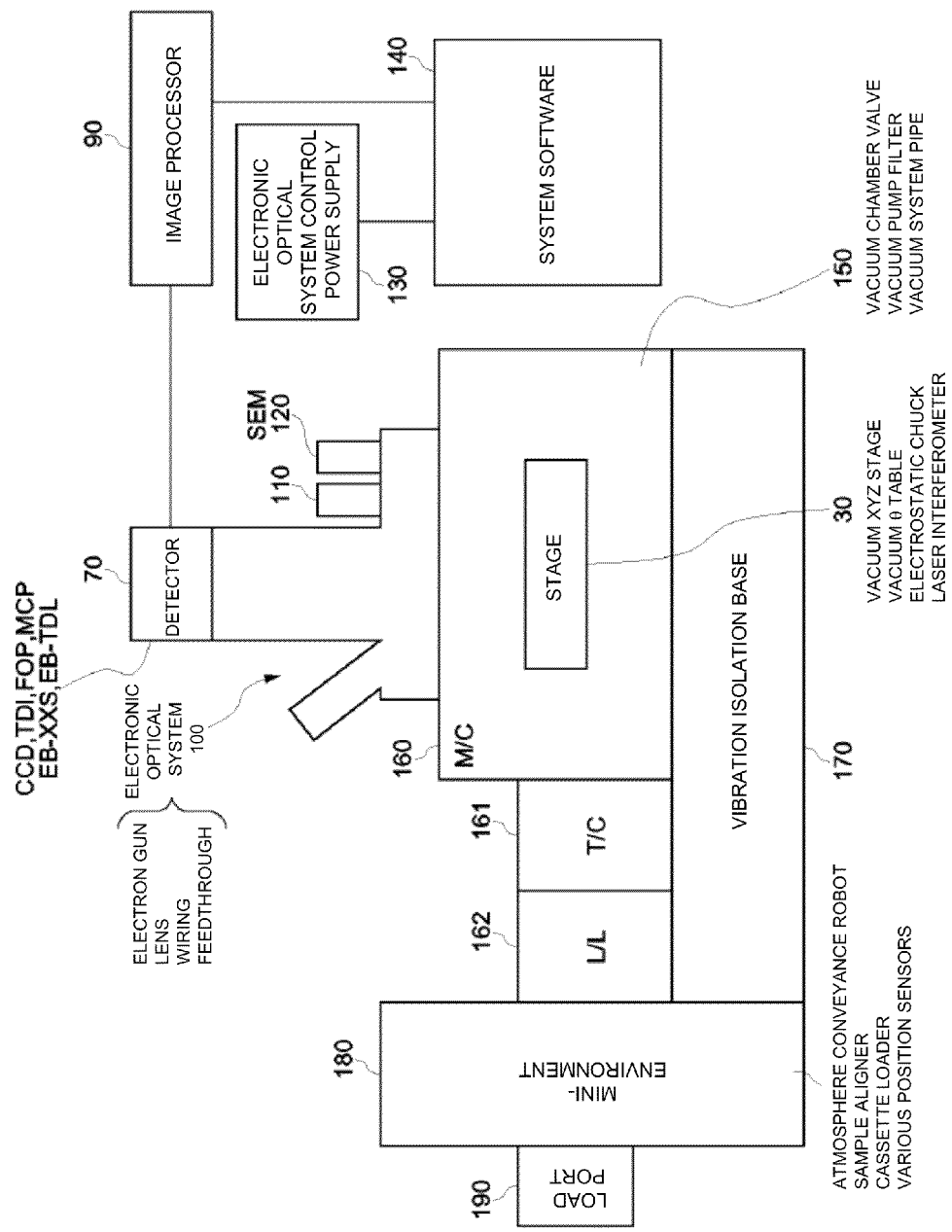
FIG. 12 is a diagram showing an electron beam inspection apparatus to which the present invention is applied, according to an embodiment of the present invention.

FIG. 12 shows an electron beam inspection apparatus to which the present invention is applied. Here, an example of the entire system configuration will be described.

In FIG. 12, the foreign matter inspection apparatus includes: a sample carrier 190; a mini-environment 180; a load lock 162; a transfer chamber 161; a main chamber 160; an electron beam column system 100; and an image processor 90. A conveyance robot in the atmosphere, a sample alignment device, clean air supply mechanism and the like are provided in the mini-environment 180. A conveyance robot in a vacuum is provided in the transfer chamber 161. The robots are arranged in the transfer chamber 161 that is always in a vacuum state. Accordingly, occurrence of particles and the like due to pressure variation can be suppressed to the minimum.

The stage 30 that moves in the X and Y directions and the θ (turning) direction is provided in the main chamber 160. An electrostatic chuck is provided on the stage 30. The sample 20 itself is provided at the electrostatic chuck. Instead, the sample 20 is held by the electrostatic chuck in a state of being arranged on a pallet or a jig.

The main chamber 160 is controlled by the vacuum control system 150 such that the inside of the chamber is kept in a vacuum. The main chamber 160, the transfer chamber 161 and the load lock 162 are mounted on a vibration isolation base 170. The configuration prevents vibrations from the floor from being transmitted.

An electron column 100 is provided on the main chamber 160. The electron column 100 includes: columns of a primary optical system 40 and a secondary optical system 60; and a detector 70 that detects secondarily released electrons, mirror electrons and the like from the sample 20. The signal from the detector 70 is transmitted to the image processor 90 and processed. Both on-time signal processing and off-time signal processing can be performed. The on-time signal processing is performed during inspection. In the case of off-time signal processing, only an image is acquired and the signal processing is performed thereafter. Data processed in the image processor 90 is stored in recording media, such as a hard disk and memory. The data can be displayed on a monitor of a console, as required. The displayed data is, for instance, an inspection region, a map of the number of foreign matters, the size distribution and map of foreign matters, foreign matter classification, a patch image and the like. System software 140 is provided in order to perform signal processing. An electronic optical system control power supply 130 is provided in order to supply power to the electron column system. The optical microscope 110 and the SEM inspection apparatus 120 may be provided in the main chamber 160.

Figure 13:
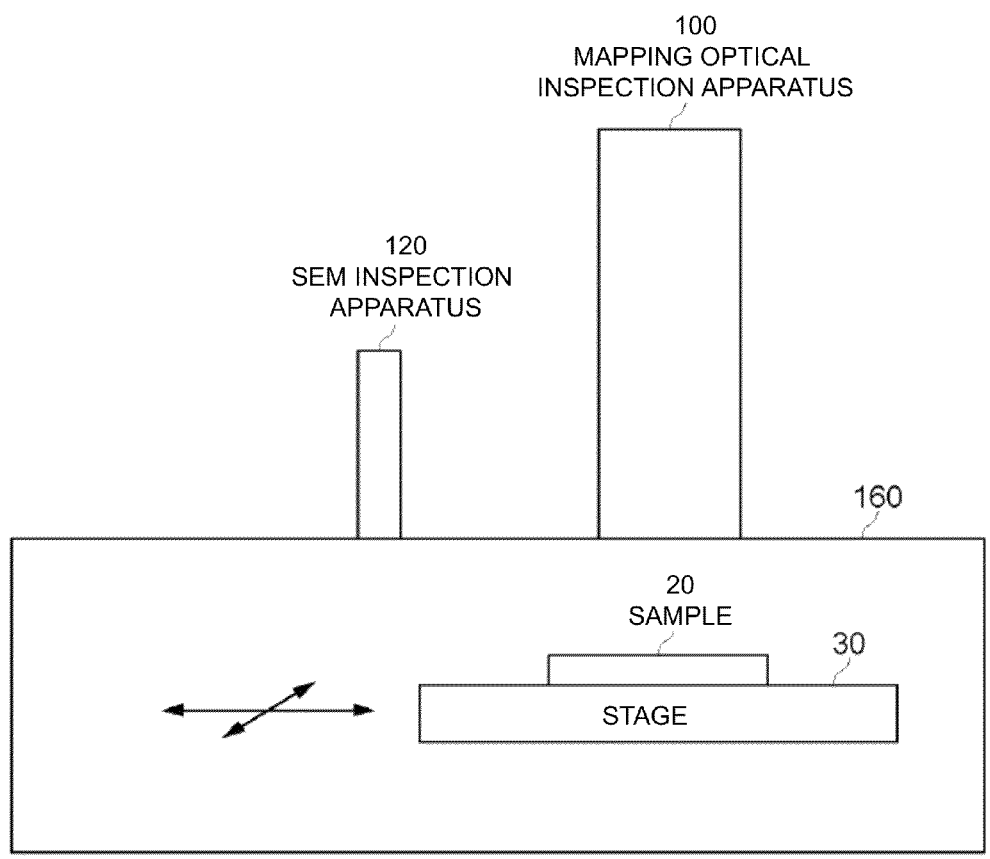
FIG. 13 is a diagram showing an example of a configuration where an electron column of a mapping optical system inspection apparatus and an SEM inspection apparatus are provided in the same main chamber, according to an embodiment of the present invention.

FIG. 13 shows an example of a configuration in the case where an electron column 100 and an SEM inspection apparatus 120 of a mapping optical system inspection apparatus are provided in the same main chamber 160. The arrangement of the mapping optical system inspection apparatus and the SEM inspection apparatus 120 in the same chamber 160 as shown in FIG. 13 is significantly advantageous. A sample 20 is mounted on the same stage 30. The sample 20 can be observed or inspected according to the mapping system and SEM system. A method of using this configuration and advantageous effects thereof are as follows.

Since the sample 20 is mounted on the same stage 30, the coordinate relationship is uniquely defined when the sample 20 is moved between the mapping system electron column 100 and the SEM inspection apparatus 120. Accordingly, when the detection positions of foreign matters are identified, two inspection apparatuses can easily highly accurately identify the same position.

In the case where above configuration is not applied, for instance, the mapping optical inspection apparatus and the SEM inspection apparatus 120 are configured to be separated from each other as different apparatuses. The sample 20 is moved between the separated apparatuses. In this case, the sample 20 is required to be mounted on the separate stages 30. Accordingly, the two apparatuses are required to separately align the sample 20. In the case of separately aligning the sample 20, specific errors at the same position are unfortunately 5 to 10 [µm]. In particular, in the case of the sample 20 with no pattern, the positional reference cannot be identified. Accordingly, the error further increases.

In contrast, in this embodiment, as shown in FIG. 13, the sample 20 is mounted on the stage 30 in the same chamber 160 in two types of inspections. Even in the case where the stage 30 is moved between the mapping type electron column 100 and the SEM inspection apparatus 120, the same position can be highly accurately identified. Accordingly, even in the case of the sample 20 with no pattern, the position can be highly accurately identified. For instance, the position can be identified at an accuracy of 1 [μm] or less.

Such highly accurate identification is significantly advantageous in the following case. First, foreign matter inspection on the sample 20 with no pattern is performed according to the mapping method. The detected foreign matter 10 is then identified and observed (reviewed) in detail by the SEM inspection apparatus 120. Since the accurate position can be identified, not only presence or absence of the foreign matter 10 (pseudo-detection in the case of absence) can be determined but also the size and shape of the foreign matter 10 can be observed in detail at high speed.

As described above, the separate arrangement of the electron column 100 for detecting foreign matters and the SEM inspection apparatus 120 for reviewing takes much time for identifying the foreign matter 10. In the case of the sample with no pattern, the difficulty is increased. Such problems are solved by this embodiment.

As described above, in this embodiment, through use of the aperture imaging conditions for the foreign matter 10 according to the mapping optical system, a significantly fine foreign matter 10 can be highly sensitively detected. Furthermore, the mapping optical type electron column 100 and the SEM inspection apparatus 120 are mounted in the same chamber 160. Thus, in particular, inspection on the significantly fine foreign matter 10 with a dimension of 30 [nm] or less determination and classification of the foreign matter 10 can be performed significantly efficiently at high speed. This embodiment is also applicable to the aforementioned Embodiments 1 to 3 and embodiments to which no numeral is assigned.

Next, another example using both the mapping projection type inspection apparatus and the SEM will be described.

The above description has been made where the mapping projection type inspection apparatus detects the foreign matters and the SEM performs reviewing inspection. However, the present invention is not limited thereto. The two inspection apparatuses can be applied to another method. Combination of the inspection apparatuses can perform effective inspection. For instance, the other method is as follows.

In this inspection method, the mapping projection type inspection apparatus and the SEM inspect respective regions different from each other. Furthermore, the "cell to cell (cell to cell)" inspection is applied to the mapping projection type inspection apparatus, and the "die to die (die to die)" inspection is applied to the SEM. Accordingly, highly accurate inspection is effectively achieved as a whole.

More specifically, the mapping projection type inspection apparatus performs "cell to cell" inspection in a region with many repetitive patterns in the die. The SEM performs the "die to die" inspection in a region with a small number of repetitive patterns. Both inspection results are combined and one inspection result is acquired. The "die to die" inspection compares images of two dice that are sequentially acquired. The "cell to cell" inspection compares images of two cells that are sequentially acquired. The cell is a part of a die.

The inspection method performs high speed inspection using mapping projection on repetitive pattern portions while performing inspection on regions with a small number of repetitive patterns using the SEM that can achieve high accuracy and small number of artifacts. The SEM is not suitable to high speed inspection. However, since the region with a small number of repetitive patterns is relatively narrow, the inspection time by the SEM is not too long. Accordingly, the entire inspection time can be suppressed short. Thus, this inspection method can take advantage of the two methods at the maximum, and perform highly accurate inspection in a short inspection time.

Next, referring again to FIG. 27, the mechanism of conveying the sample 20 will be described.

The sample 20, such as a wafer or a mask, is conveyed through a load port into the mini-environment 180, and an alignment operation is performed in the environment. The sample 20 is conveyed to the load lock 162 by the conveyance robot in the atmosphere. The load lock 162 is evacuated from the atmosphere to a vacuum state by the vacuum pump. After the pressure becomes below a prescribed value (about 1 [Pa]), the sample 20 is conveyed by the conveyance robot in the vacuum disposed in the transfer chamber 161 from the load lock 162 to the main chamber 160. The sample 20 is mounted on the electrostatic chuck mechanism on the stage 30.

The sample 20, such as a wafer or a mask, is conveyed through a load port into the mini-environment 180, and an alignment operation is performed in the environment. The sample 20 is conveyed to the load lock 162 by the conveyance robot in the atmosphere. The load lock 162 is evacuated from the atmosphere to a vacuum state by the vacuum pump. After the pressure becomes below a prescribed value (about 1 [Pa]), the sample 20 is conveyed by the conveyance robot in the vacuum disposed in the transfer chamber 161 from the load lock 162 to the main chamber 160. The sample 20 is mounted on the electrostatic chuck mechanism on the stage 30.

Figure 14:
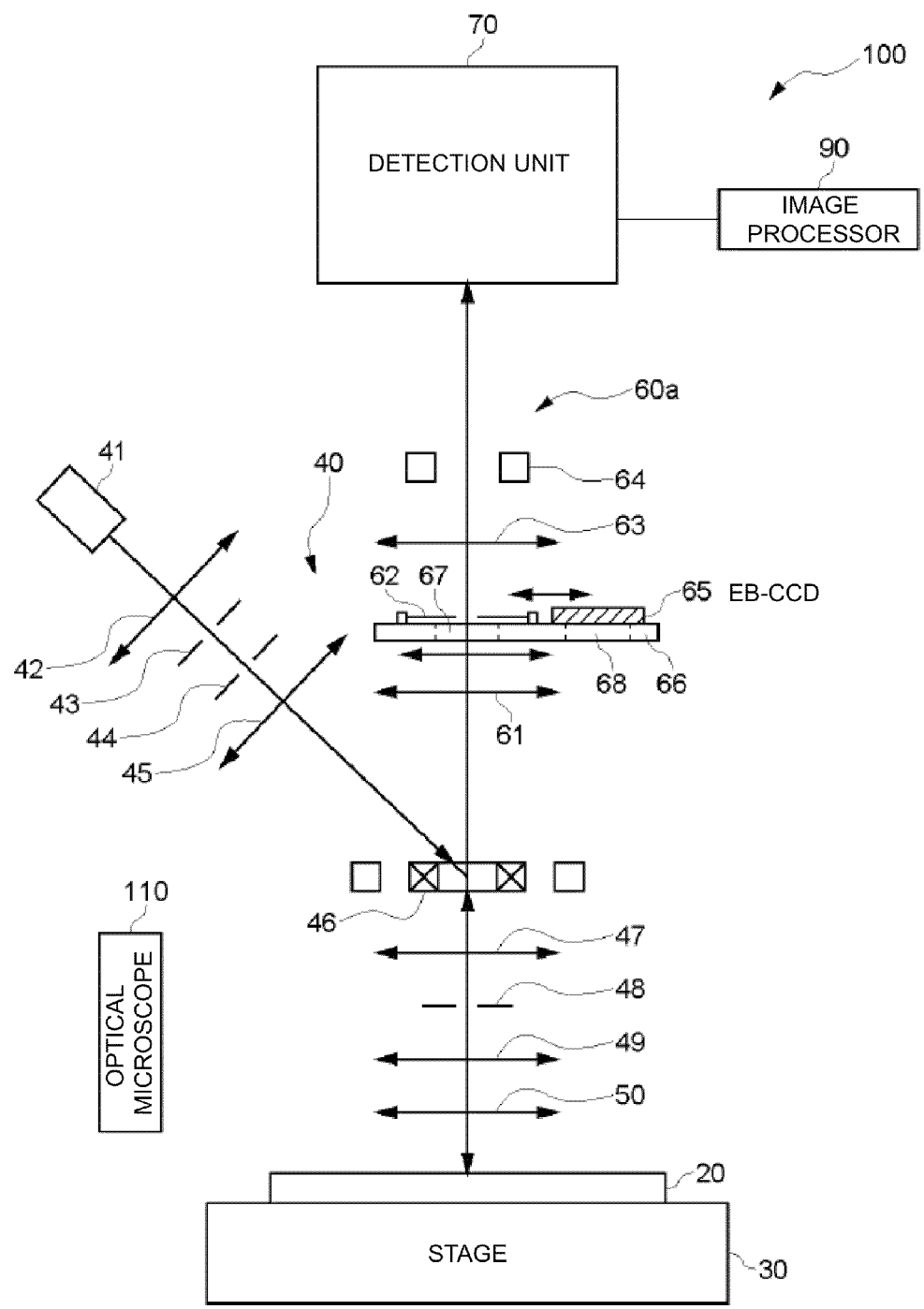
FIG. 14 is a diagram showing a configuration of an electron column system according to an embodiment of the present invention.

FIG. 14 shows the inside of a main chamber 160 and an electron column system 100 arranged on the top of the main chamber 160. Reference symbols similar to those of FIG. 11 are assigned to configurational components similar to those of FIG. 11. The description thereof is omitted.

A sample 20 is mounted on a stage 30 movable in X, Y, Z and θ directions. The stage 30 and an optical microscope 110 perform highly accurate alignment. A mapping projection optical system performs foreign matter inspection and pattern defect inspection of the sample 20 using an electron beam. Here, the potential of the sample surface 21 is important. In order to measure the surface potential, a surface potential measurement device capable of measurement in a vacuum is attached to the main chamber 160. The surface potential measurement device measures the two-dimensional surface potential distribution on the sample 20. On the basis of the measurement result, focus control is performed in a secondary optical system 60a that forms an electron image. A focus map of the two-dimensional positions of the sample 20 is created on the basis of the potential distribution. Inspection is performed while changing and controlling the focus under inspection. Accordingly, the blurring and aberrations of an image due to variation in circular potential on the surface according to the position can be reduced. Highly accurate and stable image acquisition and inspection can be achieved.

Here, the secondary optical system 60a is configured so as to be capable of measuring detected current of electrons incident on an NA aperture 62 and a detector 70. Furthermore, this system is configured such that an EB-CCD can be arranged on the position of the NA aperture 62. Such a configuration is significantly advantageous and effective. In FIG. 14, the NA aperture 62 and the EB-CCD 65 are arranged on a holding member 66 that integrally includes openings 67 and

68. The secondary optical system 60a is provided with a mechanism capable of independently performing current absorption of the NA aperture 62 and image acquisition of the EB-CCD 65. In order to achieve this mechanism, the NA aperture 62 and the EB-CCD 65 are arranged in the XY stage 66 movable in a vacuum. Accordingly, positional control and positioning can be performed on the NA aperture 62 and the EB-CCD 65. Since the stage 66 is provided with the openings 67 and 68, mirror electrons and secondarily emitted electrons can pass through the NA aperture 62 or the EB-CCD 65.

The operation of the secondary optical system 60a having such a configuration is described. First, the EB-CCD 65 detects the spot shape and the center position of a secondary electron beam. The voltages of a stigmator, lenses 61 and 63 and an aligner 64 are adjusted such that the spot shape becomes circular and the minimum. In relation to this point, conventionally, the spot shape and astigmatism cannot be directly adjusted at the position of the NA aperture 62. This embodiment can achieve such direct adjustment, and can highly accurately correct the astigmatism.

Furthermore, the center position of the beam spot can be easily detected. The position of the NA aperture 62 can be adjusted such that the center of the NA aperture 62 is arranged at the beam spot position. In relation to this point, conventionally, direct adjustment of the position of the NA aperture 62 cannot be performed. This embodiment can directly adjust the position of the NA aperture 62. Accordingly, the NA aperture can be highly accurately positioned, the aberration of an electron image is reduced, and uniformity is improved. Thus, transmittance uniformity is improved, thereby allowing an electron image having high resolution and uniform gradation to be acquired.

For inspection of a foreign matter 10, it is important to efficiently acquire a mirror signal from the foreign matter 10. Since the position of the NA aperture 62 defines the transmittance and aberration of the signal, this aperture is significantly important. Secondarily emitted electrons are emitted at a wide angle range from the sample surface according to the cosine law, and uniformly reach in a wide region at the NA position (e.g., $\phi 3$ [mm]). Accordingly, the secondarily emitted electrons are insensitive to the position of the NA aperture 62. On the contrary, the reflection angle of mirror electrons on the sample surface is almost equivalent to the incident angle of the primary electron beam. Accordingly, the mirror electrons represent a small divergence, and reach the NA aperture 62 with a small beam diameter. For instance, the divergent region of mirror electrons is one twentieth as wide as the divergent region of the secondary electron or less. Accordingly, the mirror electrons are significantly sensitive to the position of the NA aperture 62. The divergent region of the mirror electrons at the NA position is typically a region ranging from $\phi 10$ to 100 [µm]. Accordingly, it is significantly advantageous and important to acquire the position with the maximum mirror electron intensity and arrange the center position of the NA aperture 62 at the acquired position.

In order to achieve arrangement of the NA aperture 62 at such an appropriate position, according to a preferred embodiment, the NA aperture 62 is moved in X and Y directions in a vacuum in the electron column 100 at an accuracy about 1 [µm]. The signal intensity is measured while the NA aperture 62 is moved. The position with the maximum signal intensity is acquired, and the center of the NA aperture 62 is disposed at the acquired coordinate position.

The EB-CCD 65 is significantly advantageously used for measuring the signal intensity. This is because two-dimensional information on the beam can be acquired, the number of electrons entering the detector 70 can be acquired to thereby allow the signal intensity to be quantitatively evaluated.

Alternatively, the aperture arrangement may be defined and the condition of the lens 63 between the aperture and the detector may be configured, so as to achieve a conjugate relationship between the position of the NA aperture 62 and the detection surface of the detector 70. This configuration is also significantly advantageous. Thus, an image of a beam at the position of the NA aperture 62 is formed on the detection surface of the detector 70. Accordingly, a beam profile at the position of the NA aperture 62 can be observed using the detector 70.

The NA size (aperture diameter) of the NA aperture 62 is also important. The signal region of mirror electrons is small as described above. Accordingly, an effective NA size ranges from about 10 to 200 [µm]. Furthermore, it is preferred that the NA size be larger by +10 to 100 [%] than the beam diameter.

In relation to this point, the image of electrons is formed of mirror electrons and secondarily emitted electrons. The foregoing setting of the aperture size can further increase the ratio of mirror electrons. Accordingly, the contrast of the mirror electrons can be increased. That is, the contrast of the foreign matter 10 can be increased.

Now, description will be made in further detail. If the aperture is made small, the secondarily emitted electrons decrease in inverse proportion to the area of the aperture. Accordingly, the gradation of a normal portion becomes small. However, the mirror signal does not change, and the gradation of the foreign matter 10 does not change. Thus, the contrast of the foreign matter 10 can be increased by as much as reduction in gradation therearound, and a high S/N can be achieved.

The aperture may be configured such that the position of the aperture can be adjusted not only in the X and Y directions but also in the Z axis direction. This configuration is also advantageous. The aperture is preferably arranged at a position where the mirror electrons are most narrowed. Accordingly, reduction in the aberration of the mirror electrons and secondarily emitted electrons can be significantly effectively achieved. A higher S/N can therefore be achieved.

As described above, the mirror electrons are significantly sensitive to the NA size and the shape thereof. Accordingly, appropriate selection of the NA size and the shape thereof is significantly important to achieve a high S/N. An example of a configuration for selecting such an appropriate NA size and the shape thereof is hereinafter described. Here, the shape of the aperture (hole) of the NA aperture 62 is also described.

Here, the NA aperture 62 is a member (component) having a hole (opening). Typically, the member is sometimes referred to as an aperture, and the hole (opening) is sometimes referred to as an aperture. In the following description related to the aperture, the member is referred to as an NA aperture in order to discriminate the member (component) from the hole. The hole of the member is referred to as an aperture. The aperture shape is typically referred to as the shape of a hole.

<Inspection Apparatus>

An inspection apparatus of this embodiment of the present invention is described with reference to the drawings. In this embodiment, the case of application to a semiconductor inspection apparatus and the like is exemplified.

As described above, the inspection apparatus of this embodiment includes: beam generation means for generating any of charged particles or electromagnetic waves as a beam; a primary optical system that irradiates, with the beam, an inspection object held on a movable stage in a working chamber; a secondary optical system that detects secondary charged particles emitted from the inspection object; and an image processing system that forms an image on the basis of the detected secondary charged particles.

Here, terms, such as secondary charged particles and mirror electrons, are described. "Secondary charged particles" include a part or mixture of secondarily released electrons, mirror electrons, and photoelectrons. In the case of irradiation with electromagnetic waves, photoelectrons occur from the surface of the sample. When the surface of the sample is irradiated with charged particles, such as electron beam, "secondarily released electrons" occur from the surface of the sample, or "mirror electrons" are formed. The "secondarily released electrons" are caused by collision of an electron beam with the surface of the sample. That is, the "secondarily released electrons" are a part or mixture of the secondary electrons, the reflected electrons, and the backscattering electrons. "Mirror electrons" are the emitted electron beam that does not collide with the surface of the sample and is reflected in proximity to the surface.

Figure 15:
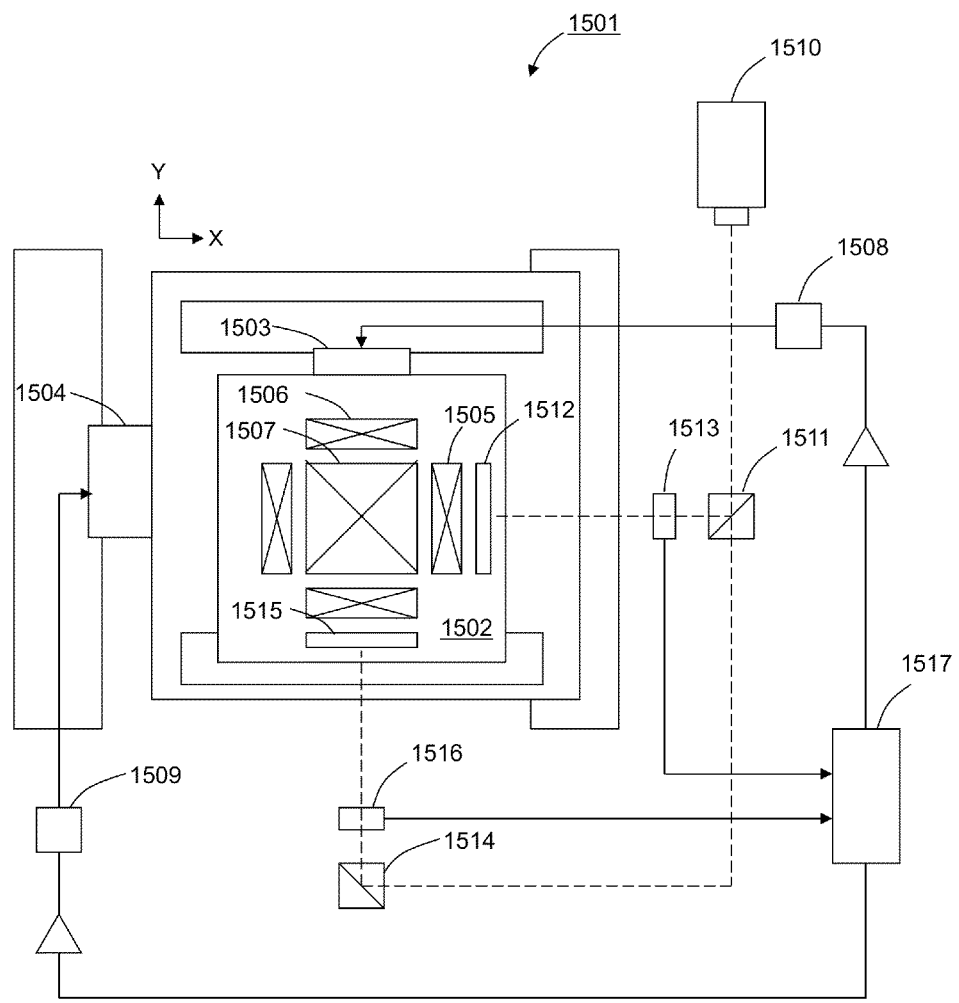
FIG. 15 is a diagram (plan view) illustrating a main part of an inspection apparatus according to an embodiment of the present invention.
Figure 16:
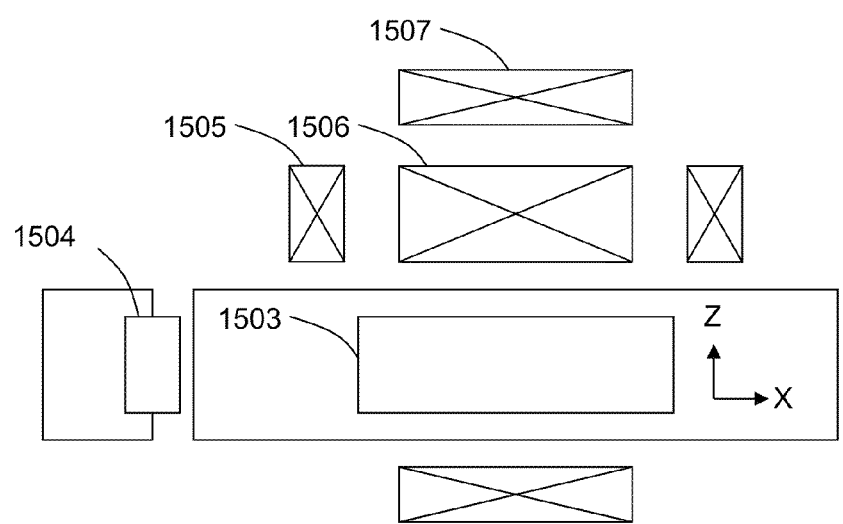
FIG. 16 is a diagram (side view) illustrating the main part of the inspection apparatus according to the embodiment of the present invention.

Next, referring to FIGS. 15 and 16, the configuration of the inspection apparatus of this embodiment is described in detail. As described in FIGS. 15 and 16, an inspection apparatus 1501 includes: a linear motor 1503 that moves a movable stage 1502 in the X direction; and a linear motor 1504 that moves a movable stage 2 in the Y direction. The inspection apparatus 1501 further includes an Helmholtz coil 1505 that generates magnetic fields in the X direction, a Helmholtz coil 1506 that generates magnetic fields in the Y direction, and a Helmholtz coil 1507 that generates magnetic fields in the Z direction, to cancel the magnetic fields generated by linear motors 3 and 4 when the movable stage 2 is driven.

The inspection apparatus 1501 further includes: a current detector 1508 that detects a drive current for driving the linear motor 1503 in the X direction; and a current detector 1509 that detects a drive current for driving the linear motor 1504 in the Y direction.

The inspection apparatus 1501 further includes a laser oscillator 1510, a mirror 1511, a stage mirror 1512 in the X direction, and an interferometer 1513, as a configuration for detecting the stage position of the mobile stage in the X direction. The inspection apparatus 1501 further includes a laser oscillator 1510, a mirror 1514, a stage mirror 1515 in the Y direction, and an interferometer 1516, as a configuration for detecting the stage position of the mobile stage in the Y direction.

The inspection apparatus 1501 further includes a magnetic field controller 1517. The magnetic field controller 1517 controls the intensities of magnetic fields to be generated by the Helmholtz coils 1505, 1506 and 1507 according to the drive currents detected by the current detectors 1508 and 1509 and the stage positions detected by the interferometers 1513 and 1516.

Figure 17:
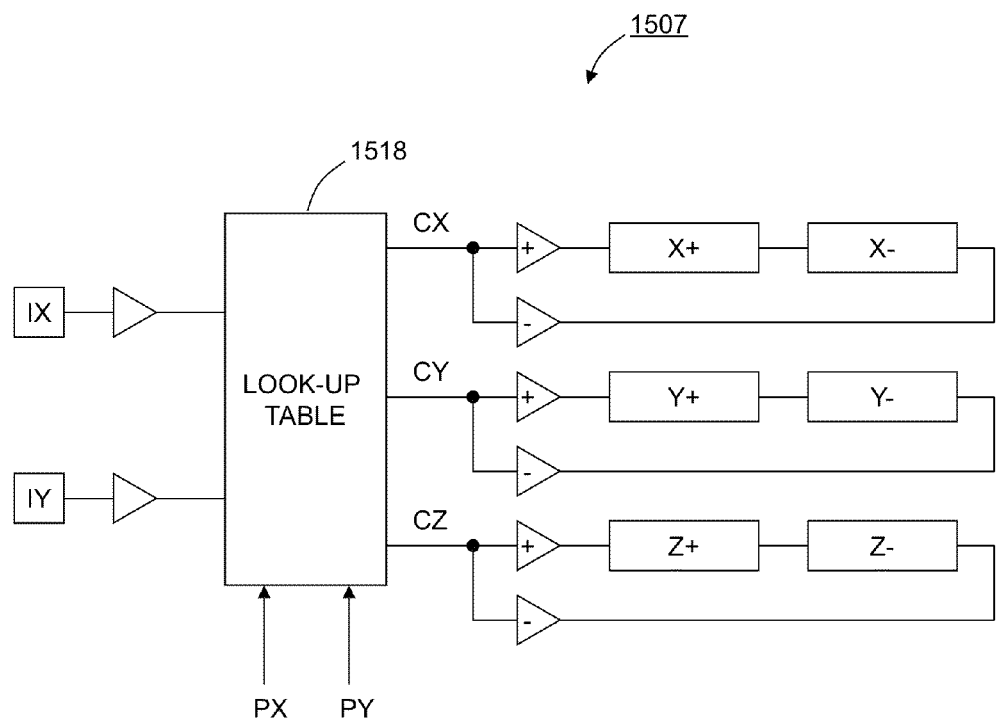
FIG. 17 is a diagram illustrating magnetic field control means according to the embodiment of the present invention.

Here, referring to FIG. 17, the configuration of the magnetic field controller 1517 is described in detail. The magnetic field controller 1517 includes a look-up table 1518. The drive currents IX and IY detected by the current detectors 1508 and 1509 and the stage positions PX and PY detected by the interferometers 1513 and 1516 are input into the look-up table 1518. The look-up table 1518 stores compensation values CX, CY and CZ for the drive currents IX and IY and the stage positions PX and PY.

Figure 18A:
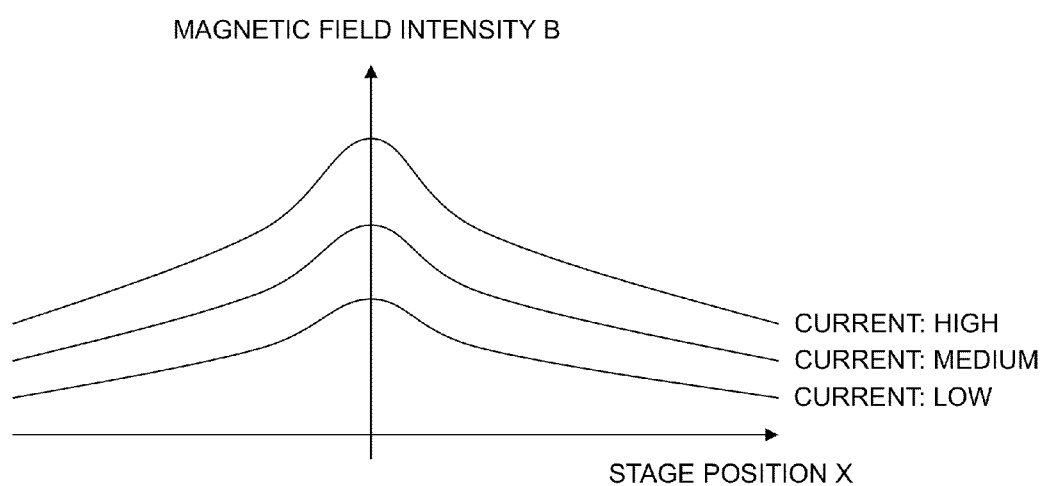
FIG. 18A is a diagram illustrating a magnetic field intensity (the intensity of a magnetic field generated by a linear motor) according to the embodiment of the present invention.
Figure 18B:
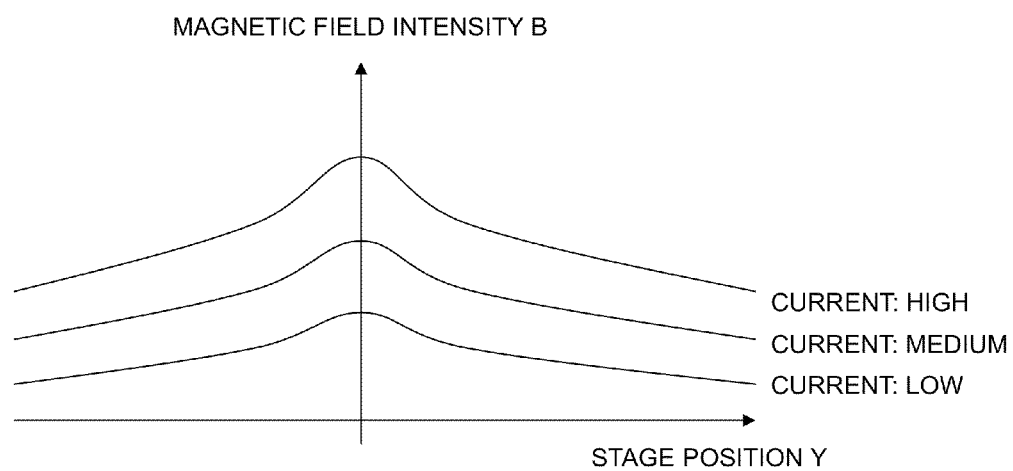
FIG. 18B is a diagram illustrating a magnetic field intensity (the intensity of a magnetic field generated by a linear motor) according to the embodiment of the present invention.

The compensation values CX, CY and CZ are preliminarily acquired by installing a three-axis (three-dimensional) magnetic field sensor adjacent to the beam center position on the movable stage 1502, moving the movable stage 1502, and measuring the magnetic field intensities (magnetic field intensities to be compensated) generated by the linear motors (see FIGS. 18A and 18B).

For instance, the compensation values CX, CY and CZ are represented by the following expressions. Here, coefficients (mixture ratios) ±A to ±F are variable according to stage positions PX and PY.

$$CX = \pm A \cdot IX \pm B \cdot IY$$

$$CY = \pm C \cdot IX \pm D \cdot IY$$

$$CZ = \pm E \cdot IX \pm F \cdot IY$$

Next, a method of creating a look-up table (a method of determining the values of the look-up table) is described.

The intensity of the magnetic field at the observation center is defined by the magnitude of coil current in the linear motors, which are generation sources of magnetic fields, the magnetic forces of the linear motors (magnetic forces which the magnets of the linear motors have), and the positions from the magnets of the linear motors.

The magnetic forces of the linear motors macroscopically vary according to time and temperature. However, it is sufficient to perform calibration on all such occasions. Accordingly, the forces can be considered substantially constant. Meanwhile, the coil currents vary according to the speed and load situations. The magnetic fields generated by the coils are in proportion to the coil current.

Thus, the magnetic fields affecting the observation point is a total sum of the fields generated by the magnets of the linear motors and the fields generated by the coils.

For instance, a magnetic field sensor sensitive in the XYZ directions is installed adjacent to the observation center. First, stage coordinates are divided by multiple points in the XY directions. The stage is moved to the points, and stopped. In a condition where the coil currents are isolated, the magnetic fields in the XYZ directions are then measured. This measurement a) acquires the magnetic field intensity a' at each point due to the magnetic field of the linear motors.

Next, the stage is moved at a constant speed in the XY directions, or accelerated or decelerated at the multiple points. Drive currents are caused to flow through the XY linear motors, and the magnetic field at each point (each coordinate) is measured. In the measurement b), the measurement results of the magnetic fields at the same coordinates as those in the measurement a) include the result measured by the measurement a) and effects of the coil currents superimposed thereon. Accordingly, a result acquired by subtracting the values measured by the measurement a) from the values measured by the measurement b) represents the effects of the coil currents at each point. Thus, magnetic field intensity b' at each point affected by the coil currents is acquired. At the same time, the coil current I' at this time is recorded. The magnetic field intensity b' is in proportion to the coil current I' (b'=b"×I').

As described above, the magnetic fields X, Y and Z at each stage point are acquired. The correction value at each point is acquired. For instance, the correction value at coordinates X0 and Y0 is $a'_{X0,Y0} \pm I \cdot b''_{X0,Y0}$, where $a'_{X0,Y0}$ is the value of a' at the coordinates X0 and Y0, I is a coil current value (present value), and $b''_{X0,Y0}$ is the value of b" at the coordinates X0 and Y0. The look-up table stores the values of these $a'_{X0,Y0}$ and $b''_{X0,Y0}$.

In the case of actual measurement, the value of the look-up table is read for each of the stage coordinates. The values of current flowing through the linear motors are substituted into I. Currents are caused to flow through the Helmholtz coils so as to cancel the magnetic fields.

Note that, at the coordinates other than those of points where the magnetic fields are preliminarily measured (measurement points), interpolation may be performed on the basis of the data at observation points adjacent thereto. Measurement on the magnetic fields may be performed, for instance, on shipment of the inspection apparatus and during maintenance.

Such an inspection apparatus of this embodiment of the present invention adopts linear motors as drive sources for driving the movable stage. Accordingly, reduction in cost of the apparatus can be achieved. In this case, the magnetic fields caused by the linear motors during driving of the movable stages are canceled by the magnetic fields caused by the Helmholtz coils. Accordingly, adverse effects of the magnetic fields caused by the linear motors to the beam of charged particles or electromagnetic waves can be suppressed.

Furthermore, this embodiment of the present invention controls the intensities of magnetic fields generated by the Helmholtz coils according to the drive currents for driving the linear motors and the position of the movable stage. Accordingly, the intensities of the magnetic fields caused by the Helmholtz coils can be appropriately controlled so as to cancel the magnetic fields caused by the linear motors.

(Second Aspect)

Hereinafter, referring to the drawings, an embodiment for implementing the present invention (second aspect) is described.

Figure 19:
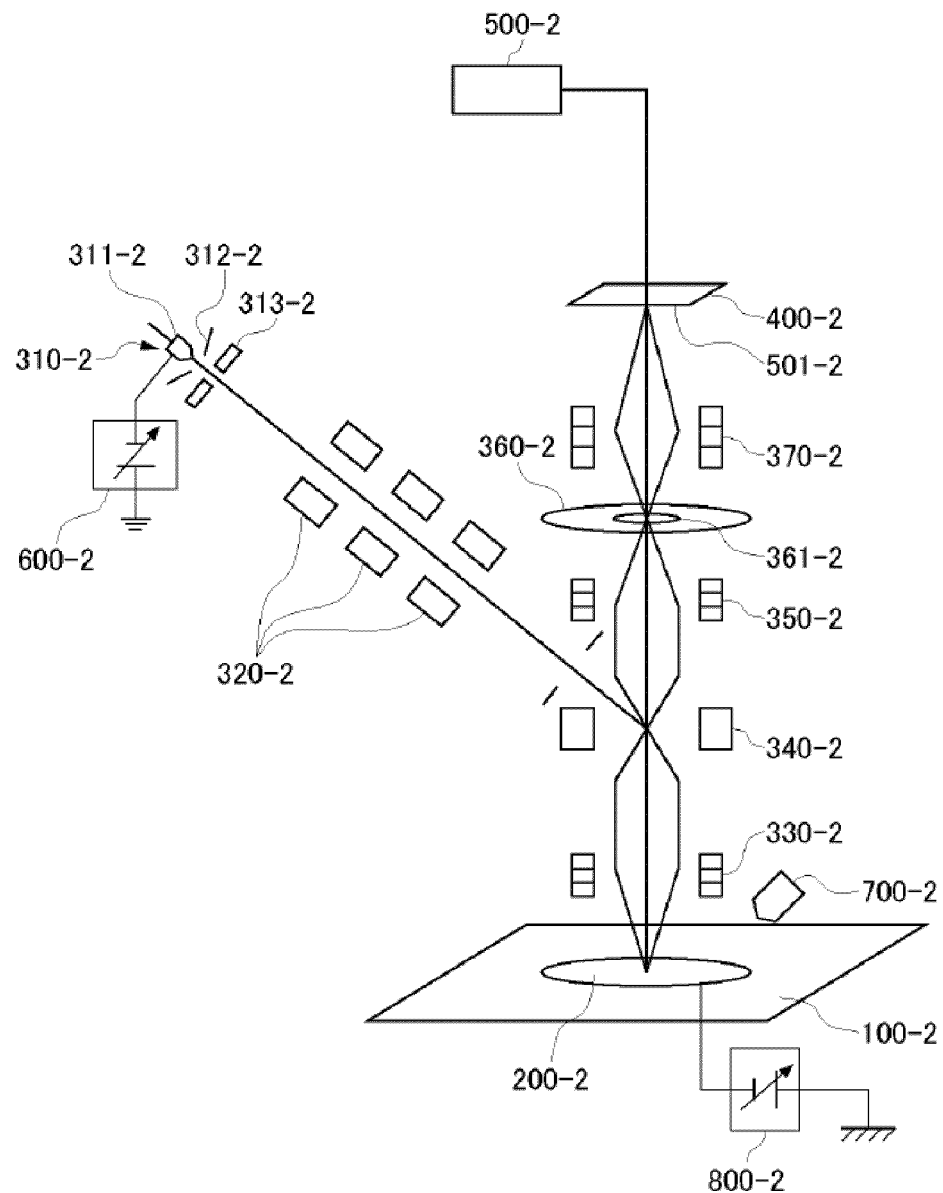
FIG. 19 is a diagram showing an overview of the inspection apparatus as an example to which the present invention is applicable.

FIG. 19 is a diagram showing an overview of an example of the entire configuration of an electron beam inspection apparatus to which the present invention is applicable. The electron beam inspection apparatus is a mapping projection type low acceleration electron beam apparatus, and includes an electron beam source 310-2, a primary system lens 320-2, a condenser lens 330-2, electromagnetic field generation means (E×B) 340-2, a transfer lens 350-2, an NA adjusting aperture plate 360-2 for adjusting a numerical aperture (NA), a projection lens 370-2, a detector 400-2, an image processor 500-2, a stage 100-2 on which a sample 200-2 to be an observation object is mounted, and an irradiation energy setting supplier 600-2.

The NA adjusting aperture plate 360-2 is provided with at least one NA aperture 361-2. This NA aperture 361-2 defines the numerical aperture (NA). The position of the NA aperture 361-2 can be adjusted in a plane. This NA aperture can selectively guide, to the detector 400-2, electrons including structure information that is on the conductive region and has a different directivity according to the effect of the after-mentioned E×B 340-2, and electrons including structure information on the insulative region. The electron beam inspection apparatus may have a configuration including charged beam irradiation means 700-2 for irradiating the surface of the sample 200-2 with an electron beam to charge this sample surface, if necessary.

The surface of the sample 200-2 includes insulative regions and conductive regions. The sample surface is observed through irradiation with an electron beam from the electron beam source 310-2. The electron beam source 310-2 includes, for instance, an electron source 311-2, a Wehnelt electrode 312-2, and an anode 313-2. The electron source 311-2 generates electrons. The Wehnelt electrode 312-2 extracts the electrons. The anode 313-2 accelerates the electrons, which is emitted toward the sample surface.

The electron beam source 310-2 may be configured so as to generate a planer electron beam having a prescribed area that can accommodate multiple pixels and allows the multiple pixels to be simultaneously image-taken. Accordingly, one time of irradiation with an electron beam on the sample surface can simultaneously take the multiple pixels, and acquire a two-dimensional image having a large area at a high speed.

The irradiation energy setting means 310-2 is means for setting the irradiation energy of an electron beam to be emitted from the electron beam source 310-2. The irradiation energy setting supply means 310-2 includes a variable voltage source with a negative pole connected to an electron source, and supplies power to the electron beam source 310-2 to cause the electron source 311-2 to emit electrons. The irradiation energy of the electron beam is defined by the difference between the potential of the sample 200-2 and the potential of the cathode included in the electron source 311-2 of the electron beam source 310-2. Accordingly, the irradiation energy setting supplier 600-2 can adjust and set the irradiation energy by adjusting the voltage of the variable voltage source (hereinafter, referred to as an "acceleration voltage").

In the electron beam inspection apparatus according to the present invention, the irradiation energy of the electron beam is set to have an appropriate value by the irradiation energy setting supplier 600-2, thereby increasing the contrast of the acquired image. According to the present invention, the irradiation energy of the electron beam is set in a transition region where electrons having structure information on the surface of the sample 200-2 due to irradiation with the imaging electron beam include both mirror electrons and secondary electrons. A specific method of setting the irradiation energy will be described later.

The primary system lens 320-2 is means for deflecting the electron beam emitted from the electron beam source 310-2 due to the effect of the electromagnetic field and guiding the electron beam to a desired irradiation region on the surface of the sample 200-2. Note that the primary system lens 320-2 may be multiple lenses or one. For instance, a quadrupole lens is adopted as each primary system lens 320-2.

The E×B (E×B deflector) 340-2 is means for applying an electric field and magnetic field to an electron beam or electrons and directing the electron beam or the electrons by a Lorentz force in a prescribed direction. The E×B 340-2 sets the electric field and the magnetic field so as to cause a Lorentz force for directing the electron beam emitted from the electron beam source 310-2 toward the surface of the sample 200-2.

The E×B 340-2 sets the electric field and the magnetic field so as to allow the electrons including the structure information on the sample surface acquired by irradiation on the sample surface with the electron beam to travel upward as they are toward the detector 400-2. As described below, the electrons including the structure information on the sample surface acquired by irradiation with the imaging electron beam are directed by the electric field and the magnetic field according to the speed of traveling in a direction opposite to the incident direction of the electron beam due to the effect of the E×B 340-2.

The effect of the E×B 340-2 can separate the electron beam incident on the sample surface from electrons caused from the sample surface and traveling in the direction opposite to the direction of the incident electron beam. Note that E×B may be referred to as a Wien filter.

The condenser lens 330-2 is a lens for image-forming an electron beam on the surface of the sample 200-2 and converging the electrons including the structure information on the sample surface. Thus, the condenser lens 330-2 is arranged closest to the sample 200-2.

The transfer lens 350-2 is optical means for directing the electrons having passed through the E×B 340-2 in the direction toward the detector 400-2 to form a crossover around the NA aperture 361-2 of the NA adjusting aperture plate 360-2.

The NA adjusting aperture plate 360-2 is means for adjusting the number of passed electrons. The NA adjusting aperture plate 360-2 has the NA aperture 361-2 that is a hole defining the numerical aperture (NA), at the center. The NA aperture 361-2 allows the electrons guided by the transfer lens 350-2 from the sample surface to pass to thus configure a path to the detector 400-2, and blocks electrons to be noise for imaging so as not to travel toward the detector 400-2, thereby adjusting the number of passed electrons. As described above, the position of the NA aperture 361-2 can be adjusted in the plane. This NA aperture can selectively guide, to the detector 400-2, electrons including structure information on the conductive region and electrons including structure information on the insulative region that have different directivities, by means of the effect of the E×B 340-2. The details thereof will be described later. Note that multiple types of NA apertures 361-2 having different hole diameters may be provided. In this case, an NA aperture having a desired hole diameter is selected by an NA aperture moving mechanism (not shown).

The projection lens 370-2 is final focus adjusting means for image-forming electrons having passed through the NA adjusting aperture 361-2, on the detection surface of the detector 400-2.

The detector 400-2 is means for detecting electrons including the structure information on the sample surface, which has been irradiated with the electron beam, and acquiring an image of the sample surface. Any of various detectors may be adopted as the detector 400-2. For instance, any of a CCD (charge coupled device) detector and a TDI (time delay integration)-CCD detector, which are capable of acquiring images in parallel, may be adopted. The two-dimensional imaging detector 400-2, such as a CCD or a TDI-CCD, is adopted, and the electron beam source 310-2 adopts a planer beam with which a prescribed area including multiple pixels can be irradiated, thereby allowing acquisition of an image for a wide area taken by parallel imaging through beam irradiation on one site and, in turn, enabling the sample surface to be observed at a high speed. Note that the CCD and the TDI-CCD are detection elements that detect light and output electric signals. Thus, adoption of a CCD or a TDI-CCD as the detector 400-2 requires a fluorescent plate for converting electrons into light, and an MCP (microchannel plate) for amplifying electrons. Accordingly, the detector 400-2 is configured to include these elements.

An EB-CCD or an EB-TDI may be adopted as the detector 400-2. An EB-CCD and an EB-TDI are the same as a CCD and a TDI-CCD in that these elements are two-dimensional imaging detectors, but directly detect electrons and output electric signals as they are without light-electrons conversion. Accordingly, the aforementioned fluorescent plate or MCP is not required, which reduces signal loss in any possible intermediate process, thereby enabling an image with high resolution to be taken.

The image processor 500-2 is a device that stores electric signals output from the detector 400-2, and generates an image of the surface of the sample 200-2 on the basis of the stored signals. More specifically, this device generates a two-dimensional image on the basis of coordinate information and luminance information output from the detector 400-2. In order to observe the sample 200-2 containing insulation material and conductive material at the surface, it is preferable that a difference between the luminances in the insulative region and the conductive region occur to take an image with high contrast. Thus, the image processor 500-2 performs required image processes and image generation in order to acquire a favorable image.

The stage 100-2 is means for allowing the sample 200-2 to be mounted on the top surface of this means and supporting the sample 200-2. The stage 100-2 is movable in the X direction and the Y direction in a plane (XY plane) and rotatable in the plane such that the entire region of the sample surface 201-2 to be observed can be irradiated with the electron beam. Furthermore, this stage may be movable in the vertical direction (Z direction) to adjust the height of the surface of the sample 200-2, if necessary. In the case where the stage 100-2 is configured to be movable, moving means, e.g., a motor, air or the like, may be provided.

The charged electron beam irradiation means 700-2 is provided for charging the sample 200-2 before irradiation with imaging electron beam for taking an image from the electron beam source 310-2. The charged electron beam irradiation means 700-2 may be provided, if necessary. If the sample surface is preliminarily irradiated with an electron beam before imaging of the sample surface, the conductive region is not charged and the potential remains to be the ground potential but the insulative region is negatively charged. Accordingly, a potential difference can be formed between the conductive region and the insulative region according to the materials. This potential difference can increase the contrast between the conductive region and the insulative region. Accordingly, in the case where the sample surface is desired to be irradiated with the charged electron beam before irradiation with the imaging electron beam, it is preferred to provide the charged electron beam irradiation means 700-2.

The charged electron beam irradiation means 700-2 is not necessarily provided in a separated manner. Alternatively, the electron beam source 310-2 may be configured to also serve as charged electron beam irradiation means. That is, the charged electron beam may be emitted from the electron beam source 310-2 without use of the charged electron beam irradiation means 700-2. Subsequent to the irradiation with the charged electron beam, the surface of the sample 200-2 may be irradiated with an electron beam for taking an image.

Accordingly, the charged electron beam irradiation means 120-2 may be provided, for instance, in the case where the sample surface 201-2 is desired to be irradiated with the charged electron beam and then with the electron beam for taking an image immediately after the irradiation of the charged electron beam. Typically, the imaging electron beam and the charged electron beam have different irradiation energies. Accordingly, the charged electron beam irradiation means 700-2 is thus provided, thereby negates the need of adjusting the irradiation energies between irradiation with the charged electron beam and the irradiation with the imaging electron beam and achieving quick imaging. Therefore, in the case where reduction in observation time and the like is highly demanded, this demand for reduction in observation time can be satisfied by providing the charged electron beam irradiation means 700-2.

The surface of the sample 200-2 typically includes an insulative region made of insulation material and a conductive region made of conductive material. The sample 200-2 may have any of various shapes. For instance, a substrate-shaped sample, such as a semiconductor wafer or a reticle, may be adopted. It is preferred that the electron beam inspection apparatus according to the present invention be configured to favorably observe the sample surface even in the case where the insulative region of the sample surface has a higher area ratio than the conductive region. According to such a configuration, an image of the sample surface can be favorably taken and observation can be performed even in the case of a contact plug of a semiconductor wafer and the case of a contact structure of a reticle.

The conductive material and the insulation material may be made of any of various materials. For instance, the conductive material may be made of a plug material, such as W (tungsten), and the insulation material may be made of $SiO_2$ (silicon oxide film) or the like that is adopted as an insulation layer of a semiconductor wafer.

The electron beam inspection apparatus in FIG. 19 is a mapping projection type electron beam inspection apparatus, as described above. The electron beam inspection apparatus of the present invention may be an SEM type electron beam inspection apparatus.

Figure 20:
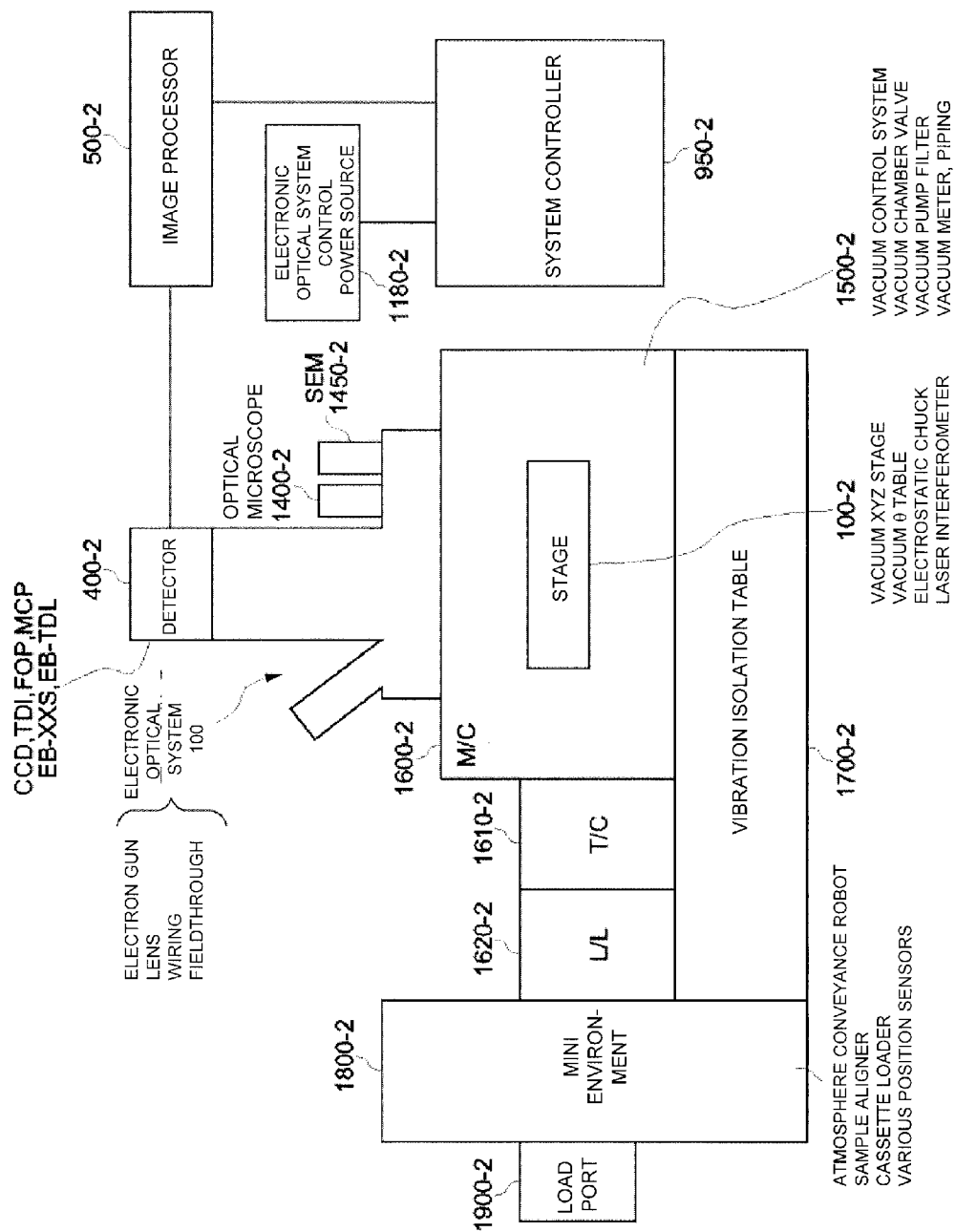
FIG. 20 is a diagram showing an overview of a sample observation system of First Embodiment to which the present invention is applicable.

FIG. 20 is a diagram showing an example of an overall configuration of a sample observation system (inspection system) of First Embodiment including an electron beam inspection apparatus according to the present invention. This sample observation system is configured to be a combined sample observation system that can observe a sample using a mapping projection type electronic optical system and an optical microscope and observe a sample using an SEM type electronic optical system.

The combined sample observation system shown in FIG. 20 includes a sample carrier 1900-2, a mini-environment 1800-2, a load lock 1620-2, a transfer chamber 1610-2, a main chamber 1600-2, a mapping projection type electron column 1300-2, and an image processor 500-2. The mini-environment 1800-2 is provided with an atmosphere conveyance robot, a sample alignment device, a clean air providing mechanism and the like (not shown). The transfer chamber 1610-2, which is always in a vacuum state, is provided with a vacuum conveyance robot (not shown), which can suppress occurrence of particles or the like due to variation in pressure to the minimum.

The main chamber 1600-2 is provided with a stage 100-2 movable in the X direction, the Y direction and the θ (rotational) direction on a horizontal plane (in XY plane). An electrostatic chuck (120-2 in FIG. 21) is provided on the stage 100-2. A sample itself or a sample in a state of being arranged on a pallet or a jig is mounted on the stage 100-2 by means of the electrostatic chuck.

The inside of the main chamber 1600-2 is subjected to pressure control so as to maintain a vacuum state by means of a vacuum control system 1500-2. The main chamber 1600-2, the transfer chamber 1610-2 and the load lock 1620-2 are mounted on a vibration isolation table 1700-2 to achieve a configuration for preventing vibrations from the floor from being transmitted.

The electron column 1300-2 is provided in the main chamber 1600-2. The electron column 1300-2 is provided with a primary optical system including the electron beam source 310-2 and the primary system lens 320-2 shown in FIG. 19, a secondary optical system including the condenser lens 330-2, the ExB 340-2, the transfer lens 350-2, the NA adjusting aperture plate 360-2 and the projection lens 370-2, and the detector 400-2 that detects secondary electrons from the sample 200-2 and mirror electrons. Furthermore, an optical microscope 1400-2 used for positioning the sample and an SEM 1450-2 used for review observation are provided as configurational components related to the electron column 1300-2.

Signals from the detector 400-2 are transmitted to the image processor 500-2 and subjected to signal processing thereat. The signal processing can perform both an on-time observation process and an off-line process for acquiring only an image and subsequently processing the image. The data processed by the image processor 500-2 is stored in a recording medium, such as a hard disk or a memory. The data can be displayed on a monitor of a console, if necessary. For instance, the data is displayed as an observation region, a defect map, a defect classification, a patch image, or the like. In order to achieve such signal processing, a system controller 950-2 is provided. The electron column system 1300-2 is provided with an electronic optical system control power source 1180-2 to supply a power source. The electronic optical system control power source 1180-2 includes the power source 600-2 for supplying power to the electron source 311-2 of the electron beam source 310-2, and irradiation energy control means for controlling the power source. This power source further includes a power source for setting the potential of a sample and control means therefor, which will be described later, and a source of a voltage to be supplied to a dust collecting electrode and control means therefor, which will be described later.

Next, a sample conveying mechanism is described. A sample, such as a wafer or a mask, is conveyed from a load port 1900-2 into the mini-environment 1800-2, in which alignment operation is performed. Furthermore, the sample is conveyed to the load lock 1620-2 by the atmosphere conveyance robot. In the load lock 1620-2, air is exhausted by a vacuum pump (not shown) from an atmospheric state to a vacuum state. After this exhaust causes the inside of the load lock 1620-2 to be at a certain pressure (e.g., about 1 Pa) or less, the sample is conveyed from the load lock 1620-2 to the main chamber 1600-2 by the vacuum conveyance robot provided for the transfer chamber 1610-2, and mounted on an electrostatic chuck mechanism included on the stage 100-2.

In the system in FIG. 20, the sample 200-2 is mounted on the stage 100-2, which is shared by the mapping projection type electron beam apparatus, i.e., the electronic optical system 1300-2, and the SEM type electronic optical system 1450-2. Accordingly, when the sample 200-2 is moved between the mapping projection type electronic optical system 1300-2 and the SEM type electronic optical system 1450-2, the coordinate relationship is uniquely acquired, and the same portion is easily identified at a high accuracy.

That is, in the case of moving the sample between different inspection apparatuses separated from each other, the sample is required to be arranged on different stages and thus the sample is required to be aligned in a separated manner. Even with such sample alignment, the identification error for the same site is unfortunately 5 to 10 μm or more. Particularly, in the case of a sample without any pattern, a positional reference cannot be identified. Accordingly, the error is further increased.

According to this example, even in the case of moving the sample 200-2 between the mapping projection type electronic optical system 1300-2 and the SEM type electronic optical system 1450-2, the same site can be highly accurately identified. Thus, a site can be highly accurately identified. For instance, an accuracy of 1 μm or less can be achieved. Accordingly, this identification is significantly effective to the case of inspecting a pattern and pattern defects using the mapping projection type electronic optical system 1300-2, and the case of identification of and detailed observation (review) on the detected defects through use of the SEM type electronic optical system 1450-2. That is, since a site can be identified, not only presence and absence can be identified (false detection in the case of absence) but also the accurate sizes and shapes of defects can be identified at a high speed. In the case of separate apparatuses, it takes much time to identify pattern defects.

The present invention adopts the system where the mapping projection type and SEM type electronic optical systems are mounted on the same chamber. Accordingly, in particular, a significantly fine pattern of 100 nm or less can be efficiently inspected, detected and classified at a high speed.

Figure 21:
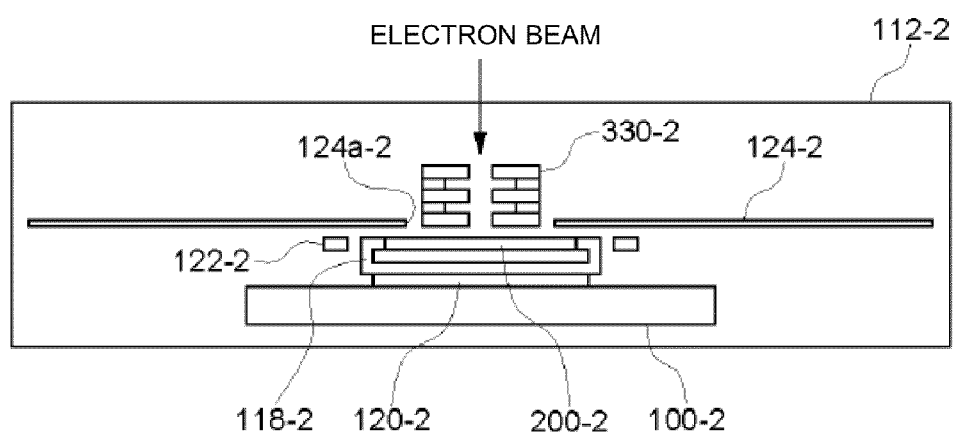
FIG. 21 is a longitudinal sectional front view showing an overview of a main part of an inspection apparatus of an embodiment of the present invention.
Figure 22:
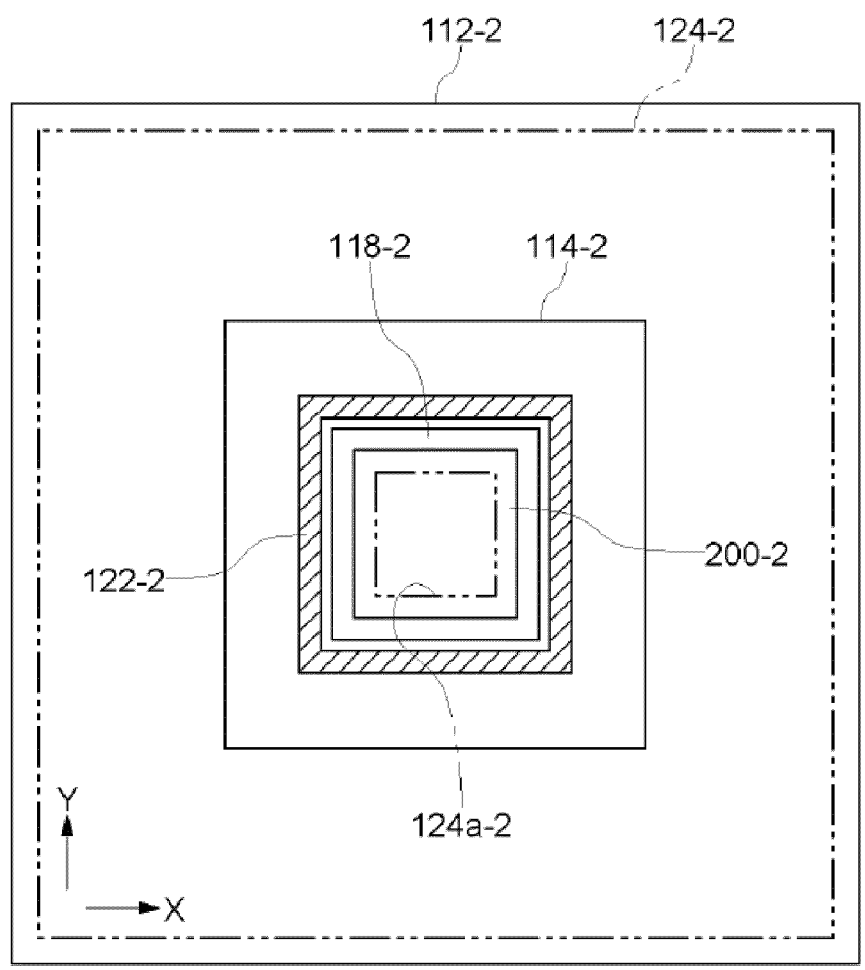
FIG. 22 is a cross-sectional plan view of FIG. 21 and a plan view showing a relationship between a stage, a sample and a dust collecting electrode of First Embodiment.
Figure 23:
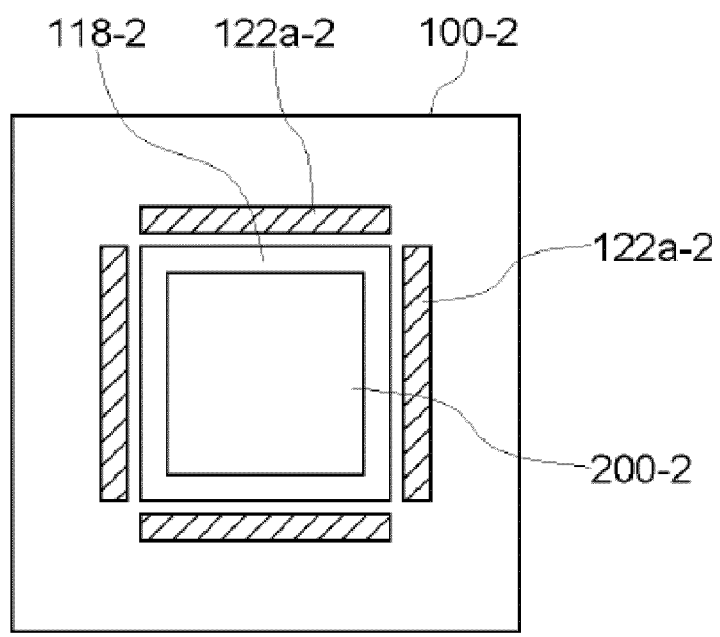
FIG. 23 is a plan view showing a relationship between a stage, a sample and a dust collecting electrode of Second Embodiment according to an embodiment of the present invention.

Next, referring to FIGS. 21 to 23, a configuration according to the present invention for preventing foreign matters, such as particles, from adhering to the sample surface is described in detail. In the following example, a rectangular-shaped mask or a circular-shaped semiconductor wafer that includes a surface layer made of a conductive thin film, e.g., a thin film made of Si (doping is also allowed), Cr, TaN, TaBN, CrN, Ru, Ta, W, Cu or the like is used as the sample 200-2. The outermost surface of the thin film may be an insulating film, such as of TaBO, TaO or $SiO_2$. For instance, a quartz substrate and a thin film that is formed thereon, or an Si wafer and a circuit pattern film structure for an LSI that is formed thereon is adopted as a mask.

FIG. 21 is a longitudinal sectional front view showing the stage 100-2 of the electron beam inspection apparatus according to the present invention shown in FIG. 19 and portions therearound in detail. FIG. 22 is a cross-sectional plan view of FIG. 21. As shown in FIGS. 21 and 22, the electron beam inspection apparatus according to the present invention includes a vacuum chamber 112-2 capable of being evacuated to a vacuum. The stage 100-2 movable in the X direction and the Y direction is arranged in the vacuum chamber 112-2. A holder 118-2 that holds a sample 200-2 made of a rectangular-shaped mask in this example is mounted on the top surface of the stage 100-2 via an electrostatic chuck 120-2.

The stage 100-2 has a movement region with a stroke of effective distance+approaching distance (inspection maximum speed*speed stabilization time) of the sample 200-2 so as to allow imaging of an effective region of the sample (mask) 200-2 and defect inspection. For instance, provided that the effective distance of the sample 200-2 in the X direction and the Y direction is 300 mm and the approaching distance is 100 mm/s*0.5 s=50 mm, the stage 100-2 has a movement region with a stroke of 400 mm.

A cross-sectionally rectangular-shaped dust collecting electrode 122-2 continuously extending in a manner of a rectangular frame is provided at a position that is separated by a prescribed interval from the sample 200-2 provided on the stage 100-2 and surrounds the entire periphery of the sample 200-2. Furthermore, a gap control plate 124-2 that is disposed above the sample (mask) 200-2 and the dust collecting electrode 122-2, which are mounted on the stage 100-2, and has a through hole 124a-2 at the center is horizontally arranged with a slight gap from the inner peripheral surface of the vacuum chamber 12-2. An optical system element of the electron beam inspection apparatus, i.e., condenser lens 330-2, is disposed in the through hole 124a-2. Through the condenser lens 330-2, the surface of the sample 200-2 mounted on the stage 100-2 is irradiated with an electron beam. The through hole 124a-2 is configured to have a size slightly larger than the outer dimensions of the condenser lens 330-2.

The dust collecting electrode 122-2 is made of nonmagnetic material, such as phosphor bronze or Ti, so as to prevent bending of an electron beam due to magnetic fields and variation of an orbit. The electron beam includes a primary irradiation electron beam, a secondarily emitted electron beam emitted from the sample 200-2, and a mirror electron beam reflected in proximity to sample 200-2.

The gap control plate 124-2 may be a flat plate that is made of, for instance, phosphor bronze, Ti, SUS material or the like and has a thickness of 0.3 to 5 mm. In order to allow the potential to be stabilized and prevent contamination, it is preferred that the gap control plate 124-2 have a coating of Au, Pt, Ru, Os or the like. The gap control plate 124-2 is configured to have a size covering a region where the dust collecting electrode 122-2 does not protrude from the gap control plate 121-2 even when the stage 100-2 moves in the movement region. This configuration can prevent the electric field distribution from collapsing to change the orbit of the particles when the stage 100-2 moves and the sample 200-2 mounted on the stage 100-2 moves to the most deviating position in the vacuum chamber 112-2, and can prevent the particles from flying to the sample 200-2 and adhering to the surface of the sample. Note that the gap control plate 124-2 is not necessarily provided. This point is equivalently applied to the following examples.

In this example, as shown in FIG. 22, through use of the dust collecting electrode 122-2 continuous in a manner of a rectangular frame, the entire periphery of the sample 200-2 arranged on the stage 100-2 is integrally surrounded by the dust collecting electrode 122-2. This arrangement can prevent formation of gaps at positions along the longitudinal directions of the dust collecting electrode 122-2 and occurrence of uneven portions of electric fields. Thus, this arrangement can prevent particles from entering the inside surrounded by the dust collecting electrode 122-2 through what is called the gaps of electric fields.

The dust collecting electrode 122-2 does not necessarily surround the entire periphery of the sample 200-2. It is sufficient that the electric fields formed by the dust collecting electrode 122-2 surround the periphery of the sample 200-2. For instance, as shown in FIG. 23, four dust collecting electrodes 122a-2 that linearly extend may be arranged so as to extend over the substantially entire lengths of the sides of the sample 200-2 to allow the dust collecting electrodes 122a-2 to surround the substantially entire outer periphery except the corners of the sample 200-2 and therearound. Although not shown, linearly extending dust collecting electrodes may be separated at the middle thereof. In this case, electric fields are distorted between the dust collecting electrodes adjacent to each other. However, it is sufficient that the dust collecting electrodes can achieve a necessary potential distribution. For instance, no problem occur only if in a two-dimensional view, D/L 4, where the width of the dust collecting electrode is D, and the distance between the dust collecting electrodes is L. This fact is also analogously applicable to the following embodiments.

Figure 24:
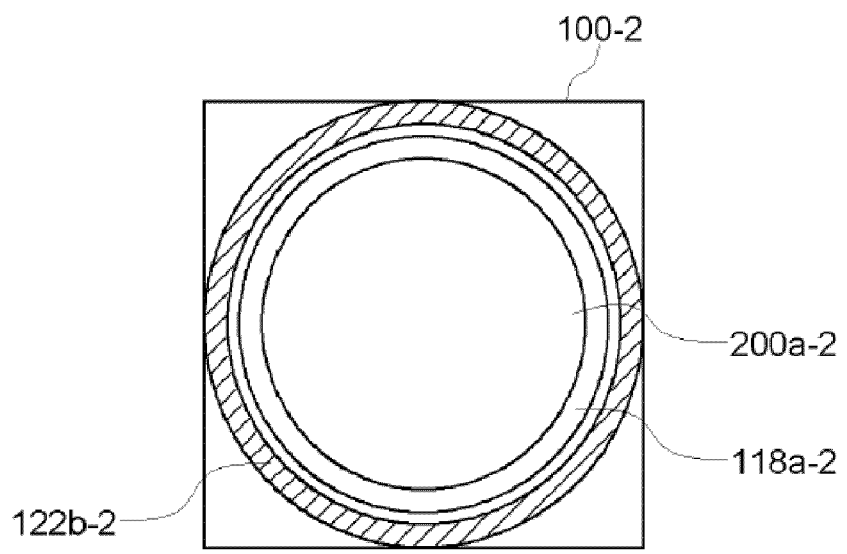
FIG. 24 is a plan view showing a relationship between a stage, a circular-shaped sample and a dust collecting electrode of Third Embodiment according to an embodiment of the present invention.
Figure 25:
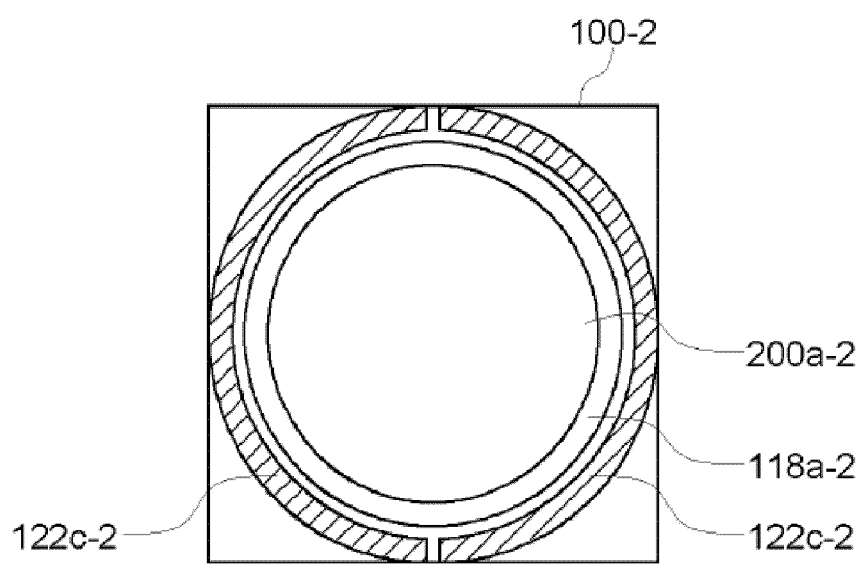
FIG. 25 is a plan view showing a relationship between a stage, a circular-shaped sample, and a dust collecting electrode of Fourth Embodiment according to an embodiment of the present invention.

In the cases shown in FIGS. 21 to 23, a rectangular mask is adopted as the sample 200-2. In the case of using a circular-shaped semiconductor wafer as a sample, the entire periphery of the sample 200a-2 is integrally surrounded as shown in FIG. 24 by arranging a circular-shaped sample (semiconductor wafer) 200a-2 held by a circular-shaped holder 118a-2 on a stage 100-2, and further arranging a continuous circular ring-shaped dust collecting electrode 122b-2 around the sample. In this case, as shown in FIG. 25, a pair of half-circular dust collecting electrodes 122c-2 may be arranged to face each other and form a perfect circle, and the substantially entire periphery of the circular-shaped sample (semiconductor wafer) 200a-2 arranged on the stage 100-2 may be surrounded by the dust collecting electrodes 122c-2. Although not shown, at least three dust collecting electrodes may be arranged apart from each other so as to extend in the circumference direction.

In all the cases, a prescribed voltage is applied to the entire one or all the dust collecting electrode(s) 122-2 surrounding the sample 200-2 arranged on the stage 100-2 to collect dust, and subsequently an electron beam is emitted from the electron beam source 310-2 (see FIG. 19), thereby irradiating the sample 200-2 on the stage 100-2 with the electron beam. Secondary electrons emitted from the sample due to the irradiation, or mirror electrons reflected by the sample surface or therearound are then detected by the detector 400-2 (see FIG. 19). Image processing is performed by the image processor 500-2, and an image of the sample surface is acquired.

Figure 26:
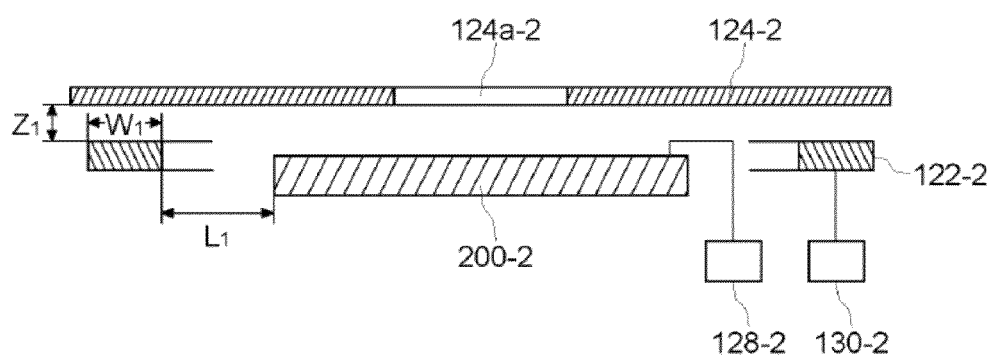
FIG. 26 is a sectional view showing a sample, a dust collecting electrode and a gap control plate in an enlarged manner according to an embodiment of the present invention.

FIG. 26 is a diagram showing a sample 200-2, a dust collecting electrode 122-2 and a gap control plate 124-2 in an enlarged manner. As shown in FIG. 26, a first power source 128-2 that applies a prescribed voltage to the surface of the sample 200-2 is connected to this sample. A second power source 130-2 that applies a prescribed voltage to the dust collecting electrode 122-2 is connected to this dust collecting electrode. The thickness of the dust collecting electrode 122-2 is, for instance, 0.1 to 5 mm. It is preferred that the width W1 of the dust collecting electrode 122-2 be wide as much as possible. However, the wider the electrode is, the larger the size of the dust collecting electrode 122-2 in the vacuum chamber 112-2 is. Accordingly, the width, typically, ranges from 5 to 50 mm. It is preferred that the distance L1 between the sample 200-2 and the dust collecting electrode 122-2 be used in a range satisfying the relationship of $0.5L1 < W1 < 5L1$ in relation to the width W1 of the dust collecting electrode 122-2.

In this example, for instance, a voltage of −1 to −5 kV is applied to the surface of the sample 200-2 through the first power source 128-2. A voltage that has a polarity identical to the polarity of the voltage applied to the sample 200-2 and an absolute value larger by e.g., 0.5 to 5 kV than the absolute value of the voltage applied to the sample 200-2, is applied to the dust collecting electrode 122-2 through the second power source 130-2. That is, for instance, in the case of applying a voltage of −3 kV to the sample 200-2, a voltage that ranges from −3.5 to −8 kV, e.g., −5 kV, is applied to the dust collecting electrode 122-2.

The vacuum chamber 112-2 is made of metal material, such as iron material or aluminum, and has the earth potential. If foreign matters, such as particles, residing in the vacuum chamber 112-2 are charged by static electricity or the like, in the case where the sample 200-2 has a negative potential, positively charged foreign matters, such as particles, are attracted by the electric field and fly toward the sample 200-2.

According to this example, the entire periphery of the sample 200-2 to which the negative potential is applied is surrounded by the dust collecting electrode 122-2, and a negative voltage that has a higher absolute value than the absolute value of the voltage applied to the sample 200-2, thereby allowing the most of the flying foreign matters, such as particles, attracted by the electric field to be captured by the dust collecting electrode 122-2. The probability that the foreign matters, such as particles, fly toward the sample 200-2 and adhere to the surface of the sample can be significantly reduced. Accordingly, adhesion of the foreign matters to the surface of the sample 200-2 can be significantly reduced.

In this example, the gap control plate 124-2 is provided that prevents foreign matters, such as particles, from passing through an orbit apart from the dust collecting electrode 122-2 and adhering to the sample 200-2. The gap control plate 124-2 is thus provided. Accordingly, the attracting force by the dust collecting electrode 122-2 for foreign matters, such as particles, passing through the orbit apart from the dust collecting electrode 22-2 is reduced, thereby reducing the probability that the foreign matters, such as particles, are captured by the dust collecting electrode 122-2 in inverse proportion to the distance. In the case of applying a negative voltage to the sample 200-2, in order not to reduce the probability of capturing foreign matters, the electric field intensity A between the sample 200-2 and the dust collecting electrode 122-2 is set negative ($A<0$), which can increase the attracting force by the dust collecting electrode 122-2 and, in turn, increase the probability that the dust collecting electrode 122-2 captures foreign matters, such as particles. Moreover, the electric field intensity (absolute value) B between the gap control plate 124-2 and the dust collecting electrode 122-2 is set to have a relationship that $0.1 \leq B$ (absolute value) $\leq 10$ kV/mm. This setting can further increase the probability that the dust collecting electrode 122-2 captures foreign matters, such as particles.

For instance, a negative voltage of −1 to −5 kV is applied to the sample 200-2, and a negative voltage of −1.5 to −10 kV that has an absolute value higher than the absolute value of the negative voltage applied to the sample 200-2 is applied to the dust collecting electrode 122-2; the difference between the voltages is −0.5 to −5 kV. Provided that the distance L1=10 mm between the sample 200-2 and the dust collecting electrode 122-2 and the distance Z1=8 mm between the gap control plate 124-2 and the dust collecting electrode 122-2 in the case where the gap control plate 124-2 is at the earth potential, the electric field intensity A between the sample 200-2 and the dust collecting electrode 122-2 is negative ($A<0$). If the electric field intensity (absolute value) B=0.19 to 1.25 kV/mm (=1.5 to 10 kV/8 mm) between the gap control plate 124-2 and the dust collecting electrode 122-2, particularly, a voltage of −5 kV is applied to the dust collecting electrode 122-2, the electric field intensity (absolute value) B=0.625 kV/mm (=5 kV/8 mm), which is an effective condition. At this time, the withstanding voltage of the space is set not to exceed 10 kV/mm, which can prevent electric discharges from occurring in the space.

Figure 27:
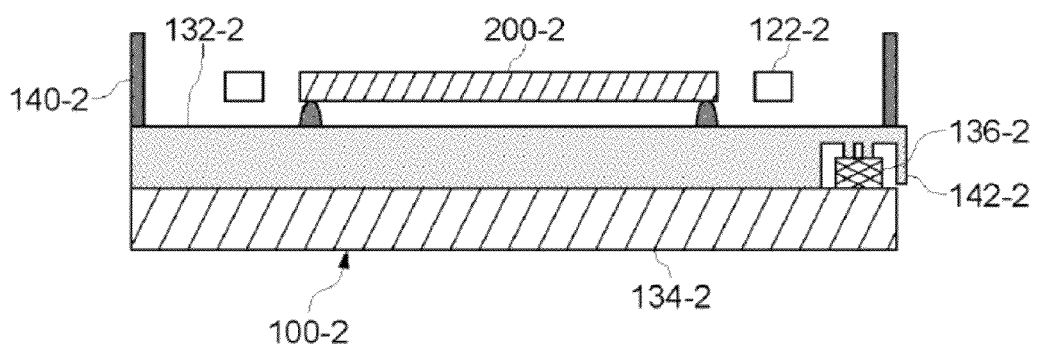
FIG. 27 is a diagram showing details of a stage according to an embodiment of the present invention.

FIG. 27 shows the details of the stage 100-2. As shown in FIG. 27, the stage 100-2 is configured by stacking the X stage 132-2 on the Y stage 134-2. An ultrasonic motor 136-2 is provided between the X stage 132-2 and the Y stage 134-2. A first dust proof cover 140-2 whose top reaches the top of the dust collecting electrode 122-2 is arranged at a position of covering the outer side of the dust collecting electrode 122-2 on the top surface of the stage 100-2. A second dust proof cover 142-2 that blocks the opening end of a storage for the ultrasonic motor 36-2 is arranged at the outer side of the ultrasonic motor 136-2.

The first dust proof cover 140-2 is thus arranged, which can prevent foreign matters, such as particles, from being dispersed toward the surface of the sample 200-2 and adhering to the surface. The second dust proof cover 142-2 is arranged at the outer side of the ultrasonic motor 136-2, which is a source of particles, which can prevent foreign matters, such as particles, dispersed from the ultrasonic motor 136-2 from being dispersed into the vacuum chamber 112-2. Prevention of the foreign matters, such as particles, from being dispersed from the source of foreign matters, such as particles, into the vacuum chamber 112-2 is significantly effective for the case of using a motor of a type driving by means of friction against a wall of a piezo-actuator or the like.

Figure 28:
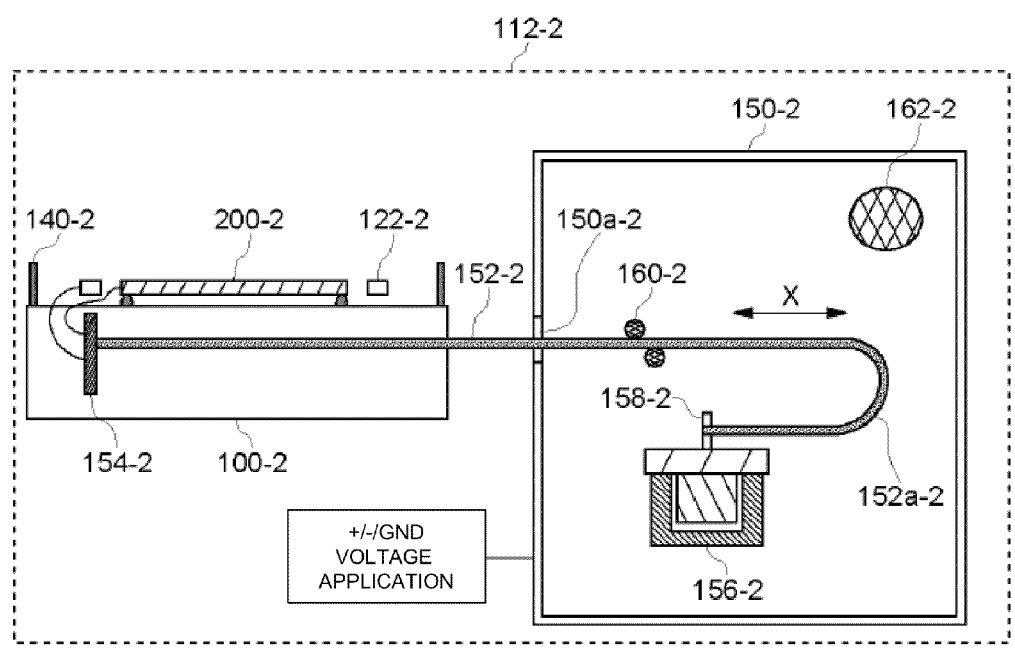
FIG. 28 is a diagram showing an overview of a wiring box and a stage arranged in a vacuum chamber according to an embodiment of the present invention.

In this case, as shown in FIG. 28 in detail, a wiring box 150-2 having a hermetic structure is arranged in the vacuum chamber 112-2. The wiring box 150-2 is for preventing foreign matters, such as particles, caused from a cable due to bending and rubbing of the cable from being dispersed into the vacuum chamber 112-2. In this case, the entire portions where bending of a cable 152-2 occurs due to movement of the stage 100-2 on which the sample 200-2 is arranged are accommodated in the wiring box 150-2. Description will be made in further detail. The power source (800-2 in FIG. 19, 128-2 in FIGS. 29 to 32) for applying a prescribed voltage to the sample 200-2 and the power source (130-2 in FIGS. 29 to 31) for applying a prescribed voltage to the dust collecting electrode 122-2 are provided outside the wiring box 150-2. Electric connection between the outside power source to a terminal table 156-2 is further connected to the outer power source via a cable (not shown) extending from the terminal table 156-2, and a feedthrough provided at the vacuum chamber 112-2. The terminal table 156-2 is provided with two pairs of terminals for applying a power source voltage to the sample and the dust collecting electrode. The cable 152-2 includes two pairs of power source lines for transmitting a power source voltage, and one ends of the two pairs of power source lines are electrically connected to the two pairs of terminals of the terminal table 156-2. As shown in the diagram, one end of the cable 160-2 is mechanically fixed to a moving plate 158-2 that is arranged in proximity to the terminal table 156-2 and movable. The length of the cable between the moving plate 158-2 and the terminal table 156-2 is redundantly secured in consideration of a movement range of the moving plate 158-2. Meanwhile, a fixation plate 154-2 is fixed to the stage 100-2. Two pairs of terminals for applying a voltage to the sample and the dust collecting electrode are provided on the fixation plate. The corresponding power source lines of the cable 152-2 are electrically and mechanically connected to the terminals.

Furthermore, as shown in the diagram, the cable 152-2 connected to the fixation plate 154-2 fixed to the stage 100-2 linearly extends from the stage 100-2 toward the wiring box 150-2, passes through a slit 150a-2 provided at the wiring box 150-2, reaches the inside of the wiring box 150-2 and subsequently is bent downward by 180° and reversed. As described above, the other end of the cable 152-2 is mechanically fixed to the moving plate 158-2 disposed in the wiring box 150-2, and the distal end of this cable is connected to the terminal table 156-2. Accordingly, when the stage 100-2 moves in the X direction, bending occurs only at a bent portion 152a-2 of the cable 152-2 in the wiring box 150-2.

A guide roller 160-2 that extends in the Y direction (the direction orthogonal to the sheet of FIG. 28) and guides the cable 152-2 is arranged in the wiring box 150-2. When the stage 100-2 moves in the Y direction, this stage moves in the Y direction along the guide roller 160-2, and the moving plate 158-2 moves. Accordingly, no stress in the Y direction is applied to a length of the cable 152-2 up to the moving plate 158-2.

In the aforementioned embodiment, the movable moving plate 158-2 is provided. However, if it is configured that only expansion and contraction of the bent portion 52a-2 of the cable 152-2 can accommodate variation of the cable 152-2 due to movement of the stage 100-2 in the X direction and the Y direction, the cable 52-2 may be mechanically fixed with a fixation plate instead of the moving plate.

As described above, the entire bent portion of the cable 152-2 is in the wiring box 150-2 and a hole opening to the outside of the wiring box 150-2 is small. Accordingly, the probability that foreign matters, such as particles, occurring in the wiring box 150-2 are emitted outside the wiring box 150-2 is significantly reduced. The most of the foreign matters adheres to the inner wall of the wiring box 150-2. Furthermore, in this example, the dust collecting electrode 162-2 for the wiring box 150-2 is arranged in this wiring box, and the voltage for capturing foreign matters, such as particles, is applied to the dust collecting electrode 162-2. This application can significantly reduce the probability that foreign matters, such as particles, are dispersed outside the wiring box 150-2.

Taking measures of any of (1) aligning the lengths of the cables, (2) fixing the cables using a wire band or the like to correct the cables, and (3) adopting a flat cable, can reduce occurrence of particles due to rubbing of the multiple cables. That is, alignment of the lengths of the multiple cables and fixation of these cables integrate the cables into a cable bundle. Although movement of the stage causes bending at the cable, rubbing between cables at this time can be reduced and thus occurrence of foreign matters, such as particles, can be reduced. Adoption of the flat cable enables multiple wires to be integrated into one cable, which negates rubbing between cables. In the case where a flat cable including multiple wires cannot immediately be adopted, combination of the foregoing (1) and (2) is effective.

Figure 29:
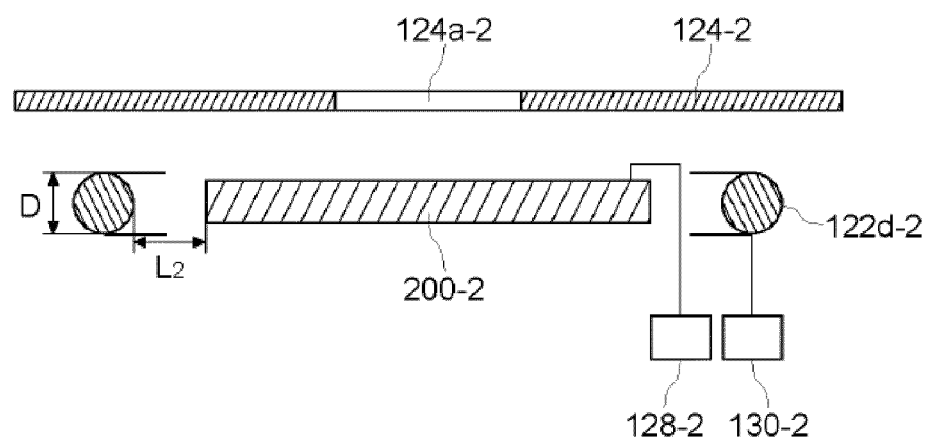
FIG. 29 is a sectional view showing a sample, another dust collecting electrode and a gap control plate in an enlarged manner according to an embodiment of the present invention.

In the foregoing example, the cross-sectionally rectangular-shaped dust collecting electrode 122-2 is adopted. Alternatively, as shown in FIG. 29, a cross-sectionally circular-shaped dust collecting electrode 122d-2 may be adopted. It is preferred that the diameter D of the dust collecting electrode 122d-2 be configured in a range satisfying a relationship of $0.5L2 < D < 5L2$ in relation to the distance L2 between the sample 200-2 and the dust collecting electrode 122d-2. If the diameter D of the dust collecting electrode 122d-2 is shorter than the foregoing diameter, the capturing probability of the dust collecting electrode 122d-2 is reduced. If the diameter is larger, the capturing probability of the dust collecting electrode 122d-2 is not changed, and, in some cases, this electrode attracts excessive foreign matters, such as particles.

Figure 30:
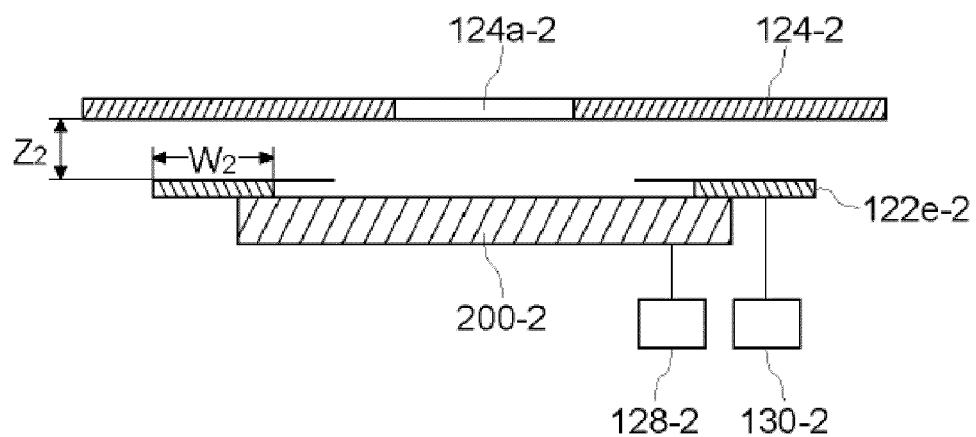
FIG. 30 is a sectional view showing a sample, still another dust collecting electrode and a gap control plate in an enlarged manner according to an embodiment of the present invention.

Furthermore, in the foregoing example, the dust collecting electrode 122-2 is arranged at a position separated by a prescribed interval from the sample 200-2, and a voltage that has the same polarity as the voltage applied to the sample 200-2 and has an absolute value higher than the absolute value of the voltage applied to the sample 200-2 is applied to the dust collecting electrode 122-2. Alternatively, as shown in FIG. 30, a cross-sectionally rectangular-shaped dust collecting electrode 122e-2 continuous in a manner of a rectangular frame may be arranged at an outer peripheral portion of the sample 200-2 while causing an inner peripheral portion of the electrode to be in contact and surrounding the entire periphery of the sample, and the same voltage as the voltage applied to the sample 200-2 through a first power source 128-2 may be applied to the dust collecting electrode 122e-2 through a second power source 130-2. The thickness of the dust collecting electrode 122e-2 ranges, for instance, from 0.1 to 5 mm, and the width W2 is analogous to the width of the foregoing dust collecting electrode 122-2, e.g., 5 to 50 mm.

Figure 31:
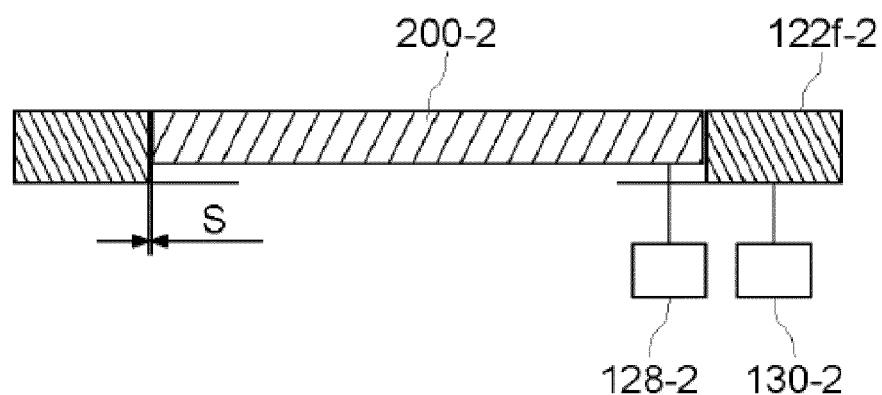
FIG. 31 is a sectional view showing a sample and still another dust collecting electrode in an enlarged manner according to an embodiment of the present invention.

In the example of FIG. 30, the dust collecting electrode 122e-2 that has an inner shape smaller than the outer shape of the sample 200-2 is adopted, and the inner peripheral portion of the dust collecting electrode 122e-2 is in contact with the outer peripheral portion of the sample 16-2. Alternatively, as shown in FIG. 31, a rectangular-frame-shaped dust collecting electrode 122f-2 having an inner shape slightly larger than the outer shape of the sample 200-2 may be adopted, and the dust collecting electrode 122f-2 may be arranged such that the dust collecting electrode 122f-2 surrounds the entire periphery of the sample 200-2 separated by a slight gap S. The gap S ranges, for instance, 1 to 500 μm.

In the example of FIG. 30, a negative voltage of, e.g., −1 to −5 kV is applied to the sample 200-2 through the first power source 128-2. Furthermore, the same voltage as the voltage applied to the sample 200-2 is applied to the dust collecting electrode 122e-2 through the second power source 130-2; that is, a voltage of −3 kV is applied in the case of applying a voltage of −3 kV to the sample 200-2.

Likewise, as described above, in the case where the potential of the sample 200-2 is negative, positively charged foreign matters, such as particles, are attracted by electric fields to fly toward the sample 200-2. In the example of FIG. 30, the dust collecting electrode 122e-2 having the same potential as the potential of the sample 200-2 is arranged at a position surrounding the entire periphery of the sample 200-2. Accordingly, the most of the foreign matters, such as particles, attracted by the electric fields to fly is captured by the dust collecting electrode 122e-2. Thus, the most of foreign matters, such as particles, can be captured by the dust collecting electrode 122e-2 arranged around the sample 200-2. Accordingly, foreign matters, such as particles, flying to the surface of the sample 200-2 and adhering to this surface are reduced, which can prevent the foreign matters from adhering to the surface of the sample 200-2.

In the example of FIG. 30, provided that the distance between the dust collecting electrode 122e-2 and the gap control plate 124-2 is Z2, the case where W2>4Z2 is particularly advantageous in relation to the width W2 of the dust collecting electrode 122e-2. If the voltage density B (absolute value) between the dust collecting electrode 122e-2 and the gap control plate 124-2 is set larger than 0.1 kV/mm (B(absolute value)>0.1 kV/mm), the case is further advantageous.

Figure 32:
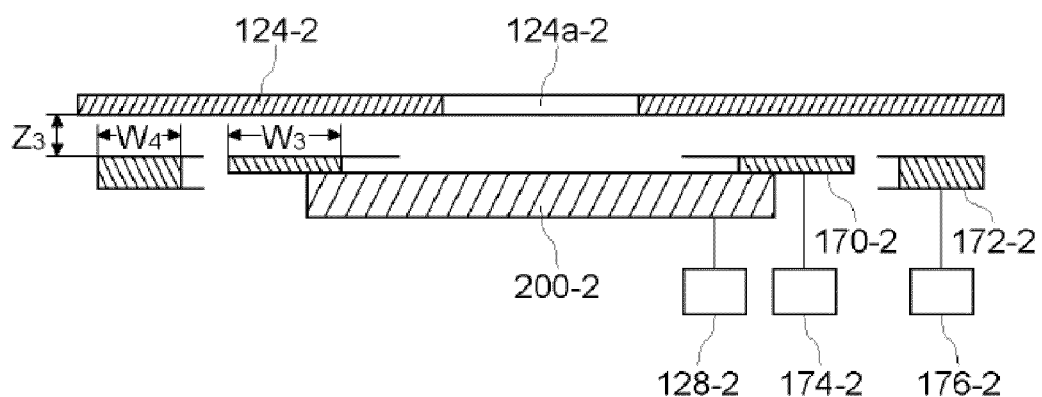
FIG. 32 is a sectional view showing a sample, still another dust collecting electrode and a gap control plate in an enlarged manner according to an embodiment of the present invention.

FIG. 32 shows another example combining the example shown in FIG. 26 and the example shown in FIG. 30. In this example, a cross-sectionally rectangular-shaped first dust collecting electrode 170-2 that is, for instance, continuous in a manner of a rectangular frame is arranged so as to surround the entire periphery of the sample while causing the inner peripheral portion of the electrode to be in contact with the outer peripheral portion of the sample 200-2, and a cross-sectionally rectangular-shaped second dust collecting electrode 172-2 that is, for instance, continuous in a manner of a rectangular frame is arranged at the a position separated by a prescribed interval from the first dust collecting electrode 170-2 so as to surround the entire periphery of the first dust collecting electrode 170-2. A second power source 174-2 is connected to the first dust collecting electrode 170-2. A third power source 176-2 is connected to the second dust collecting electrode 172-2.

As described above, the linearly extending second dust collecting electrode may be arranged so as to extend over the entire length of each side of the first dust collecting electrode, thereby causing the second dust collecting electrode to surround the substantially entire outer periphery of the first dust collecting electrode. Alternatively, the linearly extending second dust collecting electrode may be separated at the middle thereof.

In the example of FIG. 32, as described above, a voltage of, e.g., −1 to −5 kV is applied to the sample 200-2 through the first power source 128-2. The same voltage as the voltage applied to the sample 200-2 is applied to the first dust collecting electrode 170-2; for instance, in the case of applying a voltage of −3 eV to the sample 200-2, a voltage of −3 eV is applied to this electrode. Furthermore, a voltage that has the same polarity as the polarity of the voltage applied to the sample 200-2 and has an absolute value higher by, e.g., 0.5 to 5 kV, than the absolute value of the voltage applied to the sample 200-2 is applied to the second dust collecting electrode 172-2. That is, in the case of applying, e.g., a voltage of −3 kV to the sample 200-2, a voltage ranging from −3.5 to −8 kV, e.g., −5 kV, is applied to the second dust collecting electrode 172-2.

Also in this example, substantially as with the example shown in the foregoing FIG. 26 and the like, setting of the electric field intensity A between the sample 200-2 and the second dust collecting electrode 172-2 to be negative (A<0) in the case of applying a negative voltage to the sample 16-2 can increase the attracting force of the second dust collecting electrode 172-2 and, in turn, increase the probability that the second dust collecting electrode 172-2 captures foreign matters, such as particles. Moreover, setting of the electric field intensity (absolute value) B between the gap control plate 124-2 and the second dust collecting electrode 172-2 to have a relationship of 0.1≤B (absolute value)≤10 kV/mm can further increase the probability that the second dust collecting electrode 172-2 captures foreign matters, such as particles.

As with the dust collecting electrode 122e-2 shown in the foregoing FIG. 29, the first dust collecting electrode 170-2 has a thickness ranging, e.g., from 0.1 to 5 mm, and a width W3 ranging, e.g., from 5 to 50 mm. As with the dust collecting electrode 122 shown in the foregoing FIG. 24, the second dust collecting electrode 172-2 has a thickness approximately ranging, e.g., from 0.1 to 50 mm and a width W4 approximately ranging, e.g., from 5 to 50 mm.

For instance, a negative voltage of −1 to −5 kV is applied to the sample 200-2 and the first dust collecting electrode 170-2. A negative voltage of −1.5 to −10 kV, which is further negative by −0.5 to −5 kV than the negative voltage applied to the sample 200-2 and the first dust collecting electrode 170-2, is applied to the second dust collecting electrode 172-2. Provided that the distance Z8=8 mm between the gap control plate 124-2 and the second dust collecting electrode 172-2 in the case where the gap control plate 124-2 is at the earth potential, the electric field intensity A is negative (A<0) between the sample 200-2 and the second dust collecting electrode 172-2, and the electric field intensity (absolute value) B=0.19 to 1.25 kV/mm (=1.5 to 10 kV/8 mm) between the gap control plate 124-2 and the second dust collecting electrode 172-2; in particular, application of a voltage of −5 kV to the dust collecting electrode 122-2 sets the electric field intensity (absolute value) B=0.625 kV/mm (=5 kV/8 mm), which is an advantageous condition. At this time, setting of the spatial withstanding voltage not exceeding 10 kV/mm can prevent discharge from occurring in the space.

First Embodiment

Figure 33:
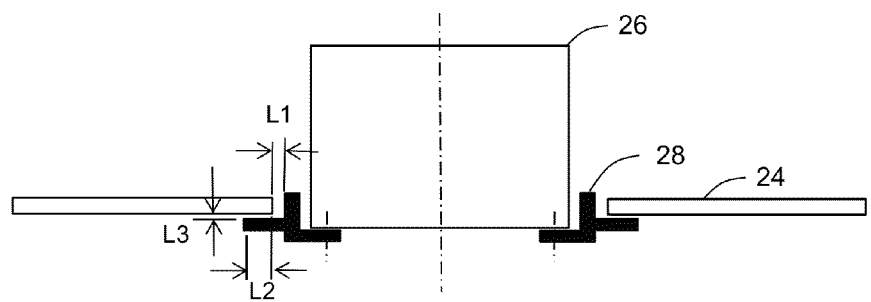
FIG. 33 is a diagram illustrating a main part of the inspection apparatus of First Embodiment of the present invention.

A configuration of an inspection apparatus of a first embodiment of the present invention is described with reference to FIG. 33. FIG. 33 is a diagram illustrating a main part of the inspection apparatus of this embodiment. As shown in FIG. 33, the inspection apparatus 10-2 of this embodiment includes a cover member 28-2 that blocks a gap between a gap control plate 24-2 and a condenser lens 26-2 (also see FIG. 34). The gap control plate 24-2 is arranged above the stage 14-2 so as to cover the surface of the sample 16-2 arranged on the stage 14-2. A through hole 24a-2 allowing an electron beam to pass therethrough is provided at the center (inside) of the gap control plate 24-2. A condenser lens 26-2 in a secondary system lens is arranged in the through hole 24a-2. The material of the cover member 28-2 is an insulator (e.g., a ceramic or Teflon (registered trademark)).

As shown in FIG. 33, in view of the direction perpendicular to the gap control plate 24-2 (sight direction), the gap between the through hole 24a-2 and the condenser lens 26-2 is blocked with the cover member 28-2. For instance, the cover member is configured to have an outer diameter larger by L2 (3 to 10 mm) than the inner diameter of the through hole 24a-2.

Meanwhile, as shown in FIG. 33, in view of a direction parallel to the gap control plate 24-2 (sight direction), a gap is provided between the gap control plate 24-2 and the cover member 28-2. For instance, a gap of L1 (0.5 to 3 mm) is formed between the gap control plate 24-2 and the cover member 28-2 in a direction (sight direction) parallel to the optical axis of the condenser lens 26-2. A gap of L3 (0.5 to 2 mm) is formed between the gap control plate 24-2 and the cover member 28-2 in the direction (sight direction) perpendicular to the optical axis of the condenser lens 26-2.

Although not shown here, as described above, the inspection apparatus of this embodiment includes the electron beam source, a primary electron optical system that guides an electron beam emitted from the electron beam source, a stage on which a sample irradiated with primary electrons guided by the primary electron optical system, a secondary electron optical system that guides secondary charged particles emitted from the surface of the sample due to irradiation with the electron beam, and a detector that detects secondary charged particles guided by the secondary electron optical system. The primary electron optical system includes a primary system lens. The secondary electron optical system includes a secondary system lens.

According to the inspection apparatus 10-2 of the first embodiment of the present invention, the cover member 28-2 is thus provided, which can reduce adhesion of foreign matters (particles) to the surface of the sample 16-2. That is, in this embodiment, as shown in FIG. 33, the gap (the gap viewed in the direction (sight direction) perpendicular to the gap control plate 24-2) between the through hole 24a-2 of the gap control plate 24-2 and the condenser lens 26-2 is blocked with the cover member 28-2, which can reduce adhesion of foreign matters (particles) to the surface of the sample 16-2.

In this embodiment, a gap (a gap viewed in the direction (sight direction) parallel to the gap control plate 24-2) is provided between the gap control plate 24-2 and the cover member 28-2. That is, the gap control plate 24-2 and the cover member 28-2 are not in contact with each other (noncontact). Accordingly, vibrations of the gap control plate 24-2 can be prevented from being transmitted to the condenser lens 26-2, and an image can be prevented from being distorted by vibrations of the gap control plate.

Second Embodiment

Next, an inspection apparatus of a second embodiment of this the present invention is described. Here, the difference of the inspection apparatus of the second embodiment from the apparatus of the first embodiment is mainly described. Unless otherwise noted, the configuration and operation of this embodiment is analogous to those of the first embodiment.

Figure 34:
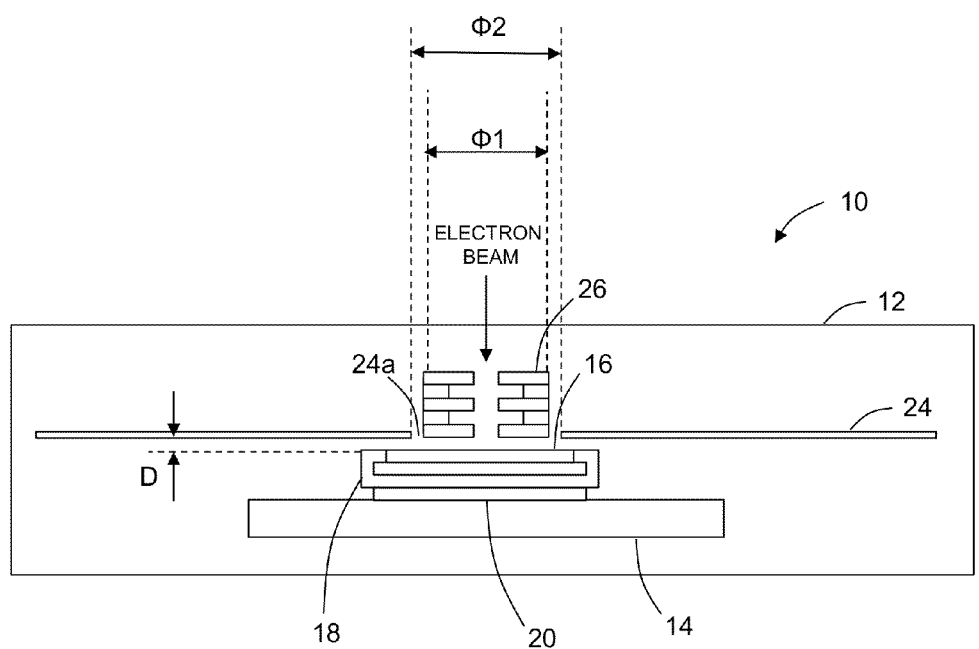
FIG. 34 is a diagram illustrating the inspection apparatus of Second Embodiment of the present invention.

FIG. 34 is a diagram illustrating the inspection apparatus of this embodiment. As shown in FIG. 34, an inspection apparatus 10-2 of this embodiment does not include a dust collector 22-2 for reducing adhesion of foreign matters to a sample surface (also see FIG. 35). In this case, the width D of a gap between a through hole 24a-2 and a condenser lens 26-2 viewed in a direction perpendicular to a gap control plate 24-2 (sight direction) ranges from 5 to 30 mm.

According to such an inspection apparatus of a second embodiment of the present invention, the width of the gap (a gap viewed in the direction perpendicular to the gap control plate (sight direction)) between the surface of the sample and the gap control plate is significantly small (5 mm to 30 mm). Accordingly, the electric field distribution can be stable, which can cause charged foreign matters (particles) not to be attracted to the sample surface.

Third Embodiment

Next, an inspection apparatus of a third embodiment of the present invention is described. Here, the difference of the inspection apparatus of the third embodiment from the apparatus of the second embodiment is mainly described. Unless otherwise noted, the configuration and operation of this embodiment is analogous to those of the second embodiment.

Figure 35:
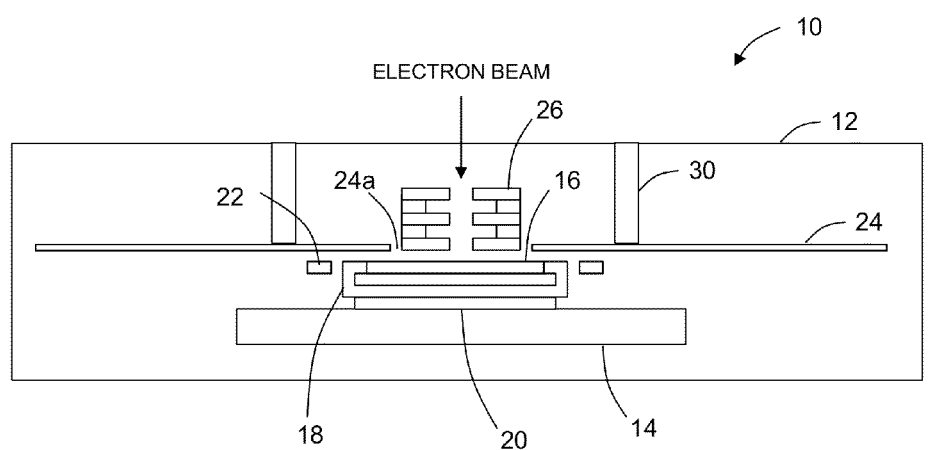
FIG. 35 is a diagram illustrating the inspection apparatus of Third Embodiment of the present invention.

FIG. 35 is a diagram illustrating the inspection apparatus of this embodiment. As shown in FIG. 35, according to the inspection apparatus of this embodiment, pillar columns 30-2 are attached to the ceiling surface of a vacuum chamber 12-2. A gap control plate 24-2 is attached in the vacuum chamber 12-2 via the pillar columns 30-2. For instance, it is preferred that the lengths of the pillar columns 30-2 range from 70 to 150 mm.

The inspection apparatus 10-2 of this embodiment further includes a dust collector 22-2 for reducing adhesion of foreign matters to the sample surface. Note that, as with the second embodiment, the dust collector 22-2 for reducing adhesion of foreign matters to the sample surface is not necessarily provided.

According to the inspection apparatus of the third embodiment of the present invention, the pillar columns 30-2 are attached to the ceiling surface of the vacuum chamber 12-2, and the gap control plate 24-2 is attached in the vacuum chamber 12-2 via the pillar column 30-2. Accordingly, the potential can be changed only by means of the gap control plate 24-2 to control the electric field. A space through which a hand can be put into the vacuum chamber 12-2 can be secured by detaching the gap control plate 24-2. Accordingly, maintenance is improved. For instance, an objective lens can be detachable. Furthermore, maintenance and cleaning of devices on the mirror plate can be allowed.

The embodiments of the present invention have been described using the examples. However, the scope of the present invention is not limited thereto, and can be changed or deformed according to objects within a scope described in claims.

As described above, the inspection apparatus of the present invention (first aspect) exerts an advantageous effect that can facilitate reduction in cost of the apparatus, and is useful as a semiconductor inspection apparatus and the like.

As described above, the inspection apparatus according to the present invention (second aspect) includes the cover member, which exerts an advantageous effect that can reduce adhesion of foreign matters (particles) to the sample surface. This apparatus is used as a semiconductor inspection apparatus and the like, which is useful.

What is claimed is:

1. An inspection apparatus, comprising:
    beam generation means for generating any of charged particles and electromagnetic waves as a beam;
    a primary optical system that guides the beam into an inspection object held on a movable stage in a working chamber and irradiates the inspection object with the beam;
    a secondary optical system that detects secondary charged particles occurring from the inspection object;
    an image processing system that forms an image on the basis of the detected secondary charged particles;
    a linear motor that drives the movable stage;
    a Helmholtz coil that causes a magnetic field for canceling a magnetic field caused by the linear motor when the movable stage is driven;
    current detection means for detecting drive current for driving the linear motor; and
    magnetic field control means for controlling an intensity of a magnetic field caused by the Helmholtz coil according to the drive current detected by the current detection means.

2. The inspection apparatus according to claim 1, further comprising
position detection means for detecting a position of the movable stage,
wherein the magnetic field control means controls the intensity of the magnetic field caused by the Helmholtz coil, according to the drive current detected by the current detection means and the position detected by the position detection means.

\* \* \* \* \*